US011479813B2

(12) United States Patent
Helbing et al.

(10) Patent No.: US 11,479,813 B2
(45) Date of Patent: Oct. 25, 2022

(54) QUANTITATIVE PCR-BASED ENVIRONMENTAL DNA ASSAYS

(71) Applicant: UVic Industry Partnerships Inc., Victoria (CA)

(72) Inventors: Caren Christiane Helbing, Victoria (CA); Nicholas Veldhoen, Victoria (CA)

(73) Assignee: UVic Industry Partnerships Inc., Victoria (CA)

( * ) Notice: Subject to any disclaimer, the term of this patent is extended or adjusted under 35 U.S.C. 154(b) by 0 days.

(21) Appl. No.: 15/729,478

(22) Filed: Oct. 10, 2017

(65) Prior Publication Data

US 2018/0100184 A1 Apr. 12, 2018

Related U.S. Application Data

(60) Provisional application No. 62/406,802, filed on Oct. 11, 2016.

(30) Foreign Application Priority Data

Apr. 13, 2017 (CA) ................................ CA 2964374

(51) Int. Cl.
*C12Q 1/686* (2018.01)
*C12Q 1/6888* (2018.01)
*C12Q 1/6895* (2018.01)
*C12Q 1/6851* (2018.01)

(52) U.S. Cl.
CPC ........... *C12Q 1/686* (2013.01); *C12Q 1/6851* (2013.01); *C12Q 1/6888* (2013.01); *C12Q 1/6895* (2013.01)

(58) Field of Classification Search
CPC combination set(s) only.
See application file for complete search history.

(56) References Cited

U.S. PATENT DOCUMENTS 5,541,308 A * 7/1996 Hogan ................ C12Q 1/6811 536/23.1
2004/0176584 A1 * 9/2004 Terlesky ................ C12Q 1/689 536/24.3

FOREIGN PATENT DOCUMENTS

JP 02-100682 A * 12/1990
WO WO-2004060278 A2 * 7/2004 ............ C12Q 1/689

OTHER PUBLICATIONS

Dasgupta (Mongabay news (2016) pp. 1-6).*
Sanders (Futurity (2012) pp. 1-14).*
Guiry (J Phycol (2012) vol. 48, pp. 1057-1063).*
GenBank: AF277331.1 (https://www.ncbi.nlm.nih.gov/nuccore/af277331, May 10, 2002).*
Phipps (J Dairy Sciences (2003) vol. 86, pp. 4070-4078).*
Tanabe (PLOS one (2013) vol. 8, e 76910.*
Jane ( Molecular Ecology Resources (2015) pp. 216-227, epublished Jun. 13, 2014).*
Scriver (Aquatic Botany (2015) vol. 122, pp. 27-31).*
Goldberg (PLOS one (2011) vol. 6, e22746).*
GenBank: DQ087517.1(https://www.ncbi.nlm.nih.gov/nuccore/71063769?sat=46&satkey=24729600, Dec. 11, 2007).*
Diffenbach (PCR methods and Applications (1993) vol. 3, pp. S30-S37).*
Roux et al(PCR Methods and Applications (1995) vol. 4, pp. s185-s194).*
Turmel (Journal of Molecular biology (1993) vol. 232, pp. 446-467).*
Sugiura (Plant molecular Biology (1992) vol. 19, pp. 149-168).*
Riaz (Nucleic acid research (2011) vol. 21, e145).*
NCBI Blast (https://blast.ncbi.nlm.nih.gov/Blast.cgi, downloaded Mar. 4, 2019).*
Ravon (environmental DNA a review of the possible applications for the detection of (invasive) species (2014) pp. 1-111).*
Timmerman-Vaughan (Plant Molecular Biology Reporter (2005) vol. 23, pp. 77a-77n).*
Taberlet (Plant Molecular Biology (1991), vol. 17, pp. 1105-1109).*
Thomsen (Biological Conservation (2015) vol. 183, pp. 4-18).*
Murray (Food and environmental Virology (2013, vol. 5 pp. 61-68).*
Backer (Lake line (2012) vol. 32, pp. 7-9).*
Addy and Green (Natural Resources Facts (1996), fact sheet 96-4).*
GenBank Accession L42858.1 (Nov. 21, 2001) https://www.ncbi.nlm.nih.gov/nuccore/I42858.1).*
GenBank Accession AB001682 (https://www.ncbi.nlm.nih.gov/nuccore/2224352?sat=24&satkey=146458, Apr. 28, 2001).*
GenBank Accession FJ423446.1 (https://www.ncbi.nlm.nih.gov/nuccore/213517384?sat=46&satkey=25771387, Jun. 9, 2009).*
GenBank Accession AY958085 (https://www.ncbi.nlm.nih.gov/nuccore/61393539?sat=46&satkey=24585467, Dec. 5, 2008).*
Noble (Pestsmart The utility of eDNA as a tiplaia survielnance tool (2015).*
Hedman (Methods in Molecular Biology (2013), vol. 943, pp. 17-48).*
Holinger (2013) (water research (2014) vol. 49, pp. 225-2235).*
EPA (Quality Assurance/Quality Control Guidance for Laboratories Performing PCR Analyses on Environmental Samples)(2004).*
Carim et al., "An environmental DNA assay for detecting Arctic grayling in the upper Missouri River basin, North America," *Conservation Genet Resour.* 8:197-199, 2016.
Mühl et al., "Activity and DNA contamination of commercial polymerase chain reaction reagents for the universal 16S rDNA real-time polymerase chain reaction detection of bacterial pathogens in blood," *Diagn Microbiol Infect Dis.* 66:41-49, 2010.
Peterson et al., "Investigating the dispersal routes used by an invasive amphibian, *Lithobates catesbeianus*, in human-dominated landscapes," *Biol. Invasions* 15:2179-2191, 2013.

(Continued)

*Primary Examiner* — Steven Pohnert
(74) *Attorney, Agent, or Firm* — Klarquist Sparkman, LLP

(57) ABSTRACT

This application provides methods, kits, probes and primers, that can be used to analyze environmental samples, such as water samples, soil samples, and air samples. The methods and kits can include positive controls, to provide confidence in test results.

17 Claims, 20 Drawing Sheets

Specification includes a Sequence Listing.

(56) References Cited

OTHER PUBLICATIONS

Pilliod et al., "Estimating occupancy and abundance of stream amphibians using environmental DNA from filtered water samples," *Can J Fish Aquat Sci.* 70:1123-1130, 2013.
Pilliod et al., "Factors influencing detection of eDNA from a stream-dwelling amphibian," *Mol Ecol. Resources* 14:109-116, 2014.
Strickler et al., "Quantifying effects of UV-B, temperature, and pH on eDNA degradation in aquatic microcosms," *Biol Conserv.* 183:85-92, 2015.
Thomsen et al., "Monitoring endangered freshwater biodiversity using environmental DNA," *Mol Ecol.* 21:2565-2573, 2012.
Baird & Hajibabaei, "Biomonitoring 2.0: a new paradigm in ecosystem assessment made possible by next-generation DNA sequencing," *Mol Ecol.* 21:2039-2044, 2012.
Berthelot et al., "The rainbow trout genome provides novel insights into evolution after whole-genome duplication in vertebrates," *Nat Commun.* 5:3657, 2014.
Champlot et al., "An efficient multistrategy DNA decontamination procedure of PCR reagents for hypersensitive PCR applications," *PLoS One* 5:e13042, 2010.
Ficetola et al., "Species detection using environmental DNA from water samples," *Biol Lett.* 4:423-425, 2008.
Goldberg et al., "Molecular detection of vertebrates in stream water: a demonstration using Rocky Mountain tailed frogs and Idaho giant salamanders," *PLoS One* 6:e22746, 2011.
Goldberg et al., "Moving environmental DNA methods from concept to practice for monitoring aquatic macroorganisms," *Biol Conserv.* 183:1-3, 2015.
Goldberg et al., "Critical considerations for the application of environmental DNA methods to detect aquatic species," *Meth Ecol Evol.* 7:1299-1307, 2016.
Herder et al., "Environmental DNA—a review of the possible applications for the detection of (invasive) species," Nijmegen: Netherlands Food and Consumer Product Safety Authority, 2014.
Hobbs, "Environmental DNA Protocol for Reshwater aquatic Ecosystems Version 2.0," prepared for BC Ministry of Environment, May 2016, circulated Jun. 27, 2016.
Iulia et al., "The evidence of contaminant bacterial DNA in several commercial Taq polymerases," *Rom Biotechnol Lett.* 18:8007-8012, 2013.
Naccache et al., "The perils of pathogen discovery: origin of a novel parvovirus-like hybrid genome traced to nucleic acid extraction spin columns," *J Virol.* 87:11966-11977, 2013.
Orchard, "Update on bullfrog control program in the western communities control corridor," Victoria: Capitol Regional District, 16 pp, 2012.
Rees et al., "The detection of aquatic animal species using environmental DNA—a review of eDNA as a survey tool in ecology," *J Appl Ecol.* 51:1450-1459, 2014.
Somerville et al., "Simple, rapid method for direct isolation of nucleic acids from aquatic environments," *Appl Environ Microbiol.* 55:548-554, 1989.
Takahara et al., Using environmental DNA to estimate the distribution of an invasive fish species in ponds, *PLoS One* 8:e56584, 2013.
Thomsen & Willerslev, "Environmental DNA—An emerging tool in conservation for monitoring past and present biodiversity," *Biol Conserv.* 183:4-18, 2015.
Turner et al., "Fish environmental DNA is more concentrated in aquatic sediments than surface water," *Biol Conserv.* 183:93-102, 2015.
Wilcox et al., "Robust detection of rare species using environmental DNA: the importance of primer specificity," *PLoS One* 8:e59520, 2013.
Hobbs et al., "Expansion of the known distribution of the coastal tailed frog, *Ascaphus truei*, in British Columbia, Canada using robust eDNA detection methods," *PLoS One*, vol. 14 (No. 3): pp. 1-16 (2019).
Hobbs et al., "Revising the range of Rocky Mountain tailed frog, *Ascaphus montanus*, in British Columbia, Canada, using environmental DNA methods," *Environmental DNA*, vol. 2: pp. 350-361 (2020).
Veldhoen et al., "Implementation of Novel Design Features for qPCR-Based eDNA Assessment," *PLoS One*, vol. 11 (No. 11): pp. 1-23 (2016).
Boore, Jeffrey L., "Animal mitochondrial genomes," *Nucleic Acids Res.* 15;27(8):1767-80, 1999.
De Las Rivas et al., "Comparative Analysis of Chloroplast Genomes: Functional Annotation, Genome-Based Phylogeny, and Deduced Evolutionary Patterns," *Genome Res.* 12(4): 567-583, 2002.
Furlan and Gleeson, "Improving reliability in environmental DNA detection surveys through enhanced quality control," *Marine and Freshwater Research*, 68:388-395, 2017.
Hu et al., "A comparison of four methods for PCR inhibitor removal," *Forensic Sci Int Genet.*, 16:94-97, 2015 (Abstract only).

* cited by examiner

FIG. 9

Helbing Laboratory eDNA Technical Bulletin

All eDNA tools are validated through a rigorous multi-step evaluation protocol that includes tests of DNA target specificity and amplification sensitivity.

Bulletin Version : 92116

General eDNA Assay Information

Target Species : Various Frog Species
Species Abbreviation : Frog
eDNA qPCR Tool : eFrog3
eDNA qPCR Format : TaqMan eDNA Assay Specificity Tests

A. qPCR Activity : Multi-species analysis of eDNA tool efficacy (5 µg/L Total DNA)

Multiple qPCR reactions (n=25) performed per target DNA. Detection within the standardized eDNA qPCR assay = Yes

| ASMO | ASTR | ANBO-VI | LICA | LIPI | PSRE | RAAU | XELA | AMGR | PLVE | HOSA | NTC |
|---|---|---|---|---|---|---|---|---|---|---|---|
| Yes | Yes | Yes | Yes | Yes | Yes | Yes | No | No | No | No | No |

B. Confirmation of gene-specificity in eDNA assay : ☑
C. Field Validation Completed : ☐ eDNA Assay Sensitivity Test

| DNA (ug/L) | LICA used as the target total DNA | | ASMO used as the target total DNA | |
|---|---|---|---|---|
| | Detection Frequency (n=25) | Binomial Standard error (n=8) | Detection Frequency (n=25) | Binomial Standard error (n=8) |
| 5 | 1 | 0.000 | 1 | 0.000 |
| 1 | 1 | 0.000 | 1 | 0.000 |
| 0.2 | 0.72 | 0.159 | 0.84 | 0.130 |
| 0.04 | 0.16 | 0.130 | 0.32 | 0.165 |
| 0.008 | 0.04 | 0.069 | 0.08 | 0.096 |
| 0 | 0.04 | 0.069 | 0 | 0.000 |

Appendix: Abbreviations

| | | |
|---|---|---|
| Rocky Mountain Tailed Frog (*Ascaphus montanus*) | ASMO | |
| Western Toad (*Anaxyrus (Bufo) boreas*) | ANBO | Sourced from Vancouver Island (VI) |
| Bullfrog (*Lithobates (Rana) catesbeiana*) | LICA | |
| Norther Leopard Frog (*Lithobates (Rana) pipiens*) | LIPI | |
| Pacific Chorus Frog (*Pseudacris (Hyla) regilla*) | PSRE | |
| Northern Red-legged Frog (*Rana aurora*) | RAAU | |
| African Clawed Frog (*Xenopus laevis*) | XELA | |
| Northwestern Salamander (*Ambystoma gracile*) | AMGR | |
| Western Redback Salamander (*Plethodon vehiculum*) | PLVE | |
| Human (*Homo sapiens*) | HOSA | |
| qPCR no template control | NTC | |
| quantitative real-time polymerase chain reaction | qPCR | |
| environmental DNA | eDNA | |

FIG. 10

Helbing Laboratory eDNA Technical Bulletin

All eDNA tools are validated through a rigorous multi-step evaluation protocol that includes tests of DNA target specificity and amplification sensitivity.

Bulletin Version : 81716

General eDNA Assay Information

Target Species : Mammalian species
Species Abbreviation : eMammal
eDNA qPCR Tool : eMammal1
eDNA qPCR Format : TaqMan eDNA Assay Specificity Tests

A. qPCR Activity : Multi-species analysis of eDNA tool efficacy (5 μg/L Total DNA)

| Multiple qPCR reactions (n=25) performed per target DNA. Detection within the standardized eDNA qPCR assay = Yes | | | | | | | | | | |
|---|---|---|---|---|---|---|---|---|---|---|
| SOBE | SOCI | SOTR | URAM | ALAL | ODHE | CEEL | FECA | LICA | HOSA | NTC |
| Yes | Yes | Yes | Yes | Yes | Yes | Yes | Yes (50%)* | No | Yes (50%)* | No |

*Extremely weak signal under optimal conditions. Unlikely to contribute to a signal under field conditions.

B. Confirmation of gene-specificity in eDNA assay : ☑
C. Field Validation Completed : ☑ eDNA Assay Sensitivity Test

Total DNA used for this assay was ODHE

| DNA (ug/L) | Detection Frequency (n=25) | Binomial Standard error (n=8) |
|---|---|---|
| 5 | 1.00 | 0.00000 |
| 1 | 1.00 | 0.00000 |
| 0.2 | 0.88 | 0.11489 |
| 0.04 | 0.56 | 0.17550 |
| 0.008 | 0.20 | 0.14142 |
| 0 | 0.00 | 0.00000 |

Appendix: Abbreviations

| | | | |
|---|---|---|---|
| Pacific Water/Marsh Shrew | *Sorex bendirii* | SOBE | |
| Cinereus Shrew | *Sorex cinereus* | SOCI | Sourced from Vancouver Island (VI) |
| Trowbridge's Shrew | *Sorex trowbridgii* | SOTR | |
| American Black Bear | *Ursus americanus* | URAM | |
| Moose | *Alces alces* | ALAL | |
| Black Tailed Deer | *Odocoileus hemionus* | ODHE | |
| Elk | *Cervus elaphus* | CEEL | |
| Cat | *Felis catus* | FECA | |
| Bullfrog | *Lithobates (Rana) catesbeiana* | LICA | |
| Human | *Homo sapiens* | HOSA | |
| qPCR no template control | | NTC | |
| quantitative real-time polymerase chain reaction | | qPCR | |
| environmental DNA | | eDNA | |

FIG. 11

Helbing Laboratory eDNA Technical Bulletin

All eDNA tools are validated through a rigorous multi-step evaluation protocol that includes tests of DNA target specificity and amplification sensitivity.

General eDNA Assay Information

| | |
|---|---|
| Target Species : | Western Toad (*Anaxyrus (Bufo) boreas*) |
| Species Abbreviation : | ANBO |
| eDNA qPCR Tool : | eANBO4 |
| eDNA qPCR Format : | TaqMan |

eDNA Assay Specificity Tests

A. qPCR Activity : Multi-species analysis of eDNA tool efficacy

Multiple qPCR reactions (n=25) performed per target DNA. Detection within the standardized eDNA qPCR assay = Yes

| ASMO | ANBO-VI | LICA | PSRE | RAAU | RAPR | TAGR | HOSA | NTC | | |
|---|---|---|---|---|---|---|---|---|---|---|
| No | Yes | No | No | No | No | No | No | No | | |

B. Confirmation of gene-specificity in eDNA assay : Confirmed eDNA Assay Sensitivity Test

| DNA (ug/L) | Detection Frequency (n=25) | Binomial Standard error (n=8) |
|---|---|---|
| 5 | 100 | 0.00 |
| 1 | 100 | 0.00 |
| 0.2 | 100 | 0.00 |
| 0.04 | 92 | 0.10 |
| 0.008 | 52 | 0.18 |
| 0 | 0 | 0.00 |

Appendix: Abbreviations

| | | |
|---|---|---|
| Rocky Mountain Tailed Frog (*Ascaphus montanus*) | ASMO | |
| Western Toad (*Anaxyrus (Bufo) boreas*) | ANBO-VI | Sourced from Vancouver Island (VI) |
| Bullfrog (*Lithobates (Rana) catesbeiana*) | LICA | |
| Pacific Chorus Frog (*Pseudacris (Hyla) regilla*) | PSRE | |
| Northern Red-legged Frog (*Rana aurora*) | RAAU | |
| Oregon Spotted Frog (*Rana pretiosa*) | RAPR | |
| Rough-skinned Newt (*Taricha granulosa*) | TAGR | |
| Human (*Homo sapiens*) | HOSA | |
| qPCR no template control | NTC | |
| quantitative real-time polymerase chain reaction | qPCR | |
| environmental DNA | eDNA | |

FIG. 12

Helbing Laboratory eDNA Technical Bulletin

All eDNA tools are validated through a rigorous multi-step evaluation protocol that includes tests of DNA target specificity and amplification sensitivity.

Bulletin Version : 81716

General eDNA Assay Information

Target Species : Rocky Mountain Tailed Frog (*Ascaphus montanus*)

Species Abbreviation : ASMO eDNA qPCR Tool : eASMO8 eDNA qPCR Format : TaqMan eDNA Assay Specificity Tests

A. qPCR Activity : Multi-species analysis of eDNA tool efficacy

Multiple qPCR reactions (n=25) performed per target DNA. Detection within the standardized eDNA qPCR assay = Yes

| ASMO | LICA | LIPI | PSRE | XELA | HOSA | NTC | | | | |
|---|---|---|---|---|---|---|---|---|---|---|
| Yes | No | No | No | No | No | No | | | | |

B. Confirmation of gene-specificity in eDNA assay : ☐

C. Field Validation Completed : ☐ eDNA Assay Sensitivity Test

| DNA (ug/L) | Detection Frequency (n=25) | Binomial Standard error (n=8) |
|---|---|---|
| 5 | 1.00 | 0.0000 |
| 1 | 1.00 | 0.0000 |
| 0.2 | 1.00 | 0.0000 |
| 0.04 | 0.78 | 0.1458 |
| 0.008 | 0.61 | 0.1725 |
| 0 | 0.00 | 0.0000 |

Appendix: Abbreviations

| | |
|---|---|
| Rocky Mountain Tailed Frog (*Ascaphus montanus*) | ASMO |
| Bullfrog (*Lithobates (Rana) catesbeiana*) | LICA |
| Norther Leopard Frog (*Lithobates (Rana) pipiens*) | LIPI |
| Pacific Chorus Frog (*Pseudacris (Hyla) regilla*) | PSRE |
| African Clawed Frog (*Xenopus laevis*) | XELA |
| Human (*Homo sapiens*) | HOSA |
| qPCR no template control | NTC |
| quantitative real-time polymerase chain reaction | qPCR |
| environmental DNA | eDNA |

FIG. 13

Helbing Laboratory eDNA Technical Bulletin

All eDNA tools are validated through a rigorous multi-step evaluation protocol that includes tests of DNA target specificity and amplification sensitivity.

Bulletin Version: 81716

General eDNA Assay Information

Target Species : Pacific (Coastal) Tailed Frog (*Ascaphus truei*)
Species Abbreviation : ASTR
eDNA qPCR Tool : eASTRA
eDNA qPCR Format : TaqMan eDNA Assay Specificity Tests

A. qPCR Activity : Multi-species analysis of eDNA tool efficacy

Multiple qPCR reactions (n=25) performed per target DNA. Detection within the standardized eDNA qPCR assay = Yes

| ASMO | ASTR | ANBO-VI | LICA | PSRE | RAAU | RALU | XELA | TAGR | HOSA | NTC |
|---|---|---|---|---|---|---|---|---|---|---|
| No | Yes | No | No | No | No | No | No | No | No | No |

B. Confirmation of gene-specificity in eDNA assay : ☑
C. Field Validation Completed : ☐ eDNA Assay Sensitivity Test

| DNA (ug/L) | Detection Frequency (n=25) | Binomial Standard error (n=8) |
|---|---|---|
| 5 | 1 | 0.00 |
| 1 | 1 | 0.00 |
| 0.2 | 0.96 | 0.07 |
| 0.04 | 0.64 | 0.17 |
| 0.008 | 0.32 | 0.16 |
| 0 | 0 | 0.00 |

Appendix: Abbreviations

| | | |
|---|---|---|
| Rocky Mountain Tailed Frog (*Ascaphus montanus*) | ASMO | |
| Pacific (Coastal) Tailed Frog (*Ascaphus truei*) | ASTR | |
| Western Toad (*Anaxyrus (Bufo) boreas*) | ANBO-VI | Sourced from Vancouver Island (VI) |
| Bullfrog (*Lithobates (Rana) catesbeiana*) | LICA | |
| Pacific Chorus Frog (*Pseudacris (Hyla) regilla*) | PSRE | |
| Northern Red-legged Frog (*Rana aurora*) | RAAU | |
| Columbia Spotted Frog (*Rana luteiventris*) | RALU | |
| African Clawed Frog (*Xenopus laevis*) | XELA | |
| Rough-skinned Newt (*Taricha granulosa*) | TAGR | |
| Human (*Homo sapiens*) | HOSA | |
| qPCR no template control | NTC | |
| quantitative real-time polymerase chain reaction | qPCR | |
| environmental DNA | eDNA | |

FIG. 14

Helbing Laboratory eDNA Technical Bulletin

All eDNA tools are validated through a rigorous multi-step evaluation protocol that includes tests of DNA target specificity and amplification sensitivity.

Bulletin Version : 81716

General eDNA Assay Information

Target Species : American Bullfrog (*Lithobates (Rana) catesbeiana* )

Species Abbreviation : LICA eDNA qPCR Tool : eLICA1 eDNA qPCR Format : TaqMan eDNA Assay Specificity Tests

A. qPCR Activity : Multi-species analysis of eDNA tool efficacy

Multiple qPCR reactions (n=25) performed per target DNA. Detection within the standardized eDNA qPCR assay = Yes

| ASMO | LICA | LIPI | PSRE | XELA | HOSA | NTC | | | | |
|---|---|---|---|---|---|---|---|---|---|---|
| No | Yes | No | No | No | No | No | | | | |

B. Confirmation of gene-specificity in eDNA assay : ☑

C. Field Validation Completed : ☑ eDNA Assay Sensitivity Test

| DNA (ug/L) | Detection Frequency (n=25) | Binomial Standard error (n=8) |
|---|---|---|
| 5 | 1.00 | 0.0000 |
| 1 | 0.96 | 0.0693 |
| 0.2 | 0.52 | 0.1766 |
| 0.04 | 0.16 | 0.1296 |
| 0.008 | 0.08 | 0.0959 |
| 0 | 0.00 | 0.0000 |

Appendix: Abbreviations

| | |
|---|---|
| Rocky Mountain Tailed Frog (*Ascaphus montanus* ) | ASMO |
| Bullfrog (*Lithobates (Rana) catesbeiana* ) | LICA |
| Norther Leopard Frog (*Lithobates (Rana) pipiens*) | LIPI |
| Pacific Chorus Frog (*Pseudacris (Hyla) regilla* ) | PSRE |
| African Clawed Frog (*Xenopus laevis* ) | XELA |
| Human (*Homo sapiens* ) | HOSA |
| qPCR no template control | NTC |
| quantitative real-time polymerase chain reaction | qPCR |
| environmental DNA | eDNA |

FIG. 15

Helbing Laboratory eDNA Technical Bulletin

All eDNA tools are validated through a rigorous multi-step evaluation protocol that includes tests of DNA target specificity and amplification sensitivity.

Bulletin Version : 81716

General eDNA Assay Information

Target Species : Northern Leopard Frog (*Lithobates(Rana) pipiens*

Species Abbreviation : LIPI eDNA qPCR Tool : eLIPI1 eDNA qPCR Format : TaqMan eDNA Assay Specificity Tests

A. qPCR Activity : Multi-species analysis of eDNA tool efficacy (5 μg/L Total DNA)

Multiple qPCR reactions (n=25) performed per target DNA. Detection within the standardized eDNA qPCR assay = Yes

| ASTR | ANBO-VI | LICA | LICL | LIPI | PSRE | RAAU | XELA | TAGR | HOSA | NTC |
|---|---|---|---|---|---|---|---|---|---|---|
| No | No | No | No | Yes | No | No | No | No | No | No |

B. Confirmation of gene-specificity in eDNA assay : ☐

C. Field Validation Completed : ☐ eDNA Assay Sensitivity Test

| DNA (μg/L) | Detection Frequency (n=25) | Binomial Standard error (n=8) |
|---|---|---|
| 5 | 0.84 | 0.12961 |
| 1 | 0.96 | 0.06928 |
| 0.2 | 0.32 | 0.16492 |
| 0.04 | 0 | 0.00000 |
| 0.008 | 0 | 0.00000 |
| 0 | 0 | 0.00000 |

Appendix: Abbreviations

| | | |
|---|---|---|
| Pacific (Coastal) Tailed Frog (*Ascaphus truei*) | ASTR | |
| Western Toad (*Anaxyrus (Bufo) boreas*) | ANBO-VI | Sourced from Vancouver Island (VI) |
| Bullfrog (*Lithobates (Rana) catesbeiana*) | LICA | |
| Green Frog (*Lithobates (Rana) clamitans*) | LICL | |
| Northern Leopard Frog (*Lithobates(Rana) pipiens* | LIPI | |
| Pacific Chorus Frog (*Pseudacris (Hyla) regilla*) | PSRE | |
| Northern Red-legged Frog (*Rana aurora*) | RAAU | |
| African Clawed Frog (*Xenopus laevis*) | XELA | |
| Rough-skinned Newt (*Taricha granulosa*) | TAGR | |
| Human (*Homo sapiens*) | HOSA | |
| qPCR no template control | NTC | |
| quantitative real-time polymerase chain reaction | qPCR | |
| environmental DNA | eDNA | |

FIG. 16

Helbing Laboratory eDNA Technical Bulletin

All eDNA tools are validated through a rigorous multi-step evaluation protocol that includes tests of DNA target specificity and amplification sensitivity.

General eDNA Assay Information

Target Species : Northern Red-legged Frog (*Rana aurora*)
Species Abbreviation : RAAU
eDNA qPCR Tool : eRAAU1
eDNA qPCR Format : TaqMan eDNA Assay Specificity Tests

A. qPCR Activity : Multi-species analysis of eDNA tool efficacy

| Multiple qPCR reactions (n=25) performed per target DNA. Detection within the standardized eDNA qPCR assay = Yes | | | | | | | | | | |
|---|---|---|---|---|---|---|---|---|---|---|
| ASMO | ANBO-VI | LICA | PSRE | RAAU | RAPR | RACA | RALU | TAGR | HOSA | NTC |
| No | No | No | No | Yes | No | No | No | No | No | No |

B. Confirmation of gene-specificity in eDNA assay : Confirmed eDNA Assay Sensitivity Test

| DNA (ug/L) | Detection Frequency (n=25) | Binomial Standard error (n=8) |
|---|---|---|
| 5 | 1 | 0.00 |
| 1 | 0.88 | 0.11 |
| 0.2 | 0.4 | 0.17 |
| 0.04 | 0.2 | 0.14 |
| 0.008 | 0.28 | 0.16 |
| 0 | 0 | 0.00 |

Appendix: Abbreviations

| | | |
|---|---|---|
| Rocky Mountain Tailed Frog (*Ascaphus montanus*) | ASMO | |
| Western Toad (*Anaxyrus (Bufo) boreas*) | ANBO-VI | Sourced from Vancouver Island (VI) |
| Bullfrog (*Lithobates (Rana) catesbeiana*) | LICA | |
| Pacific Chorus Frog (*Pseudacris (Hyla) regilla*) | PSRE | |
| Northern Red-legged Frog (*Rana aurora*) | RAAU | |
| Oregon Spotted Frog (*Rana pretiosa*) | RAPR | |
| Cascades Frog (*Rana cascadae*) | RACA | |
| Columbia Spotted Frog (*Rana luteiventris*) | RALU | |
| Rough-skinned Newt (*Taricha granulosa*) | TAGR | |
| Human (*Homo sapiens*) | HOSA | |
| qPCR no template control | NTC | |
| quantitative real-time polymerase chain reaction | qPCR | |
| environmental DNA | eDNA | |

FIG. 17

Helbing Laboratory eDNA Technical Bulletin

All eDNA tools are validated through a rigorous multi-step evaluation protocol that includes tests of DNA target specificity and amplification sensitivity.

General eDNA Assay Information

Target Species : Cascades Frog (*Rana cascadae*)
Species Abbreviation : RACA
eDNA qPCR Tool : eRACA2
eDNA qPCR Format : TaqMan eDNA Assay Specificity Tests

A. qPCR Activity : Multi-species analysis of eDNA tool efficacy

Multiple qPCR reactions (n=25) performed per target DNA. Detection within the standardized eDNA qPCR assay = Yes

| ASMO | ANBO-VI | LICA | PSRE | RAAU | RAPR | RACA | RALU | TAGR | HOSA | NTC |
|---|---|---|---|---|---|---|---|---|---|---|
| No | No | No | No | No | No | Yes | No | No | No | No |

B. Confirmation of gene-specificity in eDNA assay : Confirmed eDNA Assay Sensitivity Test

| DNA (ug/L) | Detection Frequency (n=25) | Binomial Standard error (n=8) |
|---|---|---|
| 5 | 0.96 | 0.07 |
| 1 | 1 | 0.00 |
| 0.2 | 0.76 | 0.15 |
| 0.04 | 0.36 | 0.17 |
| 0.008 | 0.08 | 0.10 |
| 0 | 0 | 0.00 |

Appendix: Abbreviations

| | | |
|---|---|---|
| Rocky Mountain Tailed Frog (*Ascaphus montanus*) | ASMO | |
| Western Toad (*Anaxyrus (Bufo) boreas*) | ANBO-VI | Sourced from Vancouver Island (VI) |
| Bullfrog (*Lithobates (Rana) catesbeiana*) | LICA | |
| Pacific Chorus Frog (*Pseudacris (Hyla) regilla*) | PSRE | |
| Northern Red-legged Frog (*Rana aurora*) | RAAU | |
| Oregon Spotted Frog (*Rana pretiosa*) | RAPR | |
| Cascades Frog (*Rana cascadae*) | RACA | |
| Columbia Spotted Frog (*Rana luteiventris*) | RALU | |
| Rough-skinned Newt (*Taricha granulosa*) | TAGR | |
| Human (*Homo sapiens*) | HOSA | |
| qPCR no template control | NTC | |
| quantitative real-time polymerase chain reaction | qPCR | |
| environmental DNA | eDNA | |

FIG. 18

Helbing Laboratory eDNA Technical Bulletin

All eDNA tools are validated through a rigorous multi-step evaluation protocol that includes tests of DNA target specificity and amplification sensitivity.

General eDNA Assay Information

Target Species : Columbia Spotted Frog (*Rana luteiventris*)
Species Abbreviation : RALU
eDNA qPCR Tool : eRALU2
eDNA qPCR Format : TaqMan eDNA Assay Specificity Tests

A. qPCR Activity : Multi-species analysis of eDNA tool efficacy

| Multiple qPCR reactions (n=25) performed per target DNA. Detection within the standardized eDNA qPCR assay = Yes | | | | | | | | | | |
|---|---|---|---|---|---|---|---|---|---|---|
| ASMO | ANBO-VI | LICA | PSRE | RAAU | RAPR | RACA | RALU | TAGR | HOSA | NTC |
| No | No | No | No | No | No | No | Yes | No | No | No |

B. Confirmation of gene-specificity in eDNA assay : Confirmed eDNA Assay Sensitivity Test

| DNA (ug/L) | Detection Frequency (n=25) | Binomial Standard error (n=8) |
|---|---|---|
| 5 | 1 | 0.00 |
| 1 | 0.92 | 0.10 |
| 0.2 | 0.36 | 0.17 |
| 0.04 | 0.12 | 0.11 |
| 0.008 | 0 | 0.00 |
| 0 | 0 | 0.00 |

Appendix: Abbreviations

| | | |
|---|---|---|
| Rocky Mountain Tailed Frog (*Ascaphus montanus*) | ASMO | |
| Western Toad (*Anaxyrus (Bufo) boreas*) | ANBO-VI | Sourced from Vancouver Island (VI) |
| Bullfrog (*Lithobates (Rana) catesbeiana*) | LICA | |
| Pacific Chorus Frog (*Pseudacris (Hyla) regilla*) | PSRE | |
| Northern Red-legged Frog (*Rana aurora*) | RAAU | |
| Oregon Spotted Frog (*Rana pretiosa*) | RAPR | |
| Cascades Frog (*Rana cascadae*) | RACA | |
| Columbia Spotted Frog (*Rana luteiventris*) | RALU | |
| Rough-skinned Newt (*Taricha granulosa*) | TAGR | |
| Human (*Homo sapiens*) | HOSA | |
| qPCR no template control | NTC | |
| quantitative real-time polymerase chain reaction | qPCR | |
| environmental DNA | eDNA | |

FIG. 19

Helbing Laboratory eDNA Technical Bulletin

All eDNA tools are validated through a rigorous multi-step evaluation protocol that includes tests of DNA target specificity and amplification sensitivity.

General eDNA Assay Information

| | | |
|---|---|---|
| Target Species | : | Oregon Spotted Frog (*Rana pretiosa*) |
| Species Abbreviation | : | RAPR |
| eDNA qPCR Tool | : | eRAPR2 |
| eDNA qPCR Format | : | TaqMan |

eDNA Assay Specificity Tests

A. qPCR Activity : Multi-species analysis of eDNA tool efficacy

Multiple qPCR reactions (n=25) performed per target DNA. Detection within the standardized eDNA qPCR assay = Yes

| ASMO | ANBO-VI | LICA | PSRE | RAAU | RAPR | RACA | RALU | TAGR | HOSA | NTC |
|---|---|---|---|---|---|---|---|---|---|---|
| No | No | No | No | No | Yes | No | Yes | No | No | No |

B. Confirmation of gene-specificity in eDNA assay : Confirmed eDNA Assay Sensitivity Test

| DNA (ug/L) | Detection Frequency (n=25) | Binomial Standard error (n=8) |
|---|---|---|
| 5 | 1 | 0.00 |
| 1 | 1 | 0.07 |
| 0.2 | 0.76 | 0.18 |
| 0.04 | 0.44 | 0.13 |
| 0.008 | 0.12 | 0.10 |
| 0 | 0 | 0.00 |

Appendix: Abbreviations

| | | |
|---|---|---|
| Rocky Mountain Tailed Frog (*Ascaphus montanus*) | ASMO | |
| Western Toad (*Anaxyrus (Bufo) boreas*) | ANBO-VI | Sourced from Vancouver Island (VI) |
| Bullfrog (*Lithobates (Rana) catesbeiana*) | LICA | |
| Pacific Chorus Frog (*Pseudacris (Hyla) regilla*) | PSRE | |
| Northern Red-legged Frog (*Rana aurora*) | RAAU | |
| Oregon Spotted Frog (*Rana pretiosa*) | RAPR | |
| Cascades Frog (*Rana cascadae*) | RACA | |
| Columbia Spotted Frog (*Rana luteiventris*) | RALU | |
| Rough-skinned Newt (*Taricha granulosa*) | TAGR | |
| Human (*Homo sapiens*) | HOSA | |
| qPCR no template control | NTC | |
| quantitative real-time polymerase chain reaction | qPCR | |
| environmental DNA | eDNA | |

FIG. 20

Helbing Laboratory eDNA Technical Bulletin

All eDNA tools are validated through a rigorous multi-step evaluation protocol that includes tests of DNA target specificity and amplification sensitivity.

General eDNA Assay Information

| | | |
|---|---|---|
| Target Species | : | Pacific Water Shrew (*Sorex bendirii*) |
| Species Abbreviation | : | SOBE |
| eDNA qPCR Tool | : | eSOBE4 |
| eDNA qPCR Format | : | TaqMan |

eDNA Assay Specificity Tests

A. qPCR Activity : Multi-species analysis of eDNA tool efficacy

Multiple qPCR reactions (n=25) performed per target DNA. Detection within the standardized eDNA qPCR assay = Yes

| SOBE | SOCI | SOMO | SONA | SOPA | SORO | SOTR | SOVA | ODHE | HOSA | NTC |
|---|---|---|---|---|---|---|---|---|---|---|
| Yes | No | Yes (50%)* | No | Yes* | No | No | No | No | No | No |

*Substantially weaker detection ability than SOBE. Unlikely to provide signal in the field.

B. Confirmation of gene-specificity in eDNA assay : Confirmed eDNA Assay Sensitivity Test

| DNA (ug/L) | Detection Frequency (n=25) | Binomial Standard error (n=8) |
|---|---|---|
| 5 | 1 | 0.00 |
| 1 | 1 | 0.10 |
| 0.2 | 0.76 | 0.150997 |
| 0.04 | 0.28 | 0.158745 |
| 0.008 | 0 | 0.00 |
| 0 | 0 | 0.00 |

Appendix: Abbreviations

| | | |
|---|---|---|
| Pacific Water Shrew | *Sorex bendirii* | SOBE |
| Cinereus Shrew | *Sorex cinereus* | SOCI |
| Merriam's Shrew | *Sorex merriami* | SOMO |
| Dusky/Montane Shrew | *Sorex monticolus* | SONA |
| American Water Shrew | *Sorex palustris* | SOPA |
| Olympic Shrew | *Sorex rohweri* | SORO |
| Trowbridge's Shrew | *Sorex trowbridgii* | SOTR |
| Vagrant Shrew | *Sorex vagrans* | SOVA |
| Mule Deer | *Odocoileus hemionus* | ODHE |
| Human | *Homo sapiens* | HOSA |
| qPCR no template control | | NTC |
| quantitative real-time polymerase chain reaction | | qPCR |
| environmental DNA | | eDNA |

QUANTITATIVE PCR-BASED ENVIRONMENTAL DNA ASSAYS

CROSS REFERENCE TO RELATED APPLICATIONS

This application claims priority to U.S. Provisional Application No. 62/406,802 filed Oct. 11, 2016, and Canadian Application No. 2,964,374, both herein incorporated by reference.

FIELD

This application provides methods, kits, probes, and primers, which can be used to analyze environmental samples.

BACKGROUND

In the realm of environmental science, an understanding that genetic material can be harvested from ecosystem biota has been known for decades [1]. Recent technical advances in polymerase chain reaction (PCR) or its variation, quantitative real-time PCR (qPCR), now allow for the successful detection of minute amounts of species-specific nuclear or mitochondrial DNA material in collected aquatic, terrestrial (including air), or sediment field samples with the application of qPCR methodology [2-6]. Such analysis of 'environmental DNA' or eDNA is being used to augment traditional field survey techniques of macrobiota and often allows for increased accuracy in our understanding of native or introduced species. These methods can be used to efficiently refine existing information pertinent to conservation biology, dispersal of invasive species, and management of industrial impacts on the environment [7-11]. This method is cost-effective, non-invasive to the organism and habitat, and can be highly sensitive in a wide range of habitats. This is particularly invaluable relative to traditional survey techniques for rare or elusive species which are often labour-intensive and inefficient, and destructive to organismal habitats.

In contrast, eDNA can be measured from a simple water sample without disturbing the species of interest which is then filtered. DNA is then isolated from the filter and analyzed using qPCR methods. Because of its sensitivity, eDNA methods are best used for target species that are present at low density exactly under those conditions where traditional methods are least effective. eDNA methods provide the ability to archive samples indefinitely and query them multiple times for species of interest as need arises.

Due to its powerful sensitivity, establishment of appropriate rigour in the design and performance of the eDNA assay must be maintained to reduce the likelihood of false positive and negative results (i.e., Type 1 and Type 2 errors, respectively) that could impact the quality of management decisions based upon, for example, the successful eradication of invasive species or determination of presence or absence of endangered species. Considerable effort has been applied to critical aspects in the design and execution of eDNA methods [12]. The greatest concentrated effort has been focused upon methods pertaining to sample collection in the field, DNA extraction, and issues regarding data interpretation pertaining to eDNA distribution and dynamics in the environment. However, comparatively little detailed attention and clarity has been given to the actual qPCR assay design.

Detection of eDNA relies completely upon the qPCR assay which is often pushed to the limit in specificity and sensitivity requirements. The approach that has been taken to date [12] has focused upon development of species-specific primer sets through three design steps: 1) in silico, 2) in vitro, and 3) in situ. In silico design involves computer-based alignment of known DNA sequences from target and non-target species (when known) to identify regions that may represent discriminatory priming locations for qPCR-based detection of the target species. Selected primer set candidates are then tested on DNA from target and non-target species in vitro to evaluate assay specificity. Finally, in situ verification involves applying the primer set candidates that have passed the in vitro design step to eDNA samples obtained from environments with confirmed presence and absence of the target species. This latter step should be incorporated in every eDNA study as assay controls.

Despite acknowledgement of these important qPCR assay design aspects, there remains limited clarity on other important design, validation, and execution criteria that must be considered as they greatly influence the interpretive power of the qPCR portion of the eDNA assay. These include: explicitly designing and testing qPCR assays against detection of human DNA that may be introduced at the sampling and/or analysis stages; additional aspects of primer and probe design considerations; qPCR run conditions to enhance specificity based upon biochemical principles; the ability to distinguish between true and false negatives through evaluation of endogenous DNA found in all field-collected eDNA samples rather than through the laboratory-based practice of spiking samples with an external DNA template; and, the ability to enhance confidence in the assay result through the use of an animal group-based qPCR assay.

SUMMARY

The disclosure provides kits and methods for analyzing samples, as well as probes and primers that can be included in such kits and used in such methods.

In some examples, the kit includes (1) a forward and reverse primer set specific for plant chloroplast DNA, algae chloroplast DNA, fungal mitochondrial DNA or both plant chloroplast and algae chloroplast DNA, (2) a labeled nucleic acid probe specific for the plant chloroplast DNA, algae chloroplast DNA, fungal mitochondrial DNA or both plant chloroplast and algae chloroplast DNA, (3) a forward and reverse primer set specific for an animal group DNA, and/or a forward and a reverse primer set specific for an animal species DNA and (4) a labeled nucleic acid probe specific for the animal group DNA and/or a labeled nucleic acid probe specific for the animal species DNA, wherein none of the forward and reverse primer sets are capable of amplifying human DNA and wherein none of the labeled nucleic acid probes are capable of hybridizing to human DNA, for example under stringent conditions. In some examples, the kit further includes one or more of (such as 2, 3, or 4 of), a membrane filter, container for holding or collecting an environmental sample, reagents for isolating DNA (such as ethanol), reagents for qPCR (such as DNA polymerase, dNTPs, and/or $MgCl_2$), and a protease (such as proteinase K).

Methods for analyzing nucleic acid molecules (e.g., DNA) in a sample, such as an environmental sample, for example a fresh water sample, salt water sample, air sample, or soil sample, are provided. Such methods can include contacting nucleic acid molecules in the sample with (1) a forward and reverse primer set specific for plant chloroplast DNA, algae chloroplast DNA, fungal mitochondrial DNA or both plant chloroplast and algae chloroplast DNA, and (2) a forward and reverse primer set specific for an animal group DNA and/or a primer set specific for an animal species DNA. The nucleic acid molecules in the sample are amplified, for example using quantitative real-time PCR (qPCR), thereby generating amplicons. The method then includes identifying the nucleic acid molecules in the sample. Such methods can further include filtering the sample; and/or isolating nucleic acid molecules from the sample prior to the contacting step. In some examples, the method further includes contacting the sample or the amplicons with (1) a labeled nucleic acid probe specific for the plant chloroplast DNA, algae chloroplast DNA, fungal mitochondrial DNA or both plant chloroplast and algae chloroplast DNA; and (2) a labeled nucleic acid probe specific for the animal group DNA and/or a labeled nucleic acid probe specific for the animal species DNA, wherein none of the probes are capable of hybridizing to human DNA, for example under stringent conditions.

The forward and reverse primer set specific for animal group DNA is specific for a plurality of different animals in the same Class, Order, Family, or Genus. In one example, the forward and reverse primer set specific for the animal group DNA is specific for a plurality of mammals, amphibians, fish, or invertebrates, such as a plurality of frogs. In some examples, the forward and reverse primer set specific for the animal species DNA is specific for one or up to two or up to three or up to four species of mammal, amphibian, fish, or invertebrate. In some examples, the forward and reverse primer set specific for the animal species DNA is specific for: *Anaxyrus* (*Bufo*) *boreas* (Western toad), *Ascaphus montanus* (Rocky Mountain tailed frog), *Ascaphus truei* (Pacific (Coastal) tailed frog), *Lithobates* (*Rana*) *catesbeiana* (North American bullfrog), *Lithobates pipiens* (Northern leopard frog), *Rana aurora* (Northern red-legged frog), *Rana cascadae* (Cascades frog), *Rana luteiventris* (Columbia spotted frog), *Rana pretiosa* (Oregon spotted frog), *Sorex bendirii* (Pacific water shrew), *Lithobates* (*Rana*) *sylvaticus* (Wood frog), *Cottus cognatus* (Slimy Sculpin), *Prosopium cylindraceum* (Round Whitefish), *Salvelinus malma* (Dolly Varden), *Thymallus arcticus* (Arctic Grayling), *Oncorhynchus tschawytscha* (Chinook Salmon), *Oncorhynchus kisutch* (Coho Salmon), or *Dicamptodon tenebrosus* (Giant Pacific Salamander) (also see Table 7). In some examples, the forward and reverse primer set specific for the animal group DNA is capable of amplifying animal mitochondrial DNA.

The foregoing and other objects and feature of the disclosure will become more apparent from the following detailed description, which proceeds with reference to the accompanying figures.

BRIEF DESCRIPTION OF THE DRAWINGS

FIGS. 9-20 are technical bulletins that outline the performance characteristics of some exemplary animal group and species-specific primer and probe combinations. The eDNA Assay Specificity Test follows the schema as presented in FIGS. 2A-2B and 3, and was performed using 25 TaqMan®-based qPCR replicate reactions using 5 μg/L of purified total DNA from the indicated species to confirm specificity in the eDNA assay or no DNA added as a negative control (NTC). The species tested are listed in the abbreviations section at the bottom of the bulletin. Successful field validation using filter samples from known species-positive sites is indicated where data is available. The eDNA Assay Sensitivity Test follows the schema as presented in FIGS. 4A-4B and was comprised of 25 TaqMan®-based qPCR replicate reactions using a species-matched dilution series of total DNA (0.008-5 μg/L) and the frequency of detection indicated as defined by obtaining a specific amplification signal by 50 cycles. Binomial standard errors associated with the input DNA amounts are shown as calculated in FIGS. 5A-5B.

SEQUENCE LISTING

Figure 1:
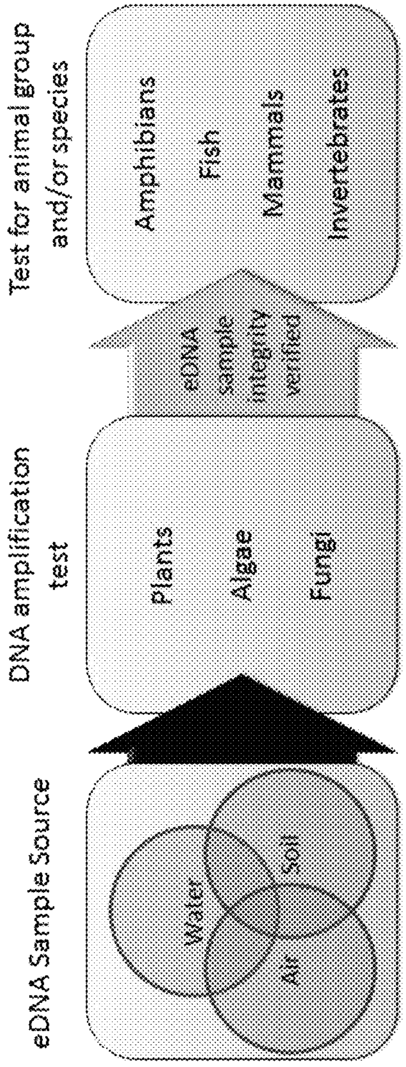
FIG. 1 is a schematic drawing showing an exemplary method where eDNA (from environmental samples) is amplified using primers specific for plants, algae and/or fungi as a positive control and the subsequent analysis for animal group or species DNA.

The nucleic acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. All strands are shown 5' to 3' unless otherwise indicated. The sequence listing entitled "sequence listing", generated on Oct. 2, 2017, 24 kb is filed herewith and incorporated by reference.

SEQ ID NO: 1 is an exemplary forward primer to amplify plant chloroplast 23S rRNA.

SEQ ID NO: 2 is an exemplary reverse primer to amplify plant chloroplast 23S rRNA.

SEQ ID NO: 3 is an exemplary probe to detect plant chloroplast 23S rRNA.

SEQ ID NO: 4 is an exemplary forward primer to amplify frog mitochondrial 12S rRNA.

SEQ ID NO: 5 is an exemplary reverse primer to amplify frog mitochondrial 12S rRNA.

SEQ ID NO: 6 is an exemplary probe to detect frog mitochondrial 12S rRNA.

SEQ ID NO: 7 is an exemplary forward primer to amplify frog mitochondrial 16S rRNA.

SEQ ID NO: 8 is an exemplary reverse primer to amplify frog mitochondrial 16S rRNA.

SEQ ID NO: 9 is an exemplary probe to detect frog mitochondrial 16S rRNA.

SEQ ID NO: 10 is an exemplary forward primer to amplify frog mitochondrial 16S rRNA.

SEQ ID NO: 11 is an exemplary reverse primer to amplify frog mitochondrial 16S rRNA.

SEQ ID NO: 12 is an exemplary probe to detect frog mitochondrial 16S rRNA.

SEQ ID NO: 13 is an exemplary forward primer to amplify bullfrog mitochondrial cytochrome B.

SEQ ID NO: 14 is an exemplary reverse primer to amplify bullfrog mitochondrial cytochrome B.

SEQ ID NO: 15 is an exemplary probe to detect bullfrog mitochondrial cytochrome B.

SEQ ID NO: 16 is an exemplary forward primer to amplify bullfrog mitochondrial 12S rRNA.

SEQ ID NO: 17 is an exemplary reverse primer to amplify bullfrog mitochondrial 12S rRNA.

SEQ ID NO: 18 is an exemplary probe to detect bullfrog mitochondrial 12S rRNA.

SEQ ID NO: 19 is an exemplary forward primer to amplify tailed frog mitochondrial cytochrome B.

SEQ ID NO: 20 is an exemplary reverse primer to amplify tailed frog mitochondrial cytochrome B.

SEQ ID NO: 21 is an exemplary probe to detect tailed frog mitochondrial cytochrome B.

SEQ ID NO: 22 is an exemplary forward primer to amplify tailed frog mitochondrial cytochrome B.

SEQ ID NO: 23 is an exemplary reverse primer to amplify tailed frog mitochondrial cytochrome B.

SEQ ID NO: 24 is an exemplary probe to detect tailed frog mitochondrial cytochrome B.

SEQ ID NO: 25 is an exemplary forward primer to amplify mammalian (but not human) MT-RNR1.

SEQ ID NO: 26 is an exemplary reverse primer to amplify mammalian (but not human) MT-RNR1.

SEQ ID NO: 27 is an exemplary probe to detect mammalian (but not human) MT-RNR1.

SEQ ID NO: 28 is an exemplary forward primer to amplify Western toad MT-CYB.

SEQ ID NO: 29 is an exemplary reverse primer to amplify Western toad MT-CYB.

SEQ ID NO: 30 is an exemplary probe to detect Western toad MT-CYB.

SEQ ID NO: 31 is an exemplary forward primer to amplify Rocky Mountain tailed frog MT-CYB.

SEQ ID NO: 32 is an exemplary reverse primer to amplify Rocky Mountain tailed frog MT-CYB.

SEQ ID NO: 33 is an exemplary probe to detect Rocky Mountain tailed frog MT-CYB.

SEQ ID NO: 34 is an exemplary forward primer to amplify Northern leopard frog MT-RNR1.

SEQ ID NO: 35 is an exemplary reverse primer to amplify Northern leopard frog MT-RNR1.

SEQ ID NO: 36 is an exemplary probe to detect Northern leopard frog MT-RNR1.

SEQ ID NO: 37 is an exemplary forward primer to amplify Northern red-legged frog MT-RNR2.

SEQ ID NO: 38 is an exemplary reverse primer to amplify Northern red-legged frog MT-RNR2.

SEQ ID NO: 39 is an exemplary probe to detect Northern red-legged frog MT-RNR2.

SEQ ID NO: 40 is an exemplary forward primer to amplify Cascades frog MT-CYB.

SEQ ID NO: 41 is an exemplary reverse primer to amplify Cascades frog MT-CYB.

SEQ ID NO: 42 is an exemplary probe to detect Cascades frog MT-CYB.

SEQ ID NO: 43 is an exemplary forward primer to amplify Columbia spotted frog MT-NDI.

SEQ ID NO: 44 is an exemplary reverse primer to amplify Columbia spotted frog MT-NDI.

SEQ ID NO: 45 is an exemplary probe to detect Columbia spotted frog MT-NDI.

SEQ ID NO: 46 is an exemplary forward primer to amplify Oregon spotted frog MT-CYB.

SEQ ID NO: 47 is an exemplary reverse primer to amplify Oregon spotted frog MT-CYB.

SEQ ID NO: 48 is an exemplary probe to detect Oregon spotted frog MT-CYB.

SEQ ID NO: 49 is an exemplary forward primer to amplify Pacific water shrew MT-CYB.

SEQ ID NO: 50 is an exemplary reverse primer to amplify Pacific water shrew MT-CYB.

SEQ ID NO: 51 is an exemplary probe to detect Pacific water shrew MT-CYB.

SEQ ID NO: 52 is an exemplary forward primer to amplify Pan amphibian MT-RNR2.

SEQ ID NO: 53 is an exemplary reverse primer to amplify Pan amphibian MT-RNR2.

SEQ ID NO: 54 is an exemplary probe to detect Pan amphibian MT-RNR2.

SEQ ID NO: 55 is an exemplary forward primer to amplify Pan fish MT-RNR1.

SEQ ID NO: 56 is an exemplary reverse primer to amplify Pan fish MT-RNR1.

SEQ ID NO: 57 is an exemplary probe to detect Pan fish MT-RNR1.

SEQ ID NO: 58 is an exemplary forward primer to amplify Pan fungus MT-CYB.

SEQ ID NO: 59 is an exemplary reverse primer to amplify Pan fungus MT-CYB.

SEQ ID NO: 60 is an exemplary probe to detect Pan fungus MT-CYB.

SEQ ID NO: 61 is an exemplary forward primer to amplify Pan fungus MT-CYB.

SEQ ID NO: 62 is an exemplary reverse primer to amplify Pan fungus MT-CYB.

SEQ ID NO: 63 is an exemplary probe to detect Pan fungus MT-CYB.

SEQ ID NO: 64 is an exemplary forward primer to amplify wood frog MT-CYB.

SEQ ID NO: 65 is an exemplary reverse primer to amplify wood frog MT-CYB.

SEQ ID NO: 66 is an exemplary probe to detect wood frog MT-CYB.

SEQ ID NO: 67 is an exemplary forward primer to amplify Slimy Sculpin MT-RNR1.

SEQ ID NO: 68 is an exemplary reverse primer to amplify Slimy Sculpin MT-RNR1.

SEQ ID NO: 69 is an exemplary probe to detect Slimy Sculpin MT-RNR1.

SEQ ID NO: 70 is an exemplary forward primer to amplify Slimy Sculpin MT-CYB.

SEQ ID NO: 71 is an exemplary reverse primer to amplify Slimy Sculpin MT-CYB.

SEQ ID NO: 72 is an exemplary probe to detect Slimy Sculpin MT-CYB.

SEQ ID NO: 73 is an exemplary forward primer to amplify Slimy Sculpin MT-CYB.

SEQ ID NO: 74 is an exemplary reverse primer to amplify Slimy Sculpin MT-CYB.

SEQ ID NO: 75 is an exemplary probe to detect Slimy Sculpin MT-CYB.

SEQ ID NO: 76 is an exemplary forward primer to amplify round whitefish MT-RNR2.

SEQ ID NO: 77 is an exemplary reverse primer to amplify whitefish MT-RNR2.

SEQ ID NO: 78 is an exemplary probe to detect whitefish MT-RNR2.

SEQ ID NO: 79 is an exemplary forward primer to amplify round whitefish MT-CYB.

SEQ ID NO: 80 is an exemplary reverse primer to amplify whitefish MT-CYB.

SEQ ID NO: 81 is an exemplary probe to detect whitefish MT-CYB.

SEQ ID NO: 82 is an exemplary forward primer to amplify round whitefish MT-ND1.

SEQ ID NO: 83 is an exemplary reverse primer to amplify whitefish MT-ND1.

SEQ ID NO: 84 is an exemplary probe to detect whitefish MT-ND1.

SEQ ID NO: 85 is an exemplary forward primer to amplify Dolly Varden MT-RNR2.

SEQ ID NO: 86 is an exemplary reverse primer to amplify Dolly Varden MT-RNR2.

SEQ ID NO: 87 is an exemplary probe to detect Dolly Varden MT-RNR2.

SEQ ID NO: 88 is an exemplary forward primer to amplify Dolly Varden MT-CYB.

SEQ ID NO: 89 is an exemplary reverse primer to amplify Dolly Varden MT-CYB.

SEQ ID NO: 90 is an exemplary probe to detect Dolly Varden MT-CYB.

SEQ ID NO: 91 is an exemplary forward primer to amplify Dolly Varden MT-ND1.

SEQ ID NO: 92 is an exemplary reverse primer to amplify Dolly Varden MT-ND1B.

SEQ ID NO: 93 is an exemplary probe to detect Dolly Varden MT-ND1.

SEQ ID NO: 94 is an exemplary forward primer to amplify arctic grayling MT-RNR1.

SEQ ID NO: 95 is an exemplary reverse primer to amplify arctic grayling MT-RNR1.

SEQ ID NO: 96 is an exemplary probe to detect arctic grayling MT-RNR1.

SEQ ID NO: 97 is an exemplary forward primer to amplify arctic grayling MT-RNR2.

SEQ ID NO: 98 is an exemplary reverse primer to amplify arctic grayling MT-RNR2.

SEQ ID NO: 99 is an exemplary probe to detect arctic grayling MT-RNR2.

SEQ ID NO: 100 is an exemplary forward primer to amplify arctic grayling MT-ND1.

SEQ ID NO: 101 is an exemplary reverse primer to amplify arctic grayling MT-ND1.

SEQ ID NO: 102 is an exemplary probe to detect arctic grayling MT-ND1.

SEQ ID NO: 103 is an exemplary forward primer to amplify Chinook salmon MT-RNR1.

SEQ ID NO: 104 is an exemplary reverse primer to amplify Chinook salmon MT-RNR1.

SEQ ID NO: 105 is an exemplary probe to detect Chinook salmon MT-RNR1.

SEQ ID NO: 106 is an exemplary forward primer to amplify Chinook salmon MT-RNR2.

SEQ ID NO: 107 is an exemplary reverse primer to amplify Chinook salmon MT-RNR2.

SEQ ID NO: 108 is an exemplary probe to detect Chinook salmon MT-RNR2.

SEQ ID NO: 109 is an exemplary forward primer to amplify Chinook salmon MT-CYB.

SEQ ID NO: 110 is an exemplary reverse primer to amplify Chinook salmon MT-CYB.

SEQ ID NO: 111 is an exemplary probe to detect Chinook salmon MT-CYB.

SEQ ID NO: 112 is an exemplary forward primer to amplify Coho salmon MT-RNR1.

SEQ ID NO: 113 is an exemplary reverse primer to amplify Coho salmon MT-RNR1.

SEQ ID NO: 114 is an exemplary probe to detect Coho salmon MT-RNR1.

SEQ ID NO: 115 is an exemplary forward primer to amplify Coho salmon MT-RNR1.

SEQ ID NO: 116 is an exemplary reverse primer to amplify Coho salmon MT-RNR1.

SEQ ID NO: 117 is an exemplary probe to detect Coho salmon MT-RNR1.

SEQ ID NO: 118 is an exemplary forward primer to amplify Coho salmon MT-ND1.

SEQ ID NO: 119 is an exemplary reverse primer to amplify Coho salmon MT-ND1.

SEQ ID NO: 120 is an exemplary probe to detect Coho salmon MT-ND1.

SEQ ID NO: 121 is an exemplary forward primer to amplify Coho salmon MT-ND1.

SEQ ID NO: 122 is an exemplary reverse primer to amplify Coho salmon MT-ND1.

SEQ ID NO: 123 is an exemplary probe to detect Coho salmon MT-ND1.

SEQ ID NO: 124 is an exemplary forward primer to amplify giant Pacific salamander MT-CYB.

SEQ ID NO: 125 is an exemplary reverse primer to amplify giant Pacific salamander MT-CYB.

SEQ ID NO: 126 is an exemplary probe to detect giant Pacific salamander MT-CYB.

SEQ ID NO: 127 is an exemplary forward primer to amplify giant Pacific salamander MT-CYB.

SEQ ID NO: 128 is an exemplary reverse primer to amplify giant Pacific salamander MT-CYB.

SEQ ID NO: 129 is an exemplary probe to detect giant Pacific salamander MT-CYB.

DETAILED DESCRIPTION

The following explanations of terms and methods are provided to better describe the present disclosure and to guide those of ordinary skill in the art in the practice of the present disclosure. The singular forms “a,” “an,” and “the” refer to one or more than one, unless the context clearly dictates otherwise. For example, the term “comprising a primer” includes single or plural primers and is considered equivalent to the phrase “comprising at least one primer.” The term “or” refers to a single element of stated alternative elements or a combination of two or more elements, unless the context clearly indicates otherwise. As used herein, “comprises” means “includes.” Thus, “comprising A or B,” means “including A, B, or A and B,” without excluding additional elements. Dates of GenBank® Accession Nos. referred to herein are the sequences available at least as early as Apr. 13, 2017. All references and GenBank® Accession numbers cited herein are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided.

Amplifying a Nucleic Acid Molecule:

To increase the number of copies of a nucleic acid molecule, for example using PCR or qPCR. The resulting amplification products are called “amplicons.”

An example of in vitro amplification is the polymerase chain reaction (PCR), in which a nucleic acid molecule, such as DNA obtained from an environmental sample, is contacted with a pair of oligonucleotide primers, under conditions that allow for hybridization of the primers to the nucleic acid molecule. The primers are extended under suitable conditions, dissociated from the template, and then re-annealed, extended, and dissociated to amplify the number of copies of the nucleic acid molecule. Other examples of in vitro amplification techniques that can be used with the disclosed methods include real-time PCR, reverse transcription PCR (RT-PCR), quantitative real-time PCR (qPCR), reverse transcriptase semi-nested PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Contacting:

Placement in direct physical association; includes both in solid and liquid form. For example, contacting can occur in vitro with isolated nucleic acid molecules in solution, for example in a qPCR reaction mixture.

Detect:

To determine the existence or presence of, for example to determine whether a target nucleic acid molecule (such as plant chloroplast DNA, algae chloroplast DNA, fungal mitochondrial DNA, animal group DNA, and/or animal species DNA) is present in an environmental sample.

Fluorophore:

A chemical compound, which when excited by exposure to a particular stimulus such as a defined wavelength of light, emits light (fluoresces), for example at a different wavelength. The disclosed primers and probes can be labeled with (e.g., have attached thereto) a fluorophore (e.g., have a fluorophore attached thereto).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules eliminates the need for an external source of electromagnetic radiation, such as a laser. Examples of chemiluminescent molecules include, but are not limited to, aequorin.

Examples of particular fluorophores that can be used with the primers and probes disclosed herein are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (*Lucifer* Yellow VS), N-(4-anilino-1-naphthyl)maleimide, anthranilamide, Brilliant Yellow, Yakima Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride);

4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other fluorophores known to those skilled in the art can also be used, for example those available from Molecular Probes (Eugene, Oreg.).

Hybridization:

To form base pairs between complementary regions of two strands of DNA, RNA, or between DNA and RNA, thereby forming a duplex molecule. For example, the primers and probes disclosed herein (Tables 3 and 7) can form a duplex molecule with a target nucleic acid molecule or amplicon generated from such a target. Hybridization conditions resulting in particular degrees of stringency will vary depending upon the nature of the hybridization method and the composition and length of the hybridizing nucleic acid molecules. Generally, the temperature of hybridization and the ionic strength (such as the $Na^+$ concentration) of the hybridization buffer will determine the stringency of hybridization. However, for hybridization conditions related to PCR, the salt concentration is generally fixed by the buffer conditions and stringency of hybridization controlled by temperature (for example 42° C. low stringency, 48-50° C. medium stringency, and 55-60° C. high stringency).

Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). For purposes of this disclosure, "stringent conditions" encompass conditions under which hybridization only will occur if there is less than 25% mismatch between the hybridization molecule and the target sequence. "Moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 5% mismatch will not hybridize.

Moderately stringent hybridization conditions are when the hybridization is performed at about 42° C. in a hybridization solution containing 25 mM $KPO_4$ (pH 7.4), 5×SSC, 5×Denhart's solution, 50 μg/mL denatured, sonicated salmon sperm DNA, 50% formamide, 10% Dextran sulfate, and 1-15 ng/mL probe (about $5\times10^7$ cpm/μg), while the washes are performed at about 50° C. with a wash solution containing 2×SSC and 0.1% sodium dodecyl sulfate.

Highly stringent hybridization conditions are when the hybridization is performed at about 42° C. in a hybridization solution containing 25 mM $KPO_4$ (pH 7.4), 5×SSC, 5×Denhart's solution, 50 μg/mL denatured, sonicated salmon sperm DNA, 50% formamide, 10% Dextran sulfate, and 1-15 ng/mL probe (about $5\times10^7$ cpm/μg), while the washes are performed at about 55° C. with a wash solution containing 0.2×SSC and 0.1% sodium dodecyl sulfate.

Very highly stringent hybridization conditions are when the hybridization is performed at about 42° C. in a hybridization solution containing 25 mM $KPO_4$ (pH 7.4), 5×SSC, 5×Denhart's solution, 50 μg/mL denatured, sonicated salmon sperm DNA, 50% formamide, 10% Dextran sulfate, and 1-15 ng/mL probe (about $5\times10^7$ cpm/μg), while the washes are performed at about 65° C. with a wash solution containing 0.2×SSC and 0.1% sodium dodecyl sulfate. 20×SSC is 3.0 M NaCl/0.3 M trisodium citrate.

Isolated:

An "isolated" biological component (such as a nucleic acid molecule, organism, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include prostate cancer-related molecules (such as DNA or RNA) and proteins purified by standard purification methods. The term also embraces nucleic acid molecules, proteins and peptides prepared by recombinant expression in a host cell as well as chemically synthesized nucleic acid molecules and proteins. For example, an isolated nucleic acid molecule is one that is substantially separated from other types of nucleic acid molecules in a cell. Isolated does not require absolute purity, and can include nucleic acid molecules that are at least 50% isolated, such as at least 75%, 80%, 90%, 95%, 98%, 99% or even 100% isolated.

Label:

An agent capable of detection, for example by spectrometry, flow cytometry, or microscopy. For example, a label can be attached to a nucleic acid molecule or protein, thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Oligonucleotide:

A linear polynucleotide (such as DNA or RNA) sequence, for example of at least 6 nucleotides, for example at least 9, at least 15, at least 18, at least 24, at least 30, or at least 50 nucleotides long, such as 12-40 nucleotides, 18 to 35 nucleotides, 18 to 30 nucleotides, 19 to 30 nucleotides, 19 to 29 nucleotides, or 20 to 29 nucleotides. An oligonucleotide can contain non-naturally occurring portions, such as altered sugar moieties or inter-sugar linkages, such as a phosphorothioate oligodeoxynucleotide. In particular examples, an oligonucleotide containing non-naturally occurring portions can bind to RNA or DNA, and include peptide nucleic acid (PNA) molecules. In some examples an oligonucleotide can include unnatural nucleotides.

Primer:

A short nucleic acid molecule which can be used to initiate the synthesis of a longer nucleic acid sequence. In some examples, a primer includes (e.g., has attached thereto) a detectable label.

Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example by PCR or other nucleic-acid amplification methods.

In particular examples, a primer that can be used with the disclosed methods and kits is about 10-50 nucleotides, for example about 12 to 50 nucleotides, 15 to 40 nucleotides, 15 to 30 nucleotides, 12 to 40 nucleotides, 18 to 35 nucleotides, 18 to 30 nucleotides, 18 to 25 nucleotides 19 to 30 nucleotides, 19 to 29 nucleotides, or 20 to 29 nucleotides.

Probe:

A short nucleic acid molecule which can be used to detect (for example by hybridizing to) the presence of a target nucleic acid molecule, which includes (e.g., has attached thereto) a detectable label and in some examples also a fluorescence quencher. In particular examples, a probe that can be used with the disclosed methods and kits is about 10-50 nucleotides, for example about 12-50 nucleotides, 15-40 nucleotides, 15-30 nucleotides, 12-40 nucleotides, 18 to 35 nucleotides, 18 to 30 nucleotides, 19 to 30 nucleotides, 19 to 29 nucleotides, or 20 to 29 nucleotides.

Sample:

An environmental specimen containing DNA, RNA (e.g., mRNA), proteins, or combinations thereof. Examples include, but are not limited to, water (such as freshwater, brackish water, saltwater) soil and air. In some examples, samples are used directly in the methods provided herein. In some examples, samples are manipulated prior to analysis using the disclosed methods, such as through concentrating, filtering, centrifuging, diluting, desalting, denaturing, reducing, alkylating, proteolyzing, or combinations thereof. In some examples, components of the samples are isolated or purified prior to analysis using the disclosed methods, such as isolating cells, proteins, and/or nucleic acid molecules from the samples.

Sequence Identity:

The identity between two or more nucleic acid sequences, or two or more amino acid sequences, is expressed in terms of the identity between the sequences. Sequence identity can be measured in terms of percentage identity; the higher the percentage, the more identical the sequences are.

Methods of alignment of sequences for comparison are well known. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biomedical Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: −i is set to a file containing the first nucleic acid sequence to be compared (such as C:\seq1.txt); −j is set to a file containing the second nucleic acid sequence to be compared (such as C:\seq2.txt); −p is set to blastn; −o is set to any desired file name (such as C:\output.txt); −q is set to −1; −r is set to 2; and all other options are left at their default setting. For example, the following command can be used to generate an output file containing a comparison between two sequences: C:\Bl2seq −i c:\seq1.txt −j c:\seq2.txt −p blastn −o c:\output.txt −q −1 −r 2.

Once aligned, the number of matches is determined by counting the number of positions where an identical nucleotide is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 19 matches when aligned with a test sequence having 20 nucleotides is 95.0 percent identical to the test sequence (19÷20*100=95.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing 21 nucleotides that aligns with 19 consecutive nucleotides from an identified sequence as follows contains a region that shares 90 percent sequence identity to that identified sequence (that is, 19÷21*100=90).

One indication that two nucleic acid molecules are closely related is that the two molecules hybridize to each other under stringent conditions (such as high or very high stringency), as described above. In some examples, the primers and probes disclosed in SEQ ID NOS: 1-129 can be altered in a few nucleotides (such as 1, 2, 3, 4, or 5 nucleotides) without affecting the ability of the primer or probe to function properly using the methods disclosed herein. In one example, a primer or probe having at least 90%, at least 91%, at least 92%, at least 93%, at least 94%, at least 95%, at least 96%, at least 97%, at least 98%, or at least 99% sequence identity to any of SEQ ID NOS: 1-129, can be used in the methods and kits disclosed herein.

Under Conditions Sufficient for:

A phrase that is used to describe any environment that permits the desired activity. An example includes contacting primers (and in some examples also a nucleic acid probe) with a nucleic acid molecule (such as one from an environmental sample) with reagents and temperature conditions sufficient to allow amplification and detection of the target nucleic acid molecule in the sample.

Overview

Environmental stewardship requires timely, accurate information related to the status of a given ecosystem and the species that occupy it. Real-time quantitative polymerase chain reaction (qPCR) can be used to identify constituents within environmental DNA (eDNA), such as targeted detection of the presence of species-specific biological material within a localized geographic region. However, as such techniques are predicated on the specificity and sensitivity of the PCR assay, validation of each eDNA qPCR assay in development is performed both under controlled laboratory conditions and when challenged with field-derived eDNA samples. Such a step-wise approach forms the basis for incorporation of innovative qPCR design features that strengthen the implementation and interpretation of the disclosed eDNA assay.

Described herein, is a qPCR based method of evaluating, determining or confirming the presence of amplifiable DNA (e.g., DNA that is capable of supporting amplification in a qPCR based assay) from field or environmental samples that uses a positive control primer set (forward and reverse primer) targeted at an abundant or ubiquitous DNA source present in the environment that the sample is collected from. Field or environmental samples can be collected from a variety of ecosystems, such as freshwater, brackish water, saltwater, soil and air. The disclosed amplification assay, which uses primer sets specific for plant, algal or fungal DNA, confirms that the sample is of sufficient quality to support subsequent sample PCR interrogation with different targeted primer sets specific for animal group or animal species. The disclosed primer sets are refractory to the presence of human DNA and/or do not amplify, target and/or bind human DNA under the assay conditions. This method can be used to increase the confidence in a negative or positive result. The disclosed qPCR based method specifically uses the DNA amplification test within the context of how the assay is run. A conceptual schema of the disclosed methods is presented in FIG. 1.

As shown in FIG. 1, a test sample from the environment (esample) is obtained. If desired, nucleic acid molecules can be isolated from the sample prior to performing qPCR. Nucleic acid molecules in the sample are amplified using qPCR, using one or more nucleic acid primer sets (and in some examples also a nucleic acid probe) specific for plant, algal or fungal DNA, such as primer sets specific for plant chloroplast DNA, algae chloroplast DNA, fungal mitochondrial DNA or both plant chloroplast and algae chloroplast DNA. The primer sets used amplify a nucleic acid molecules that are abundant or ubiquitous in the environment that the sample is collected from (e.g., serve as a positive control), such as a plant known to be in the environment of a water sample tested. This step allows one to confirm the integrity of the nucleic acid molecules in the test sample. If the positive control provides a positive result, the sample can further be analyzed using qPCR for the presence of the target animal group and/or animal species, using one or more nucleic acid primer sets (and in some examples also a nucleic acid probe) specific for the target animal group and/or animal species. A forward and reverse primer set specific for animal group DNA is specific for a plurality of different animals in the same Class, Order, Family, or Genus. In one example, the forward and reverse primer set specific for the animal group DNA is specific for a plurality of mammals, amphibians, fish, or invertebrates, such as a plurality of frogs. In some examples, the forward and reverse primer set specific for the animal group DNA is capable of amplifying animal mitochondrial DNA.

The present application provides specific examples from the North American bullfrog (*Lithobates* (*Rana*) *catesbeiana*; hereafter referred to as bullfrog), and the Rocky Mountain tailed frog (*Ascaphus montanus*; hereafter referred to as tailed frog). Both species are listed as least concern by the International Union for Conservation of Nature, although there are some populations that are known to be at risk. The bullfrog is native to eastern North America and has been introduced to the west and all continents except Antarctica worldwide. Some native bullfrog populations (such as in eastern Ontario and Québec) are threatened whereas introduced populations, such as those in British Columbia, may contribute to declines of other native frog species not adapted to their presence. Despite its high abundance in the Northwestern United States, the tailed frog is federally designated as threatened by the Committee on the Status of Endangered Wildlife In Canada and a red-listed species in British Columbia due to a restricted range, low number of known occurrence records, low population size in geographic locations, and stream sedimentation due to roads, logging and fire.

Using these two species as examples, a novel hierarchical approach for qPCR assay design specifically for eDNA applications using water samples and filtration techniques is provided. This hierarchical validation process can mitigate the potential for false positive and false negative results to provide greater confidence in eDNA-based methods and improved interpretive power in the associated results.

The methods and kits described herein can be used to generate eDNA assays for one or more animal species, including but not limited to amphibian, fish, mammalian or invertebrate species. The amphibian, fish, mammalian or invertebrate species targeted may be invasive species within the environment or ecosystem the samples are collected from, or species of management interest. Specific invasive species or species of management interest in the Pacific Northwest region of North America include, but are not limited to, bullfrog, Green frog, Coastal and Rocky Mountain tailed frogs, Northern leopard frog, Cascades frog, Oregon spotted frog, Northern red-legged frog, white sturgeon, Western toad, Great Basin spadefoot toad, blotched tiger salamander, Pacific giant salamander, Canadian toad, zebra mussel, Atlantic and Pacific salmon, Arctic grayling, slimy sculpin, and Pacific water shrew.

The methods and kits described herein can outperform conventional methods and kits by being able to identify the presence of one or more species within a single water, soil or air sample at low cost. The methods described herein outperform conventional eDNA methods by providing a definitive endogenous positive control in an eDNA sample allowing for appropriate interpretation of a negative result from a targeted eDNA assay and leading to confidence in a positive result.

Methods and Kits for Analyzing an Environmental Sample

Provided herein are methods and kits for analyzing an environmental sample, such as a water, air, or soil sample, for the presence of one or more target nucleic acid molecules, to provide an indication of the presence of a target organism (such as one or more amphibians, fish mammals and invertebrates). In some examples, more than one target nucleic acid molecule is identified in the sample, such as at least two, at least three, at least four, at least five, or at least 10 (such as 1, 2, 3, 4, 5, 6, 7, 8, 9, 10, 15, or 20 different targets). In some examples, such assays are multiplexed, such that the identification of one target nucleic acid molecules occurs simultaneously or contemporaneously.

In one example, the disclosed kits include (1) a forward and reverse primer set specific for plant chloroplast DNA, algae chloroplast DNA, fungal mitochondrial DNA or both plant chloroplast and algae chloroplast DNA, (2) a labeled nucleic acid probe specific for the plant chloroplast DNA, algae chloroplast DNA, fungal mitochondrial DNA or both plant chloroplast and algae chloroplast DNA, (3) a forward and reverse primer set specific for an animal group DNA, and/or a forward and a reverse primer set specific for an animal species DNA, and (4) a labeled nucleic acid probe specific for the animal group DNA and/or a labeled nucleic acid probe specific for the animal species DNA, wherein none of the forward and reverse primer sets in the kit are capable of amplifying human DNA and wherein none of the labeled nucleic acid probes in the kit are capable of hybridizing to human DNA, for example under the amplification conditions used in the assay, such as under stringent conditions. The probes and primer sets are designed to not detect human DNA to preserve integrity of the assay and confidence in assay interpretation. Such kits can include other components, such as a membrane filter, container for holding or collecting an environmental sample, reagents for isolating DNA (such as ethanol), reagents for qPCR (such as DNA polymerase, dNTPs, and/or $MgCl_2$), a protease, forceps, gloves, or combinations thereof.

In one example, the disclosed methods for analyzing one or more different target nucleic acid molecules (such as target DNA) in a sample, includes contacting (e.g., incubating) nucleic acid molecules in the sample with (1) a forward and reverse primer set specific for plant chloroplast DNA, algae chloroplast DNA, fungal mitochondrial DNA or both plant chloroplast and algae chloroplast DNA and (2) a forward and reverse primer set specific for an animal group DNA and/or a primer set specific for an animal species DNA. The forward and reverse primer sets used in the methods are not capable of amplifying human DNA. The resulting mixture is then incubated under conditions that allow for amplification of the one or more target nucleic acid molecules in the sample, thereby generating amplicons. In some examples, at least 40, at least 45, or at least 50 cycles of amplification are performed. In one example quantitative real-time PCR (qPCR) reaction conditions are used. The presence of amplicons is determined or measured (and in some examples quantified), wherein the presence of the amplicons indicates the presence of the one or more different target nucleic acid molecules in the sample. The sample can be an environmental sample, such as a fresh water sample, salt water sample, brackish water sample, air sample, or soil sample.

In some examples, the method can further include contacting the sample or the amplicons with (1) a labeled nucleic acid probe specific for the plant chloroplast DNA, algae chloroplast DNA, fungal mitochondrial DNA or both plant chloroplast and algae chloroplast DNA and (2) a labeled nucleic acid probe specific for the animal group DNA and/or a labeled nucleic acid probe specific for the animal species DNA, wherein the probes used are not capable of hybridizing to human DNA under the amplification conditions. In some examples, the method can further include filtering the sample (for example through a membrane or filter to remove undesirable materials and/or to capture nucleic acid molecules) and/or isolating nucleic acid molecules from the sample (for example by removing proteins from the sample), prior to contacting the sample with the primer sets.

In some examples, the method can further include confirming that the primer set and/or probes under the same amplification conditions do not produce detectable amplicons in the presence of human DNA In one embodiment, a chloroplast DNA primer set is used as a positive control in the assay for detecting a target animal group DNA. In another embodiment, a fungal DNA primer set as a positive control in the assay for detecting a target animal group DNA. In one example, the forward and reverse primer set specific for the animal group DNA is specific for a genus, Family, Order, or Class of animals. In one example, the forward and reverse primer set specific for the animal group DNA is specific for a plurality of mammals, amphibians, fish, or invertebrates, such as a plurality of frogs, a plurality of toads, a plurality of salamanders, a plurality of salmon, a plurality of trout, or a plurality of shrews. In some examples, the forward and reverse primer set specific for the animal group DNA is capable of amplifying animal mitochondrial DNA. In some examples, the kit includes and/or method uses at least two different sets of primers (and in some examples corresponding probes) for at least two different animal group DNA, such as one for amphibians, one for mammals, and another for fish. Combinations can be selected from the sets provided herein, such as those shown in Tables 3 and 7.

In some examples, the forward and reverse primer set specific for the animal species DNA of the kit or method is specific for at least one, at least two, or at least three, such as one, up to two, or up to three, (such as 1 to 5, 1 to 4, 1 to 3, or 2 to 3, such as 1, 2, 3, 4, or 5) different species of mammal, amphibian, fish, or invertebrate. In some examples, the forward and reverse primer set specific for the animal species DNA of the kit or method is specific for: *Anaxyrus* (*Bufo*) *boreas* (Western toad), *Ascaphus montanus* (Rocky Mountain tailed frog), *Ascaphus truei* (Pacific (Coastal) tailed frog), *Lithobates* (*Rana*) *catesbeiana* (North American bullfrog), *Lithobates pipiens* (Northern leopard frog), *Rana aurora* (Northern red-legged frog), *Rana cascadae* (Cascades frog), *Rana luteiventris* (Columbia spotted frog), *Rana pretiosa* (Oregon spotted frog), *Sorex bendirii* (Pacific water shrew), *Lithobates* (*Rana*) *sylvaticus* (Wood frog), *Cottus cognatus* (Slimy Sculpin), *Prosopium cylindraceum* (Round Whitefish), *Salvelinus malma* (Dolly Varden), *Thymallus arcticus* (Arctic Grayling), *Oncorhynchus tschawytscha* (Chinook Salmon), *Oncorhynchus kisutch* (Coho Salmon), *Dicamptodon tenebrosus* (Giant Pacific Salamander). In some examples, the kit includes and/or method uses at least two different sets of primers (and in some examples corresponding probes) for at least two different animal species DNA, such as one for *Anaxyrus* (*Bufo*) *boreas*, one for *Ascaphus montanus*, and another for *Ascaphus truei*. Combinations can be selected from the sets provided herein, such as those shown in Tables 3 and 7.

In one example, the forward and reverse primer set in the kit or used in the method includes (1) a forward primer specific for plant and algae chloroplast DNA that includes or consists of the nucleic acid sequence of SEQ ID NO: 1 (TCTAGGGATAACAGGCTGAT), and (2) a reverse primer specific for plant and algae chloroplast DNA that includes or consists of the nucleic acid sequence of SEQ ID NO: 2 (TGAACCCAGCTCACGTAC). In some such examples, the probe specific for plant and algae chloroplast DNA can include or consists of the nucleic acid sequence of SEQ ID NO: 3 (TTTGGCACCTCGATGTCGG).

In one example, the forward and reverse primer set in the kit or used in the method includes (1) a forward primer specific for fungal mitochondrial DNA that includes or consists of the nucleic acid sequence of SEQ ID NO: 58, and (2) a reverse primer specific for fungal mitochondrial DNA that includes or consists of the nucleic acid sequence of SEQ ID NO: 59. In some such examples, the probe specific for fungal mitochondrial DNA can include or consists of the nucleic acid sequence of SEQ ID NO: 60. In one example, the forward and reverse primer set in the kit or used in the method includes (1) a forward primer specific for fungal mitochondrial DNA that includes or consists of the nucleic acid sequence of SEQ ID NO: 61, and (2) a reverse primer specific for fungal mitochondrial DNA that includes or consists of the nucleic acid sequence of SEQ ID NO: 62. In some such examples, the probe specific for fungal mitochondrial DNA can include or consists of the nucleic acid sequence of SEQ ID NO: 63.

In one example, the forward and reverse primer set in the kit or used in the method includes (1) a forward primer specific for animal group DNA that includes or consists of the nucleic acid sequence of SEQ ID NO: 4 (AGGYGGATTTAGYAGTAAAAAG) and (2) a reverse primer specific for animal group DNA that includes or consists of the nucleic acid sequence of SEQ ID NO: 5 (TAYACTTACCATGTTACGACTT). In one example, the forward and reverse primer set in the kit or used in the method includes (1) a forward primer specific for animal group DNA that includes or consists of the nucleic acid sequence of SEQ ID NO: 7 (GGAAAGRTGAAATAGAAATGAAA) and (2) a reverse primer specific for animal group DNA that includes or consists of the nucleic acid sequence of SEQ ID NO: 8 (GTAGCTCRCTTAGTTTCGGG). In one example, the forward and reverse primer set in the kit or used in the method includes (1) a forward primer specific for animal group DNA that includes or consists of the nucleic acid sequence of SEQ ID NO: 10 (AGTTACCCTRGGGATAACAG) and (2) a reverse primer specific for animal group DNA that includes or consists of the nucleic acid sequence of SEQ ID NO: 11 (AACAAACGAACCWTTAGTAGC). In one example, the forward and reverse primer set in the kit or used in the method includes (1) a forward primer specific for animal group DNA that includes or consists of the nucleic acid sequence of SEQ ID NO: 25 (AAAGGACTTGGCGGTRCTTT) and (2) a reverse primer specific for animal group DNA that includes or consists of the nucleic acid sequence of SEQ ID NO: 26 (CCAAGCACACTTTCCAGTATG). In one example, the forward and reverse primer set in the kit or used in the method includes (1) a forward primer specific for animal group DNA that includes or consists of the nucleic acid sequence of SEQ ID NO: 52 and (2) a reverse primer specific for animal group DNA that includes or consists of the nucleic acid sequence of SEQ ID NO: 53. In one example, the forward and reverse primer set in the kit or used in the method includes (1) a forward primer specific for animal group DNA that includes or consists of the nucleic acid sequence of SEQ ID NO: 55 and (2) a reverse primer specific for animal group DNA that includes or consists of the nucleic acid sequence of SEQ ID NO: 56.

In some such examples, the probe specific for animal group DNA of the kit or used in the method includes or consists of the nucleic acid sequence of SEQ ID NO: 6 (ACACACCGCCCGTCACCCTC), the nucleic acid sequence of SEQ ID NO: 9 (TCGTACCTTTTGCATCATGGT), the nucleic acid sequence of SEQ ID NO: 12 (TTTACGACCTCGATGTTGGATCAG), the nucleic acid sequence of SEQ ID NO: 27 (ATGAAGYACGCACACACCGCCCG), the nucleic acid sequence of SEQ ID NO: 54, and/or the nucleic acid sequence of SEQ ID NO: 57.

In one example, the forward and reverse primer set specific for the animal species DNA in the kit or used in the method is specific for *Lithobates* (*Rana*) *catesbeiana* and includes (1) a forward primer that includes or consists of the nucleic acid sequence of SEQ ID NO: 13 (TTTTCACTTCATCCTCCCGTTT) and (2) a reverse primer that includes or consists of the nucleic acid sequence of SEQ ID NO: 14 (GGGTTGGATGAGCCAGTTTG). In one example, the forward and reverse primer set specific for the animal species DNA in the kit or used in the method is specific for *Lithobates* (*Rana*) *catesbeiana* and includes (1) a forward primer that includes or consists of the nucleic acid sequence of SEQ ID NO: 16 (GAGAACGCCCTTTAAATCTT) and (2) a reverse primer that includes or consists of the nucleic acid sequence of SEQ ID NO: 17 (GTCAAGCTGACGCTCATACG). Such kits can further include, and such methods can further use, a probe specific for animal species DNA that includes or consists of the nucleic acid sequence of SEQ ID NO: 15 (TTATCGCAGCAGCAAGTATGA) or the nucleic acid sequence of SEQ ID NO: 18 (ACAAACCCTCCGCCCACAAC).

In one example, the forward and reverse primer set specific for the animal species DNA in the kit or used in the method is specific for *Ascaphus montanus* and includes (1) a forward primer specific that includes or consists of the nucleic acid sequence of SEQ ID NO: 19 (ACGTCAACTATGGCTGGCTAATC) and (2) a reverse primer that includes or consists of the nucleic acid sequence of SEQ ID NO: 20 (GTCCTCGGCCAATGTGAAGA). In one example, the forward and reverse primer set specific for the animal species DNA in the kit or used in the method is specific for *Ascaphus montanus* and includes (1) a forward primer that includes or consists of the nucleic acid sequence of SEQ ID NO: 22 (ACTTTATTACGGCTCTTACTTG) and (2) a reverse primer that includes or consists of the nucleic acid sequence of SEQ ID NO: 23 (GTACGTTTCCGATGTAAGGGA). Such kits can further include, and such methods can further use, a probe specific for animal species DNA that includes or consists of the nucleic acid sequence of SEQ ID NO: 21 (CATGCAAATGGAGCATCATTC) or the nucleic acid sequence of SEQ ID NO: 24 (ATACGTATTACCATGAGGACAAATATC).

In one example, the forward and reverse primer set specific for the animal species DNA in the kit or used in the method is specific for *Anaxyrus* (*Bufo*)*boreas* and includes (1) a forward primer that includes or consists of the nucleic acid sequence of SEQ ID NO: 28 (TATACTATGGCTCATACCTC) and (2) a reverse primer that includes or consists of the nucleic acid sequence of SEQ ID NO: 29 (GGTTGCGTTATCTACCGAG). Such kits can further include, and such methods can further use, a probe specific for animal species DNA that includes or consists of the nucleic acid sequence of SEQ ID NO: 30 (TTAGTTATAGCCACAGCGTTTGTGGG).

In one example, the forward and reverse primer set specific for the animal species DNA in the kit or used in the method is specific for *Ascaphus truei* and includes (1) a forward primer that includes or consists of the nucleic acid sequence of SEQ ID NO: 31 (GAACATTGGCATTATCCTACTT) and (2) a reverse primer that includes or consists of the nucleic acid sequence of SEQ ID NO: 32 (AGGCGAAAAATCGTGTTAAC). Such kits can further include, and such methods can further use, a probe specific for animal species DNA that includes or consists of the nucleic acid sequence of SEQ ID NO: 33 (CGCTTTTGTAGGGTATGTGTTACCG).

In one example, the forward and reverse primer set specific for the animal species DNA in the kit or used in the method is specific for *Lithobates pipiens* and includes (1) a forward primer that includes or consists of the nucleic acid sequence of SEQ ID NO: 34 (AGCTTACCATGTGAACGTCTT) and (2) a reverse primer that includes or consists of the nucleic acid sequence of SEQ ID NO: 35 (TACTACTAAATCCACCTTCGCT). Such kits can further include, and such methods can further use, a probe specific for animal species DNA that includes or consists of the nucleic acid sequence of SEQ ID NO: 36 (CAATTGGCTACAATTTCTAATATAGAACAA);

In one example, the forward and reverse primer set specific for the animal species DNA in the kit or used in the method is specific for *Rana aurora* and includes (1) a forward primer that includes or consists of the nucleic acid sequence of SEQ ID NO: 37 (TGAAGAAGCGGGAATCAAA) and (2) a reverse primer that includes or consists of the nucleic acid sequence of SEQ ID NO: 38 (GCATACAGATTTCTTGTGTGTG). Such kits can further include, and such methods can further use, a probe specific for animal species DNA that includes or consists of the nucleic acid sequence of SEQ ID NO: 39 (TAAACTCATCATACACCTCTGTGCTC).

In one example, the forward and reverse primer set specific for the animal species DNA in the kit or used in the method is specific for *Rana cascadae* and includes (1) a forward primer that includes or consists of the nucleic acid sequence of SEQ ID NO: 40 (CCTAATTGCCCAAATCGCT) and (2) a reverse primer that includes or consists of the nucleic acid sequence of SEQ ID NO: 41 (CTCAAAATGACATCTGGCCC). Such kits can further include, and such methods can further use, a probe specific for animal species DNA that includes or consists of the nucleic acid sequence of SEQ ID NO: 42 (TGGCTGGCTCCTTCGTAATTTACATG).

In one example, the forward and reverse primer set specific for the animal species DNA in the kit or used in the method is specific for *Rana luteiventris* and includes (1) a forward primer that includes or consists of the nucleic acid sequence of SEQ ID NO: 43 (TTCCTCTACCAATCCCCTAT) and (2) a reverse primer that includes or consists of the nucleic acid sequence of SEQ ID NO: 44 (CCAGGAAAACAGTGCATAAG). Such kits can further include, and such methods can further use, a probe specific for animal species DNA that includes or consists of the nucleic acid sequence of SEQ ID NO: 45 (CAGCCTAACCGTTTACACAATTTTGGG).

In one example, the forward and reverse primer set specific for the animal species DNA in the kit or used in the method is specific for *Rana pretiosa* and includes (1) a forward primer that includes or consists of the nucleic acid sequence of SEQ ID NO: 46 (GTAACCTCCATGCTAACGGT) and (2) a reverse primer that includes or consists of the nucleic acid sequence of SEQ ID NO: 47 (CTATCACTAGGAATAGGAGGATC). Such kits can further include, and such methods can further use, a probe specific for animal species DNA that includes or consists of the nucleic acid sequence of SEQ ID NO: 48 (TTTCCACATCGGCCGAGGCCTC); and/or In one example, the forward and reverse primer set specific for the animal species DNA in the kit or used in the method is specific for *Sorex bendirii* and includes (1) a forward primer that includes or consists of the nucleic acid sequence of SEQ ID NO: 49 (AAACATGAAACATCGGAGTAC) and (2) a reverse primer that includes or consists of the nucleic acid sequence of SEQ ID NO: 50 (ATAATGAAAGGTAGGATAAAA). Such kits can further include, and such methods can further use, a probe specific for animal species DNA that includes or consists of the nucleic acid sequence of SEQ ID NO: 51 (CGCAACAGTAATTACAAACCTACTATCA).

In one example, the forward and reverse primer set specific for the animal species DNA in the kit or used in the method is specific for *Lithobates* (*Rana*) *sylvaticus* and includes (1) a forward primer that includes or consists of the nucleic acid sequence of SEQ ID NO: 64 and (2) a reverse primer that includes or consists of the nucleic acid sequence of SEQ ID NO: 65. Such kits can further include, and such methods can further use, a probe specific for animal species DNA that includes or consists of the nucleic acid sequence of SEQ ID NO: 66.

In one example, the forward and reverse primer set specific for the animal species DNA in the kit or used in the method is specific for *Cottus cognatus* and includes (1) a forward primer that includes or consists of the nucleic acid sequence of SEQ ID NO: 67, 70 or 73 and (2) a reverse primer that includes or consists of the nucleic acid sequence of SEQ ID NO: 68, 71, or 74. Such kits can further include, and such methods can further use, a probe specific for animal species DNA that includes or consists of the nucleic acid sequence of SEQ ID NO: 69, 72 or 75.

In one example, the forward and reverse primer set specific for the animal species DNA in the kit or used in the method is specific for *Prosopium cylindraceum* and includes (1) a forward primer that includes or consists of the nucleic acid sequence of SEQ ID NO: 76, 79 or 82 and (2) a reverse primer that includes or consists of the nucleic acid sequence of SEQ ID NO: 77, 80, or 83. Such kits can further include, and such methods can further use, a probe specific for animal species DNA that includes or consists of the nucleic acid sequence of SEQ ID NO: 78, 81 or 84.

In one example, the forward and reverse primer set specific for the animal species DNA in the kit or used in the method is specific for *Salvelinus malma* and includes (1) a forward primer that includes or consists of the nucleic acid sequence of SEQ ID NO: 85, 88 or 91 and (2) a reverse primer that includes or consists of the nucleic acid sequence of SEQ ID NO: 86, 89, or 92. Such kits can further include, and such methods can further use, a probe specific for animal species DNA that includes or consists of the nucleic acid sequence of SEQ ID NO: 87, 90 or 93.

In one example, the forward and reverse primer set specific for the animal species DNA in the kit or used in the method is specific for *Thymallus arcticus* and includes (1) a forward primer that includes or consists of the nucleic acid sequence of SEQ ID NO: 94, 97 or 100, and (2) a reverse primer that includes or consists of the nucleic acid sequence of SEQ ID NO: 95, 98, or 101. Such kits can further include, and such methods can further use, a probe specific for animal species DNA that includes or consists of the nucleic acid sequence of SEQ ID NO: 96, 99 or 102.

In one example, the forward and reverse primer set specific for the animal species DNA in the kit or used in the method is specific for *Oncorhynchus tschawytscha* and includes (1) a forward primer that includes or consists of the nucleic acid sequence of SEQ ID NO: 103, 106 or 109 and (2) a reverse primer that includes or consists of the nucleic acid sequence of SEQ ID NO: 104, 107, or 110. Such kits can further include, and such methods can further use, a probe specific for animal species DNA that includes or consists of the nucleic acid sequence of SEQ ID NO: 105, 108, or 111.

In one example, the forward and reverse primer set specific for the animal species DNA in the kit or used in the method is specific for *Oncorhynchus kisutch* and includes (1) a forward primer that includes or consists of the nucleic acid sequence of SEQ ID NO: 112, 115, 118 or 121 and (2) a reverse primer that includes or consists of the nucleic acid sequence of SEQ ID NO: 113, 116, 119 or 122. Such kits can further include, and such methods can further use, a probe specific for animal species DNA that includes or consists of the nucleic acid sequence of SEQ ID NO: 114, 117, 120, or 123.

In one example, the forward and reverse primer set specific for the animal species DNA in the kit or used in the method is specific for *Dicamptodon tenebrosus* and includes (1) a forward primer that includes or consists of the nucleic acid sequence of SEQ ID NO: 124 or 127 and (2) a reverse primer that includes or consists of the nucleic acid sequence of SEQ ID NO: 125 or 128. Such kits can further include, and such methods can further use, a probe specific for animal species DNA that includes or consists of the nucleic acid sequence of SEQ ID NO: 126 or 129.

The kits and methods provided herein can use combinations of the provided primer sets and probes, depending on the target of interest and the source of the sample. In some examples, the kits and methods provided herein use any combination of primer sets, and optionally the corresponding probe, provided in Tables 3 and 7.

The disclosed probes and primers for use in the disclosed methods and kits can vary slightly from the exact sequence provided. Thus, in some examples, primers and probes having at least 90%, at least 91%, at least 92%, at least 93%, at least 94%, at least 95%, at least 96%, at least 97%, at least 98%, or at least 99% sequence identity to any of SEQ ID NOS: 1-129 can be part of a kit provided herein, and can be used in the methods provided herein. In some examples, primers and probes having one or a few nucleotide variations, such as 1, 2, 3, 4, or 5 nucleotide variations to any of SEQ ID NOS: 1-129, without affecting the ability of the primer or probe to function properly using the methods disclosed herein, can be part of a kit provided herein, and can be used in the methods provided herein.

The disclosed probes and primers for use in the disclosed methods and kits, can include (e.g., have attached thereto) one or more labels, which can be used to detect amplification of a nucleic acid molecule, a resulting amplicon, or both. In some examples, the disclosed probes and primers include a fluorophore. In some examples, the disclosed probes include a fluorophore and a quencher of fluorescence. In one example, the disclosed probes include a fluorophore (e.g., 6-carboxyfluorescein or tetrachlorofluorescein) covalently attached to the 5'-end of the probe and a quencher (e.g., tetramethylrhodamine (TAMRA)) at the 3'-end of the probe.

Example 1

Method to Identify Invasive Bullfrogs

A water sample from the field (such as a resource development site or mining location) is filtered to capture DNA present in the water onto a filter. The DNA is isolated from the filter and the presence or absence of DNA originating from a species of management interest is determined using qPCR.

The disclosed qPCR method allows for assessment of sample quality associated with isolation of eDNA from collected environmental samples. Samples that pass this initial test are analyzed further using a panel of primers and probes provided herein that are specific for a target, for example, an anuran species of interest. Additional assessment of the presence of an animal group (e.g., frog or mammal) can be performed for added interpretation. The disclosed tripartite qPCR-based eDNA assay has been used in a number of active field surveys following laboratory evaluation of tool efficacy (selectivity and sensitivity). The performance of the assay demonstrates robust data returns with high confidence in their interpretation.

Figure 7:
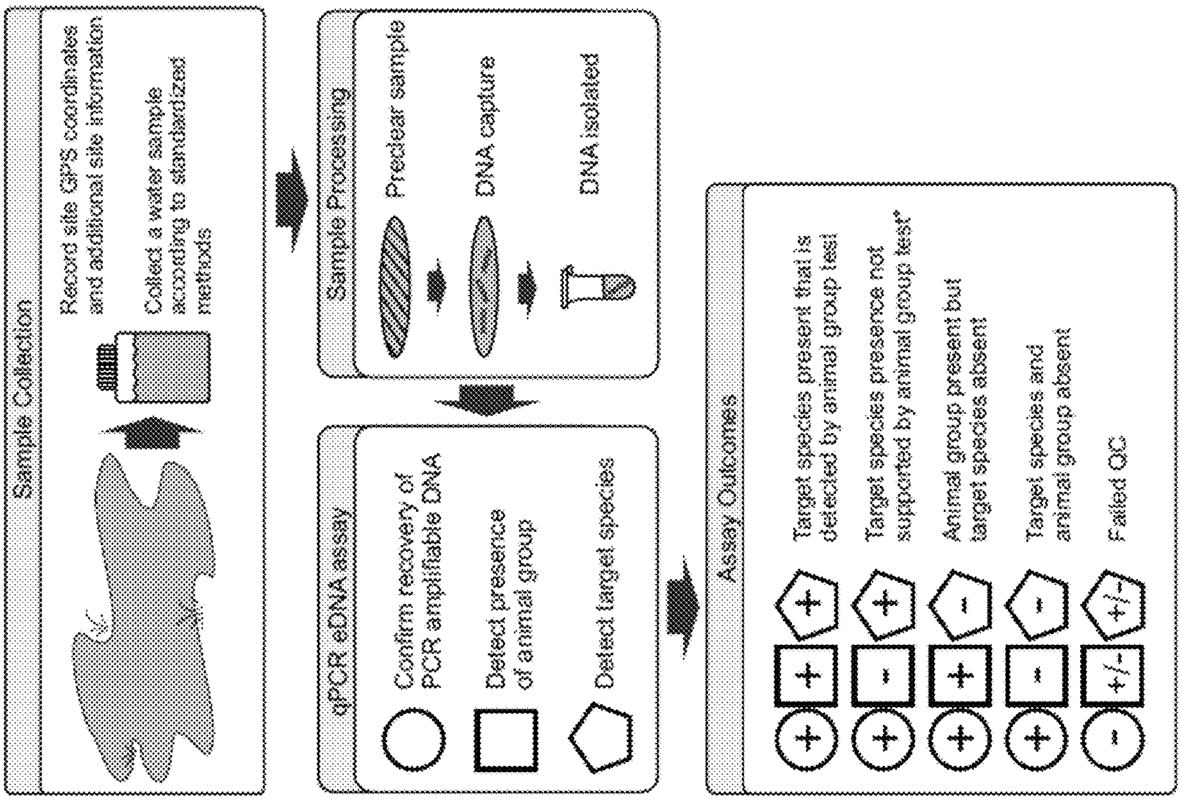
FIG. 7. Schematic drawing depicting application of a tripartite test methodology for detection of assayable DNA (circle), animal group (square), and specific species (pentagon) within an environmental water sample to provide greater confidence in eDNA assay results.

FIG. 7 is a schematic depicting application of a tripartite test methodology for high confidence determination of the detection status of assayable DNA ("DNA amplification test"; circle), animal group (square), and animal species (pentagon) within an environmental water sample to provide greater confidence in eDNA assay results. The test result indicated by an asterisk may require additional scrutiny to determine whether the negative animal group outcome is indicating a false positive species-specific detection or not.

A prototype of multiple individual qPCR assays for ten (10) specific species of management interest to British Columbia has been developed. The species include bullfrog, coastal and Rocky Mountain tailed frogs, leopard frog, cascades frog, Columbia and Oregon spotted frog, red-legged frog, Western toad, and Pacific water shrew. Further, these individual assays can be combined together into multiplex assays for greater throughput and cost savings.

One innovation is the inclusion of a DNA amplification test for increased confidence in assay performance and data interpretation. The test can be performed immediately after sample processing to isolate DNA off of the filter. This test, based upon primer sets directed to plant, algal or fungal DNA confirms that the sample is of sufficient quality to support subsequent PCR interrogation with different targeted primer sets directed against animal group or animal species. Samples that fail this test are sent through additional sample clean-up and retested. Samples that pass this test are cleared for further eDNA evaluation.

To illustrate the impact of the decision-making power of the addition of a DNA amplification test, consider the results shown in Table 1, aimed at determining whether or not a region has been colonized by invasive bullfrogs.

TABLE 1

Results of an eDNA survey of 17 different sites (A-Q) to determine the presence of invasive bullfrogs. The legend under the table presents the interpretation schema for the results of the combination of the DNA amplification test with the frog group and bullfrog specific tests.

| Sample | eDNA Recovered | DNA Amplification Call | | Frog Call | | Bullfrog Call | | Interpretation | |
|---|---|---|---|---|---|---|---|---|---|
| ID | (ng/uL) | Before | After | Before | After | Before | After | Before | After |
| A1 | 40.5 | Y | | Y | | N | | 2 | |
| A2 | 31.4 | Y | | N | | N | | 3 | |
| A3 | 39.8 | Y | | N | | N | | 3 | |
| B1 | 43.9 | Y | | N | | N | | 3 | |
| B2 | 40.2 | Y | | N | | N | | 3 | |
| B3 | 32.9 | Y | | N | | N | | 3 | |

TABLE 1-continued

| | | | | | | | | | |
|---|---|---|---|---|---|---|---|---|---|
| C1 | 28.0 | Y | | N | | N | | 3 | |
| C2 | 24.7 | Y | | N | | N | | 3 | |
| C3 | 20.6 | Y | | Y | | N | | 2 | |
| DW1 | 1.7 | N | | Y | | N | | 7 | |
| D1 | 53.1 | Y | | Y | | N | | 2 | |
| D2 | 32.2 | Y | | Y | | N | | 2 | |
| E1 | 37.8 | Y | | N | | N | | 3 | |
| E2 | 44.5 | Y | | Y | | N | | 2 | |
| F1 | 45.8 | Y | | N | | N | | 3 | |
| F2 | 97.2 | Y | | N | | N | | 3 | |
| F3 | 66.9 | Y | | N | | N | | 3 | |
| G1 | 37.9 | Y | | Y | | N | | 2 | |
| G2 | 31.4 | Y | | Y | | N | | 2 | |
| G3 | 42.0 | Y | | N | | N | | 3 | |
| H1 | 45.5 | Y | | N | | N | | 3 | |
| H2 | 46.5 | Y | | N | | N | | 3 | |
| H3 | 51.4 | Y | | N | | N | | 3 | |
| I1 | 28.6 | Y | | N | | N | | 3 | |
| I2 | 28.7 | Y | | N | | N | | 3 | |
| I3 | 22.4 | Y | | N | | N | | 3 | |
| J1 | 36.3 | Y | | N | | N | | 3 | |
| J2 | 40.4 | Y | | N | | N | | 3 | |
| J3 | 52.3 | Y | | N | | N | | 3 | |
| K1 | 27.8 | Y | | N | | N | | 3 | |
| K2 | 18.7 | Y | | Y | | N | | 2 | |
| K3 | 23.1 | Y | | Y | | N | | 2 | |
| L1 | 87.9 | Y | | N | | N | | 3 | |
| L2 | 96.8 | Y | | Y | | N | | 2 | |
| L3 | 78.6 | Y | | Y | | Y | | 1 | |
| DW2 | 2.8 | N | | N | | N | | 5 | |
| M1 | 44.9 | N | N | N | N | N | N | 5 | 5 |
| M2 | 37.8 | N | N | N | N | N | N | 5 | 5 |
| M3 | 75.7 | N | N | N | N | N | N | 5 | 5 |
| N1 | 26.3 | N | Y | N | N | N | N | 5 | 3 |
| N2 | 73.7 | N | N | N | N | N | N | 5 | 5 |
| N3 | 41.0 | N | Y | N | N | N | N | 5 | 3 |
| O1 | 27.5 | N | Y | N | N | N | N | 5 | 3 |
| O2 | 33.2 | N | Y | N | N | N | N | 5 | 3 |
| O3 | 31.9 | Y | | N | | N | | 3 | |
| P1 | 71.8 | N | Y | N | Y | N | Y | 5 | 1 |
| P2 | 76.4 | N | Y | N | Y | N | Y | 5 | 1 |
| P3 | 51.6 | N | Y | N | N | N | N | 5 | 3 |
| Q1 | 54.2 | N | Y | N | N | N | N | 5 | 3 |
| Q2 | 38.9 | Y | | N | | Y | | 4 | |
| Q3 | 50.4 | N | Y | N | Y | N | Y | 5 | 1 |
| DW3 | 2.4 | N | | N | | N | | 5 | |

Legend:
Possible Interpretation Patterns;
Presence = Y,
Absence = N

| | | |
|---|---|---|
| 1 | Y, Y, Y | DNA amplified, frogs present, target species present |
| 2 | Y, Y, N | DNA amplified, frogs present, target species not present |
| 3 | Y, N, N | DNA amplified, frogs not present, target species not present |
| 4 | Y, N, Y | DNA amplified, frogs not present, target species present |
| 5 | N, N, N | DNA not amplified - DNA absent or not amplifiable |
| 6 | N, N, Y | DNA not amplified - false positive for presence of bullfrog |
| 7 | N, Y, N | DNA not amplified - false positive for presence of frogs |
| 8 | N, Y, Y | DNA not amplified - false positive for presence of frogs and bullfrog |

Water was collected from 17 different field sites (sites A to Q) in triplicate (except for two sites yielding duplicate samples) and three distilled water controls (DW1-3) were included prior to water sample filtration. DNA was isolated from the filters and resuspended in 150 μl of RNAse-free distilled water. The DNA yield was determined using UV spectrophotometry. The relative DNA recovery was highly consistent from sample to sample and the distilled water controls yielded lower DNA amounts. Application of the DNA amplification test provided herein, using the xPlant primers and probes (SEQ ID NOS: 1-3) showed 13 out of the 52 filter samples failed the test while 39 passed. All of the failed samples also yielded negative results for the frog animal group and bullfrog specific tests (interpretation 5). The 13 samples that failed the DNA amplification test could be because the DNA is degraded, PCR inhibitors are present, or as a result of extremely low total DNA levels. The UV spectrophotometric determination of DNA presence helps distinguish the distilled water controls from the environmental water samples, leaving DNA degradation or PCR inhibitors as candidates.

To differentiate between these two possibilities, the 13 samples that failed the DNA amplification test were subjected to a Zymogen OneStep™ PCR Inhibitor Removal Kit size exclusion column and the DNA amplification test re-run. Nine samples then supported DNA amplification (After-DNA Amplification Call). This indicates that PCR inhibitors were present in the samples that were removed upon clean up. The other four samples remained negative for DNA amplification suggesting that the DNA in these samples were degraded and should not be used for frog group or bullfrog species assessment. Thus, one of the 17 sites where water was collected (site M) was not capable of being assessed further with the eDNA assay due to failure of the samples to support DNA amplification.

Subsequent reassessment of the nine cleaned up samples that now subsequently passed the DNA amplification test with frog animal group and bullfrog specific primer sets, respectively, showed that most of the sites were negative for detection. However, three samples in sites P and Q tested positive for the presence of frogs, and bullfrogs in particular (P1, P2, Q3).

This survey using the disclosed methods provides an example of its importance towards eDNA assay integrity and increased confidence in the resultant data. The test allowed for the identification of three false negative samples whereby, following sample clean-up, the presence of the invasive bullfrog at sites within the survey region were detected. This is observation may impact wildlife conservation management decisions in the region. Additionally, the use of the disclosed DNA amplification methods provided the ability to rapidly assess eDNA sample quality and focus on clean-up of failed samples for maximal robustness in eDNA-based wildlife surveys.

Example 2

Materials & Methods

This example describes the materials and methods used to generate the results described in Examples 1 and 3.

Collection and Filtration of Environmental Water Samples

Duplicate environmental water samples were collected from the water's edge at six locations on either Vancouver Island for the assessment of bullfrog presence or the thalweg of lotic systems in Southeastern British Columbia, Canada for the assessment of tailed frog presence. Water samples (250 mL for bullfrog testing or 1000 mL for tailed frog testing) were collected at each field location in polypropylene bottles and stored in a cooler with ice packs during transport. All water samples underwent filtration within 24 hours of collection.

For the bullfrog test locations, two reusable Swinnex filter holders containing O-rings (Millipore Ltd., Etobicoke, ON, Canada; Cat #SX0002500) were prepared with one containing a Whatman 24 mm diameter glass microfibre filter (GE Healthcare Life Sciences, Mississauga, ON, Canada; Cat #1827-024) and the other containing a MF-Millipore 25 mm mixed cellulose membrane filter (0.45 μM pore size; Millipore; Cat #HAWP02500). Each water sample was loaded in multiple aliquots into a 60 mL BD Luer-Lok tip syringe (VWR International, Mississauga, ON, Canada) which was then attached in serial to first the glass filter and then the cellulose membrane filter. The entire water sample was filtered through the assemblage with repeated reloading of the syringe and a replacement of the Swinnex containing the glass filter, if required, to maintain an adequate flow rate. The Swinnex filter holders were reused for additional sample filtration once treated with bleach (5% w/v sodium hypochlorite) for 15 minutes followed by a 10 minute rinse with distilled water and air drying. For the tailed frog test locations, 1000 mL of water was collected and filtered under vacuum through a 47 mm cellulose nitrate filter (0.45 μM pore size; Thermo Fisher Scientific Inc., Ottawa, ON, Canada; Cat #N1452045). For all survey sites sampled, following filtration, cellulose filters were removed and placed individually in 2 mL screw-cap tubes containing 95-100% molecular grade ethanol.

Isolation of Total DNA from Filtered Water Samples

Prior to isolation of total DNA, all sample filters were randomized and processed blind to eliminate bias. All further work with filter samples was performed in a biological safety cabinet (NuAire, Plymouth, Minn., USA) including total DNA isolation from filters and assembly of the eDNA qPCR assay. In all instances of handling individual filter samples, non-serrated stainless steel forceps were used that had been treated sequentially with a bleach (5% w/v sodium hypochlorite) wash, a distilled water rinse, and then wiped dry. Filters were removed from ethanol, air dried on Whatman 55 mm diameter filter paper, and halved using the forceps. One half filter was placed in a new 1.5 mL tube for DNA isolation while the remaining unprocessed half filter was returned to 95-100% ethanol. Total DNA was recovered from each filter sample using the DNeasy Blood and Tissue Kit (QIAGEN Inc., Mississauga, ON, Canada; Cat #69506) as per the manufacturer's protocol with the following modifications; samples to be tested for the presence of bullfrogs used 180 μL Buffer ATL while samples to be tested for tailed frogs required 280 μL Buffer ATL and the remaining reagents were adjusted proportionally. For each sample, following overnight proteinase K digestion, both filter and liquid were transferred to a DNeasy column using bleach-treated and distilled water-rinsed forceps. DNA was eluted from each column with 100 μL Buffer AE. DNA was eluted from the spin column with 100 μL of Buffer AE and the nucleic acid concentration determined by $A_{260}$ spectrophotometry. DNA samples were stored at −20° C. prior to use in the eDNA qPCR assay.

DNA Primer Design

TaqMan®-based primer sets directed towards frogs were obtained from previously published information (eLICA1 [13] and eASMO [14]) or designed using organelle gene-specific sequence data from multiple species (NCBI Genome). An analogous generation of primer sets was carried out on chloroplast gene sequences obtained from freshwater plant species. Table 2 identifies the mitochondrial and chloroplast gene sequences and their associated or confounding species used in primer development.

TABLE 2

Cross-species gene sequence information incorporated into eDNA primer set design[a].

| Primer Set Gene Target | ePlant5 chloroplast 23S rRNA (rrn23) | eFrog2, eFrog3, eFrog5 mitochondria 16S rRNA (mtrnr2) |
|---|---|---|
| Comparator Species[b] | *Paradoxia multiseta*; KM462879 | *Lithobates catesbeiana*: M57527 |
| | *Chlorella vulgaris*: AB001684 | *Lithobate sylvatica*: AB639591 |
| | *Chlamydomonas reinhardtii*: FJ423446 | *Lithobates clamitans*: AY779204 |
| | | *Rana luteiventris* AY779194 |
| | *Scenedesmus obliquus*: DQ396875 | *Ascaphus truei*: AJ871087 |
| | *Staurastrum punctulatum*: AY958085 | *Pseudacris regilla*: AY291112 |
| | | *Pseudacris maculate*; AY291089 |

TABLE 2-continued

Cross-species gene sequence information incorporated into eDNA primer set design[a].

| | | |
|---|---|---|
| | *Closterium baillyanum*: KF060940 | *Pseudacris illinoensis*: AY291110<br>*Homo sapiens*: AP008824 |
| Primer Set | | |
| Gene | eLICA2 | eASMO9 |
| Target | mitochondria 12S rRNA (mtrnr1) | mitochondria cytochrome B (cytb) |
| Comparator Species[b] | *Lithobates catesbeiana*: M57527<br>*Lithobates sylvatica*: KP222281<br>*Rana maculata*: DQ283303<br>*Rana temporaria*: AB685766<br>*Lithobates pipiens*: DQ283123<br>*Pseudacris regilla*: AY819376<br>*Pseudacris crucifer*: AY819385<br>*Bufo americanus*: AY680211<br>*Spea bombifrons*: AY819327<br>*Ascaphus truei*: AJ871087<br>*Homo sapiens*: AP008824 | *Ascaphus montanus*: DQ087517<br>*Ascaphus truei*: AF277330<br>*Lithobates clamitans*: AY083277<br>*Lithobates catesbeiana*: NC_022696<br>*Lithobates sylvatica*: NC_027236<br>*Rana aurora*: EU552219<br>*Pseudacris maculata*: KJ536217<br>*Pseudacris crucifer*: KJ536191<br>*Pseudacris regilla*: KJ536196<br>*Bufo americanus*: AB159264<br>*Bufo boreas*: HM563929<br>*Homo sapiens*: AP008824 |

[a]Selection of pertinent species for use in eDNA primer design was performed using information on anurans from the Canadian Biodiversity (canadianbiodiversity.mcgill.ca/english/species/herps/anura.htm) and the BC Frogwatch Program (www.env.gov.bc.ca/wld/frogwatch/) websites and for freshwater plants using the Canadian Center for the Culture of Microorganisms (www3.botany.ubc.ca/cccm/FWAC/fwaccatalog.html) and AlgaeBase (www.algaebase.org/search/distribution/) websites.
[b]Each selected comparator species is followed by the NCBI GenBank ® accession number of the relevant sequence used in primer set design.

For each gene target, species-specific sequences were aligned by ClustalW and the output aln file assessed using BioEdit (Ibis Biosciences, Carlsbad, Calif., USA) and Primer Premier version 5 (Premier Biosoft, Palo Alto, Calif., USA) for generation of either cross-species (ePlant5 and eFrog2, 3, and 5) or species-restricted (eLICA2 and eASMO9) primer sets. The eLICA1 and eASMO hydrolysis probes were extended by four bases in the 3' direction from that previously published [13,14] to allow for use of an increased annealing temperature to enhance stringency in the present eDNA assay (Table 3). DNA amplification primers and associated TaqMan® hydrolysis probes were obtained from Integrated DNA Technologies (Coralville, Iowa, USA) and their characteristics are shown in Table 3.

TABLE 3

PCR primers used in eDNA assays for bullfrog and tailed frog, cross-species plant probe, and a cross-species frog probe.

| Species Target | Gene Target | Primer Set | Primer Name | Primer Sequence (SEQ ID NO:) | Amplicon Size | Reference |
|---|---|---|---|---|---|---|
| xPlant | chloroplast 23S rRNA | ePlant5 | 150134F<br>150135R<br>150139 Probe | TCTAGGGATAACAGGCTGAT (1)<br>TGAACCCAGCTCACGTAC (2)<br>TTTGGCACCTCGATGTCGG (3) | 147 | Present work |
| xFrog | mitochondrial 12S rRNA | eFrog2 | 150013F<br>150014R<br>150050 Probe | AGGYGGATTTAGYAGTAAAAAG (4)<br>TAYACTTACCATGTTACGACTT (5)<br>ACACACCGCCCGTCACCCTC (6) | 155 | Present work |
| xFrog | mitochondria 16S rRNA | eFrog3 | 150015F<br>150016R<br>150051 Probe | GGAAAGRTGAAATAGAAATGAAA (7)<br>GTAGCTCRCTTAGTTTCGGG (8)<br>TCGTACCTTTTGCATCATGGT (9) | 142 | Present work |
| xFrog | mitochondrial 16S rRNA | eFrog5 | 150019F<br>150020R<br>150053 Probe | AGTTACCCTRGGGATAACAG (10)<br>AACAAACGAACCWTTAGTAGC (11)<br>TTTACGACCTCGATGTTGGATCAG (12) | 121 | Present work |
| LICA | mitochondria cytochrome B | eLICA1 | BullfrogF<br>BullfrogR<br>Bullfrog Probe[a] | TTTTCACTTCATCCTCCCGTTT (13)<br>GGGTTGGATGAGCCAGTTTG (14)<br>TTATCGCAGCAGCAAGTATGA (15) | 84 | Strickler et al., 2015 |
| LICA | mitochondria 12S rRNA | eLICA2 | 150003F<br>150004R<br>150046 Probe | GAGAACGCCCTTTAAATCTT (16)<br>GTCAAGCTGACGCTCATACG (17)<br>ACAAACCCTCCGCCCACAAC (18) | 135 | Present work |
| ASMO | mitochondria cytochrome B | eASMO | qASMOF<br>qASMOR<br>ASMOProbe[a] | ACGTCAACTATGGCTGGCTAATC (19)<br>GTCCTCGGCCAATGTGAAGA (20)<br>CATGCAAATGGAGCATCATTC (21) | 90 | Pilliod et al., 2013 |

TABLE 3-continued

PCR primers used in eDNA assays for bullfrog and tailed frog, cross-species plant probe, and a cross-species frog probe.

| Species Target | Gene Target | Primer Set | Primer Name | Primer Sequence (SEQ ID NO:) | Amplicon Size | Reference |
|---|---|---|---|---|---|---|
| ASMO | mitochondria cytochrome B | eASMO9 | 150151F | ACTTTATTACGGCTCTTACTTG (22) | 176 | Present work |
| | | | 150153R | GTACGTTTCCGATGTAAGGGA (23) | | |
| | | | 150169 Probe | ATACGTATTACCATGAGGACAAATATC (24) | | |

[a]Primer sequences are modified from that previously published [13, 14] by addition of four additional bases at the 3' end to satisfy more stringent annealing conditions.

Isolation of Total DNA from Animal Tissues for qPCR Primer Validation

Total DNA for qPCR primer specificity and sensitivity validation was isolated from confirmed species sources: bullfrog tadpole tail muscle, *Lithobates* (*Rana*) *pipiens* (Northern leopard frog) adult liver, *Pseudacris regilla* (Pacific tree frog) tadpole whole body, tailed frog tadpole tail muscle, and *Xenopus laevis* (South African clawed frog) tadpole heart as well as from *Homo sapiens* (human) HEK293 cells using the DNeasy Blood and Tissue Kit (QIAGEN) with inclusion of RNase treatment as described by the manufacturer. Tissues were obtained. One bullfrog and Pacific tree frog tadpole each were locally caught, one adult Northern leopard frog was obtained from Carolina Biological Supply Company (Burlington, N.C.), and the *Xenopus laevis* tadpole was bred at the University of Victoria Aquatics Facility. Tailed frog tadpole tail muscle preserved in ethanol was obtained from a tadpole that died of natural causes.

Live animals were euthanized using 0.1% w/v (tadpoles) or 1% w/v (adults) tricaine methane sulfonate in dechlorinated municipal water containing 25 mM sodium bicarbonate prior to tissue collection. DNA was eluted from the spin column with 150 μL of Buffer AE and the nucleic acid concentration determined by $A_{260}$ spectrophotometry. DNA samples were stored at −20° C. prior to use in the eDNA qPCR assay.

Validation of qPCR Primer Sets for Application Towards eDNA Detection

The selectivity and sensitivity of bullfrog (eLICA1 and eLICA2), tailed frog (eASMO and eASMO9) and the cross-species frog (eFrog2, 3, and 5) primer sets were examined along with the efficacy of the plant chloroplast detection primer set (ePlant5) on an Mx3005P qPCR system (Agilent Technologies Inc., Santa Clara, Calif., USA). Each 15 μl qPCR amplification reaction consisted of 10 mM Tris-HCl (pH 8.3 at 20° C.), 50 mM KCl, 3 mM $MgCl_2$, 0.01% Tween 20, 0.8% glycerol, 69.4 nM ROX (Life Technologies, Burlington, ON, Canada), 10.5 pmol of forward and reverse PCR primer, 1.5 pmol of TaqMan hydrolysis probe, 200 μM dNTPs (FroggaBio Inc., North York, ON, Canada), one unit of Immolase DNA polymerase (FroggaBio), and 2 μl of DNA sample. The qPCR assembled to evaluate the ePlant5 primer set included 2 μL of isolated DNA sample from field sites 1, 6, and 7 as well as from tap water. In the selectivity test, the DNA sample included in the qPCR reaction was 2 μL of 5 μg/L isolated total DNA from bullfrog, leopard frog, tree frog, clawed frog, tailed frog, or human.

The sensitivity test included 2 μL addition of a five-fold dilution series (0.008-5 μg/L) of bullfrog (for eLICA1 and eLICA2) or tailed frog (for eASMO and eASMO9) isolated total DNA plus a "no DNA template" negative control. Twenty-three (ASMO) or twenty-five (LICA) technical replicates were run for each filtered water sample to determine the binomial error range at each dilution. Technical replicates involve running a replicate qPCR reaction on the same filtered eDNA sample. Binomial standard error was calculated as the square root of the product of the proportion of positives and negatives divided by the total number of technical replicates (Table 3).

DNA amplification reactions were subject to the following thermocycle conditions: an initial activation step of 9 min at 95° C. followed by 50 cycles of 15 sec denaturation at 95° C., 30 sec annealing at 64° C., and 30 sec polymerization at 72° C. Sequence specificity in qPCR-mediated DNA amplification for each primer set was confirmed through restriction endonuclease mapping of the DNA product.

Field Application of qPCR-Based eDNA Assays

Eight TaqMan®-based qPCR replicate reactions were performed for each field-derived sample and carried out as described above. Appropriate assay performance was determined for each qPCR plate by inclusion of a negative control lacking addition of DNA template and a positive control that contained 5 μg/L target-specific total DNA. Individual qPCR reactions were scored as positive if DNA amplification occurred within 30 (ePlant5) or 50 cycles (eLICA1, eASMO9, and eFrog3).

Example 3

Results

A PCR-based assay that detects the presence of a single animal species or a select group of related animals from a complex environmental DNA source was developed. In addition to appropriate sample collection methodology, an 'informed design' was performed for the molecular assay whereby known evolutionarily closely related species, members of the same animal family that are situated in the geographic survey region, and similar human sequences to the target gene were all factored into the primer design process to maximize eDNA assay specificity towards the target species and/or more broadly towards a given family or genera.

As the target biological material may be present at low abundance in field collected water samples, a number of factors are included in the eDNA assay. First, gene sequences used in assay development are commonly sourced from the mitochondrial genome, as the number of copies of this DNA template disseminated into the surrounding environment from a given species is higher in comparison to the nuclear genome. An additional consideration is the evolutionary plasticity that may be inherent in the nuclear genome across subspecies whereby whole genome duplication, gene fractionation, and pseudogenes lend increased complexity in DNA sequence targeting [15]. While potentially advantageous for inspection of the geographic distribution of a specific subspecies, such variation in the nuclear genome can confound evaluation at higher taxonomic levels (e.g., species, genus, or family). While the present study examined eukaryotic species, a survey of prokaryotic and viral populations within a given ecosystem can also be undertaken bearing in mind that diligent application of experimental controls are required during assay validation to exclude the influence, on eDNA assay development, of contaminated commercial reagents that may be used in nucleic acid isolation and PCR-based amplification [16-18].

Species Specificity of eDNA Assay Tools

The first phase of eDNA assay development involves in silico informatics to inform gene-specific primer design. The present eDNA assay includes two formats for detection of vertebrate species. The first format is designed to detect specific target species. The second involves a cross-species primer set capable of detecting multiple species representing an animal group.

Available information on mitochondrial gene sequences for the anuran target species and related potential confounder species were evaluated through DNA alignments. Candidate primer sets in this instance were either obtained from previously published studies (eLICA1 and eASMO) or generated (eLICA2 and eASMO9) for bullfrog and tailed frog, respectively. Three cross-species primer sets capable of detecting multiple frog species representing the animal group (eFrog2, eFrog3, eFrog5) were also designed de novo. Each of these primer sets were designed to eliminate possible cross-reaction with human mitochondrial DNA.

Table 3 demonstrates that all design possibilities to generate the eDNA assay can be empirically evaluated for their efficacy in PCR. Secondly, the PCR thermocycle is extended beyond its usual limits in an eDNA assay and DNA sequence (hence species) specificity is preserved with inclusion of TaqMan®-associated detection in a qPCR format. The presence of both the DNA amplification primer pair and a hydrolysis probe in assay development serves to enhance target specificity by allowing for increased placement of cross-species base-pair mismatches that minimize false positive detection of related members of the animal family or genus [20].

Figure 2A:
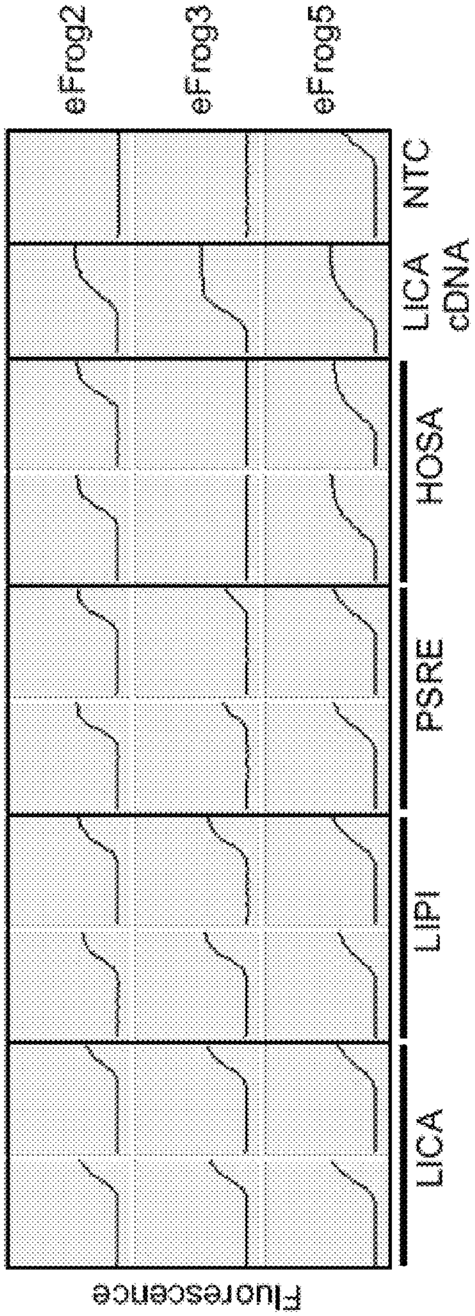
FIGS. 2A-2B. Cross-species analysis of qPCR-based detection of mitochondrial gene sequence with primer sets designed towards anurans. (A) Fluorescent-based amplification curves are shown representing assay reactions assembled using TaqMan-associated qPCR primer sets eFrog2, eFrog3, or eFrog5 and total DNA template from bullfrog (LICA), leopard frog (LIPI), tree frog (PSRE), or human (HOSA). Duplicate eDNA qPCR assay reactions are shown. A positive control comprising bullfrog brain cDNA (LICA cDNA) as well as a no template negative control (NTC) were included in the assay. For each reaction, successful amplification of DNA is shown by an increasing fluorescent signal. (B) Graphical representation of eFrog3 amplification results of replicate qPCR reactions (n=23 to 27) performed for against each DNA template with the mean abundance and standard error of the mean shown. Abundance for each qPCR replicate was determined as the assay thermocycle limit (50) minus the cycle threshold ($C_t$) value when amplification was detected.

The extended thermocycle program used for evaluation of eDNA used PCR-clean practices to minimize sample cross contamination and maintain eDNA assay integrity [19]. eDNA assay design pushes the limits of PCR detection and involves determination of an acceptable balance between sensitive, targeted detection and minimization of false positives for each individual test performed. As humans are involved in sample collection, processing, and evaluation, the eDNA assay does not detect human biological material including that of the field biologist collecting the sample and the laboratory personnel carrying out the qPCR assay as these represent a potential source of false positive signal. In silico analysis is not the final determining factor in ensuring a lack of unintentional cross-species priming. Rather an additional empirical evaluation is made, for example by designing frog cross-species primer sets. Although all three eFrog primer pairs amplified frog DNA well, two of the TaqMan®-based primer sets also detected human DNA (FIG. 2A). Thus, caution must be used in relying solely on in silico design parameters for determination of primer efficacy; undertaking a robust empirical validation program can be useful.

Determination of Specificity of eDNA Assay Tools

Evaluation of eDNA primer set efficacy includes determination of both maximum detection specificity and sensitivity with a requirement for the former parameter prior to investigation of the latter. While not an exact replacement for the complexity inherent in field-derived eDNA samples, use of serially-diluted purified total DNA from the species under consideration to define the extent of signal capture at low DNA template amounts is a reasonable course of action [21].

A three-step thermocycle was used in lieu of the more frequently used two-step method [5,14,20,22] and the use of stringent annealing temperatures during empirical assessment of DNA primer sets in an attempt to maximize specificity by exploiting the limited base pair mismatches that may exist within target genes between closely related species. In addition to eDNA tools that identify a single species, an opposing primer design criteria can be undertaken that exploits conserved sections of the target gene sequence to generate cross-species capability.

Figure 3:
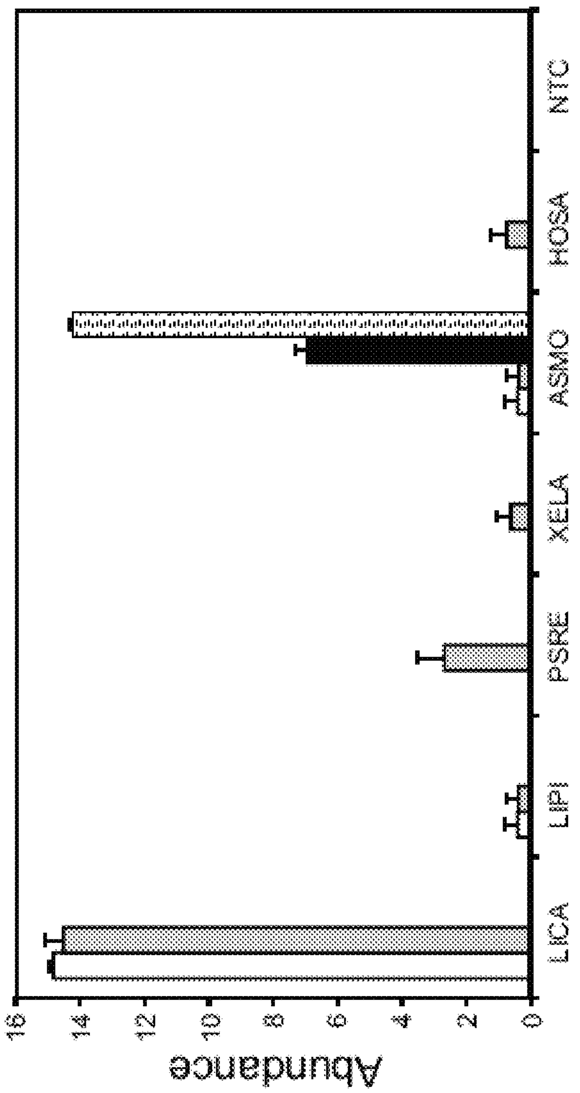
FIG. 3. Selectivity in detection following development of species-specific qPCR primer sets. The species-specific primer sets included eLICA1 (white bar), eLICA2 (grey bar), eASMO (black bar), and eASMO9 (hatched bar). DNA template included in species-specific amplification reactions comprised bullfrog (LICA), leopard frog (LIPI), tree frog (PSRE), clawed frog (XELA), tailed frog (ASMO), and human (HOSA). Additionally, all primer sets were evaluated in a qPCR reaction with no DNA template present (NTC). Multiple qPCR reactions (n=23 to 27) were performed for each primer set and DNA template combination with the mean abundance and standard error of the mean determined and presented as described in FIGS. 2A-2B.

In silico designed primer sets were next evaluated through a laboratory validation pipeline. Both eLICA1 and eLICA2 primer sets preferentially detected bullfrog total DNA compared to the other frog species investigated (FIG. 3). However, eLICA2 also demonstrated moderate amplification from tree frog and weak detection of clawed frog and human total DNA leading to reduced species specificity. The primer sets associated with tailed frog (eASMO and eASMO9) displayed strong detection of the target species total DNA with no cross-species reactivity (FIG. 3).

Figure 2B:
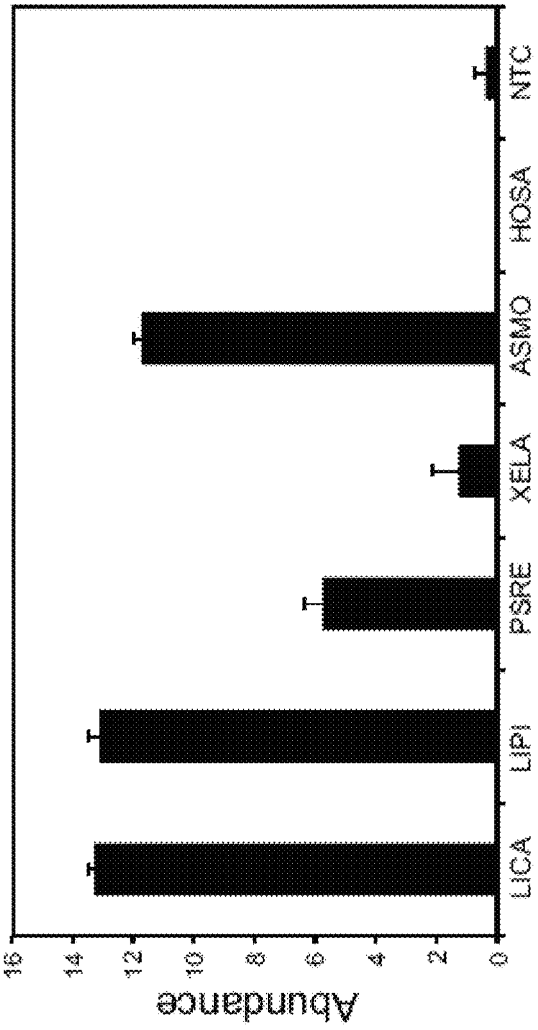

The frog group primers, eFrog2, 3, and 5 were specifically designed to work for many phylogenetically distinct frog species and to not amplify human-derived DNA. Initial evaluation showed a strong amplification signal for each of these primers. Each primer set showed detection of all five frog species tested (FIG. 2A). However, eFrog3 primers were the only ones that did not amplify human DNA (FIGS. 2A and 2B). eFrog3 primers showed the greatest level of detection for bullfrog, leopard frog, and tailed frog and the weakest for clawed frog (FIG. 2B). The latter introduced species demonstrates a highly restricted geographic distribution within North America and is not found in the wild in Canada. Therefore, eFrog3 was selected for further use as the frog group primer set.

Detection Sensitivity of eDNA Assay Tools and Empirical Determination of Technical Replicate Number Target mitochondrial gene sequences selected for eDNA assay development may exist at highly diluted concentrations in large volume aquatic systems such as lakes or riverine environs. Considering the moderate concentration factor generated by filtration and capture of total DNA material during sample preparation (~2,500 to 100,000-fold), primer sets having maximal sensitivity of detection while maintaining specificity are needed.

Effective characterization of these properties for each primer set demands a sufficient number of qPCR technical replicates be performed so that accurate detection frequencies can be measured, particularly at lower DNA template concentrations or when assay tools are directed towards total DNA originating from a potential confounder species where a weaker detection capability may exist.

This characteristic for eFrog3 and the bullfrog and tailed frog series of primer sets was determined using a species-matched dilution series of total DNA (0.008-5 μg/L) (FIGS. 4A-4B and 5A-B). 23-26 technical replicates were run at each dilution for primer set assessment which then also formed the basis for determining the number of technical replicates that can be run on field samples while still having a reasonable empirically-derived standard binomial error.

Figure 4:
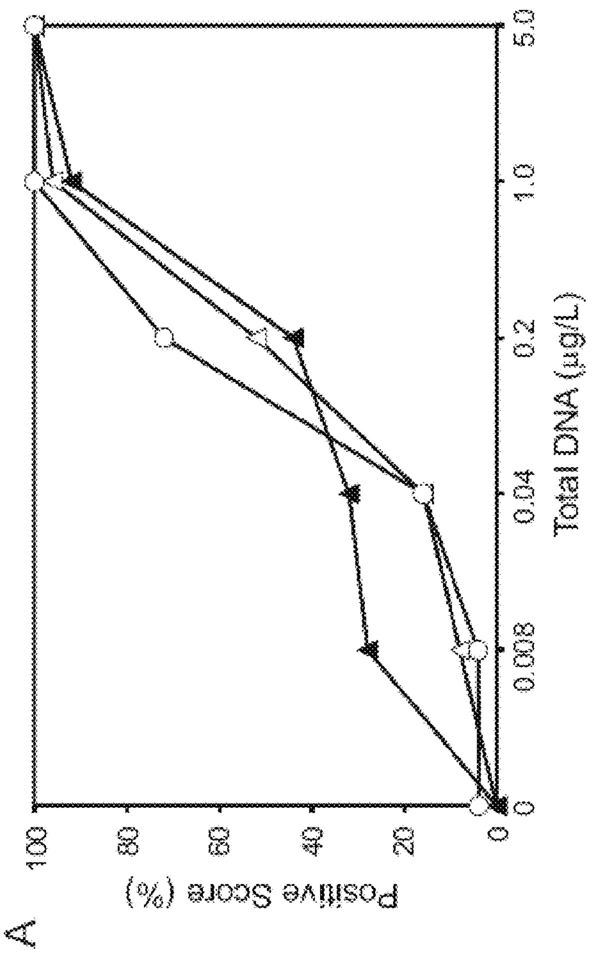
FIGS. 4A-4B. Sensitivity of species-specific and animal group qPCR primer sets for (A) bullfrog or (B) tailed frog determined using a concentration range of total DNA. A 5-fold dilution series (0.008, 0.04, 0.2, 1.0 and 5.0 μg/L) of bullfrog frog total DNA was assessed in the qPCR assay against eLICA1 (open triangle), eLICA2 (black triangle), and eFrog3 (open circle) primer sets in (A). (B) shows the results of qPCR assays against eASMO (open square), eASMO9 (black square), and eFrog3 (open circle) primer sets using tailed frog total DNA using the same 5-fold dilution series (0.008, 0.04, 0.2, 1.0 and 5.0 μg/L). The percentage of reactions demonstrating detection following 50 cycles compared to the total reactions performed (n=23-26 technical replicates) is shown. Negative control reactions containing no DNA template displayed no positive detection score with any of the assays with the sole exception of eFrog3 at 0.04% for the bullfrog template only.
Figure 4:
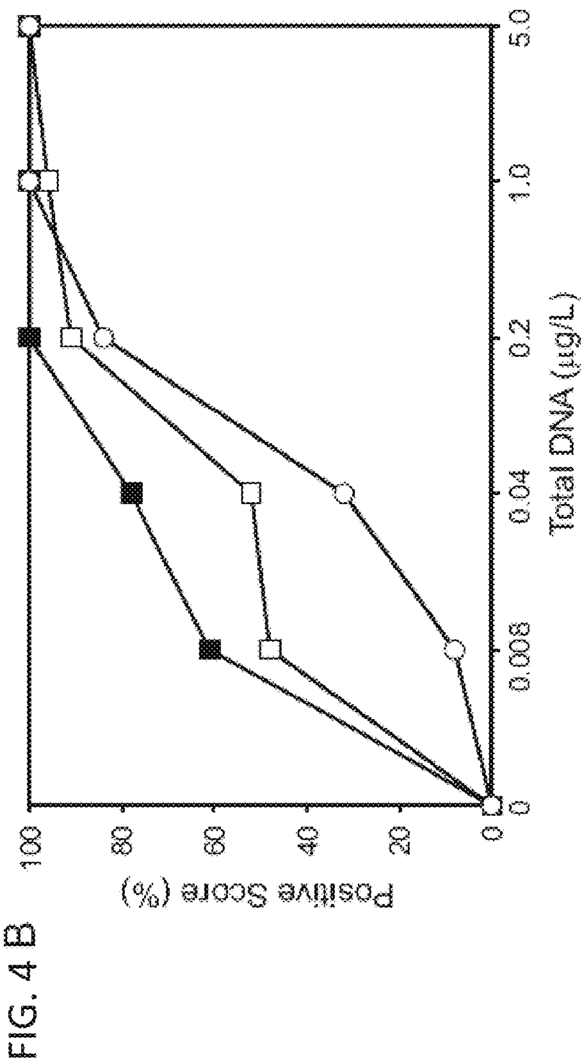

In the case of eLICA1 and eLICA2, both primer sets showed a similar ability to detect the presence of their mitochondrial gene targets at higher DNA concentrations (FIG. 4A). eLICA2 was more sensitive than eLICA1 with greater detection at a total DNA concentration of 8 ng/L (FIG. 4A). However, this primer set was not selected for use in the field because it had reduced species-specificity compared with eLICA1 (FIG. 3), which outweighs consideration of detection sensitivity. Detection of bullfrog total DNA presence was equally sensitive between eLICA1 and the eFrog3 primer sets (FIG. 4A).

A similar analysis was performed on eASMO and eASMO9 primer sets against a serial dilution of tailed frog total DNA. Positive detection was enhanced for eASMO9 compared to eASMO (61% versus 48%, respectively, at 0.008 μg/L total DNA; FIG. 4B). The eFrog3 qPCR reactions on tailed frog showed similar positive detection performance to that observed for bullfrog total DNA (FIGS. 4A and 4B). Since species specificity was comparable between eASMO and eASMO9 (FIG. 3), eASMO9 was selected due to its enhanced detection sensitivity for application to field samples.

Figure 5:
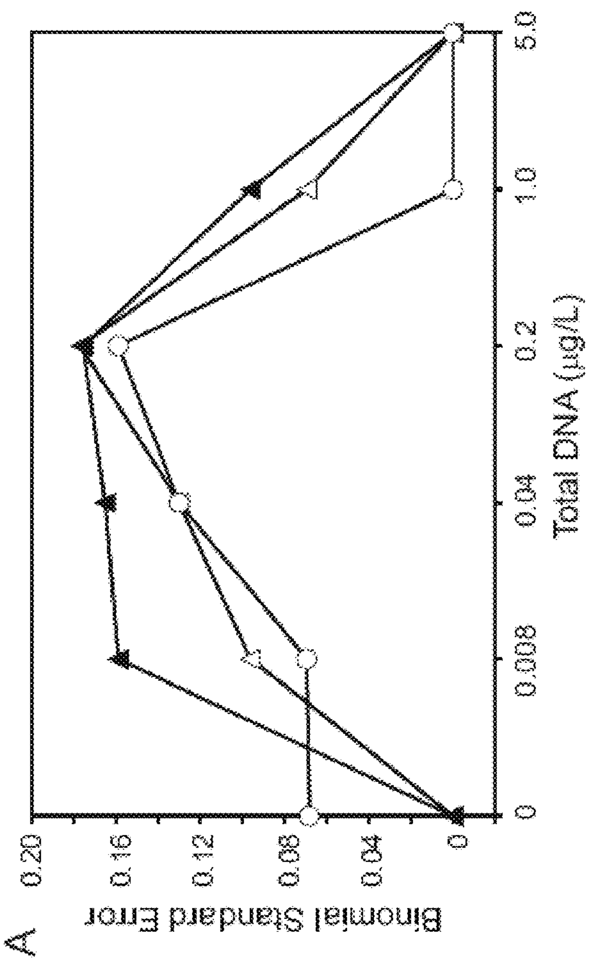
FIGS. 5A-5B. Examples of the binomial standard error calculated across a range of bullfrog total DNA concentrations (0.008-5.0 μg/L) in a qPCR assay (n=8 technical replicates) containing the primer sets in FIG. 4 for (A) bullfrog and (B) tailed frog.
Figure 5:
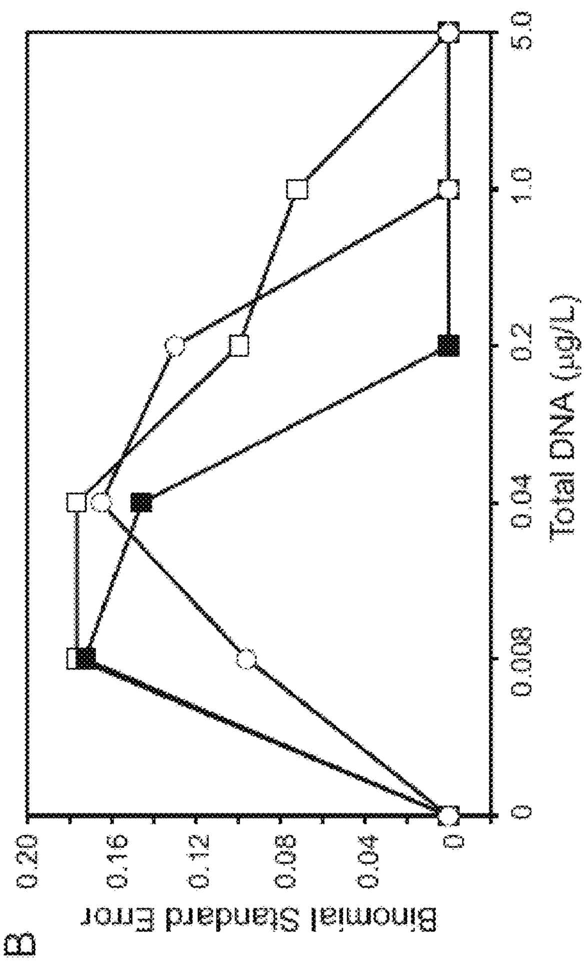

The magnitude of binomial standard error is essentially zero at either end of the dilution spectrum (i.e., greatest confidence with high amounts of target DNA present or no DNA present; FIGS. 5A-5B). However, at very low concentrations, there is a higher degree of binomial standard error. To illustrate this, the binomial standard error can be considered for 8 technical replicates as demonstrated in FIGS. 5A-5B. For each of the three primer sets tested on bullfrog, the maximal binomial standard error associated with detection was less than 0.18 across the DNA dilution series with eLICA1 (0.096) and eFrog3 (0.069) displaying reduced binomial standard error at the lowest concentrations of bullfrog total DNA examined (FIG. 5A). Binomial standard error associated with the tailed frog-specific qPCR tool validation was less than 0.018 with both candidate primer sets generating similar values at 0.008 tag/L total DNA (0.172; FIG. 5B). Error at this low DNA concentration was reduced for eFrog3 compared to the tailed frog-specific primer sets (0.096; FIG. 5B).

Knowledge of this error can be used in determining the best trade-off between choosing a reasonable number of technical replicates and the degree of confidence in the presence/"not-detected" assignation of an eDNA field sample. The effect that number of technical replicates has upon the binomial standard error at 0.04 μg/L total DNA (Table 4) was determined. From this analysis, it was determined that running eight technical replicates provides reasonable binomial standard error (<0.2 for all primer sets) while still being cost effective. Specifically, establishing the eDNA qPCR assay with eight technical replicates for each sample, rather than a triplicate, allows for reduction in binomial standard error from 0.21 to 0.13 for eLICA1, from 0.24 to 0.15 for eASMO9, and from 0.21 to 0.13 (bullfrog DNA targeted) or 0.27 to 0.17 (tailed frog DNA targeted) for eFrog3 and represents a judicious compromise between operating cost and accuracy.

TABLE 4

Effect of technical replicates on binomial standard error of all of the animal qPCR primer sets evaluated on 0.04 μg/L of total DNA isolated from the indicated species.

| Number of technical replicates | Binomial standard error[a] range | |
|---|---|---|
| | Bullfrog | Tailed frog |
| 23 or 25[b] | 0.07-0.09 | 0.09-0.10 |
| 12 | 0.11-0.13 | 0.12-0.14 |
| 8 | 0.13-0.16 | 0.15-0.18 |
| 3 | 0.21-0.27 | 0.24-0.29 |

[a]Binomial standard error = $\sqrt{(\text{proportion positive} \times \text{proportion negative})/n}$

[b]For tailed frog and bullfrog, respectively

Detection of PCR Amplifiable DNA Using ePlant5 Primers Infield-Collected Samples In addition to design considerations related to species- or group-specific detection, any false negative data that may exist in the eDNA assay data can be identified and minimized. One exemplary positive control is to confirm the proper assembly of qPCR components through the incorporation of separate positive control reaction through the use of an exogenous DNA template. This can be accomplished through the inclusion of a PCR amplicon, isolated total DNA containing mitochondrial DNA, or cDNA template prepared from isolated total RNA with the source material used to generate the template chosen to match the species specificity of the primer set in use [23]. To maintain reasonable PCR-clean technique during assay assembly, the use of the latter two positive control template sources can be used instead of a PCR amplicon.

Testing for the presence of substances that can inhibit DNA amplification has been suggested through spiking eDNA qPCR with exogenous DNA prior to performing assay runs [12]. However, this approach cannot assess whether the collected eDNA is insufficient to support PCR amplification due to possible issues with handling during sample processing (e.g., preservation method) or due to reduced template quality or degradation (e.g., by UV light or DNAses).

Figure 6:
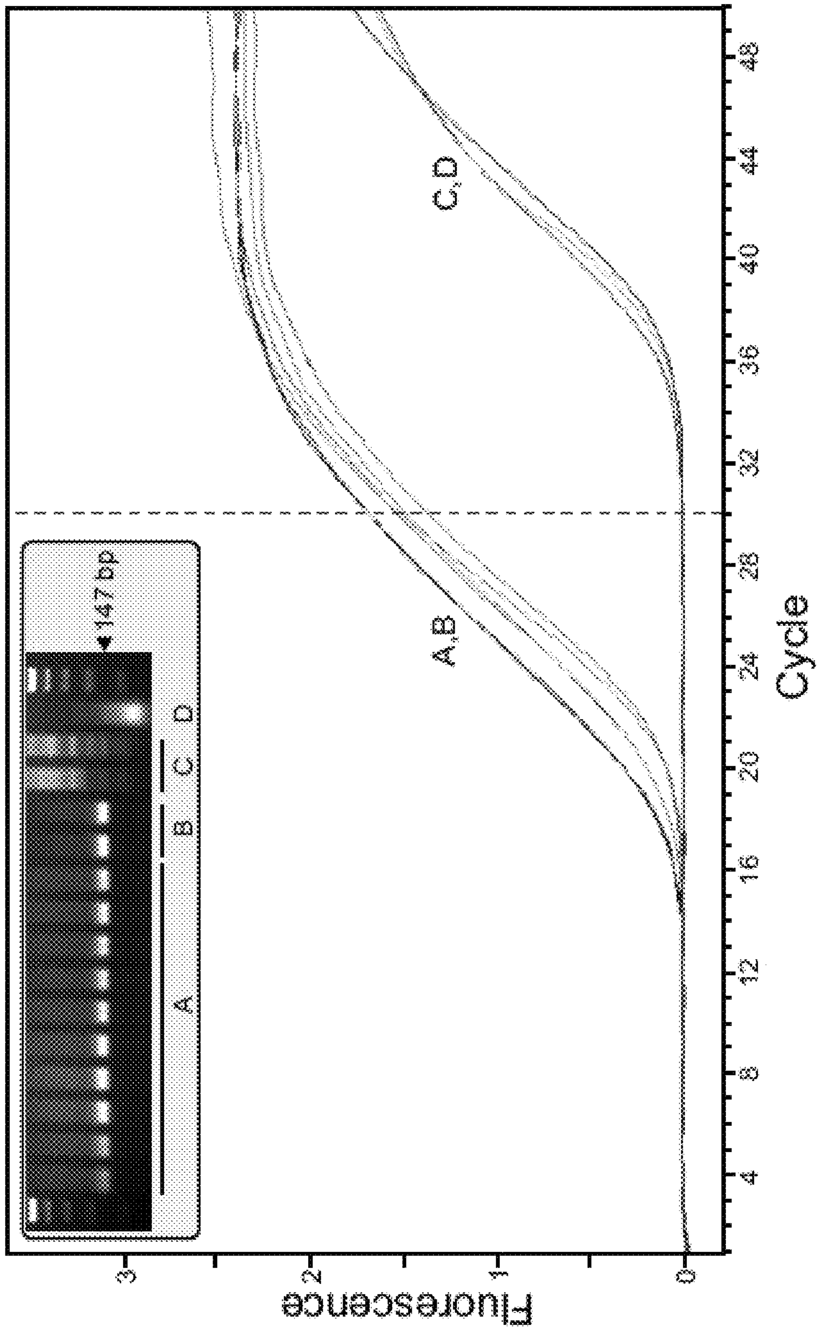
FIG. 6. Determination of the suitability of environmental samples for eDNA qPCR assessment—Part 1 of a tripartite eDNA assay. The ePlant5 primer set was used to detect a 147 base pair region of the chloroplast 23S ribosomal RNA gene. Samples were assessed in duplicate and included five different environmental water sources (A), municipal tap water (B), human total DNA (C), and distilled water (D). The dashed vertical line denotes the selected data collection cut-off for use in scoring samples based upon the presence of an amplifiable environmental DNA source.

To address the requirement for a false negative control in the eDNA assay, a component that confirms the presence of PCR amplifiable DNA material was incorporated in every eDNA sample prepared from a fresh water survey location. Chloroplasts derived from plants/algae are ubiquitously found in fresh water and primer sets were designed that detect chloroplast DNA of freshwater plant species that are widespread across North America (see Table 3). Therefore use of the ePlant5 primer set confirms that recovered total DNA is of sufficient quality to evaluate further in the eDNA assay. A typical qPCR is shown in FIG. 6, where the ePlant5 hydrolysis probe detects chloroplast 23S ribosomal RNA in environmental samples (A) or filtered tap water (B) early on (cycle<30). A delayed non-specific signal can be obtained from addition of either non-target total DNA (C; 5 μg/L human DNA) or distilled water (D) into the eDNA qPCR reaction. Using this initial data, and to eliminate the inclusion of false negatives in the ensuing assessment of the presence of animal-related eDNA, the ePlant5 assay was subsequently performed for 30 cycles (rather than 50 cycles) and the data scored as positive or negative for the presence of amplifiable DNA. All eDNA samples that score positive for ePlant5 would then be run in animal group and species-specific qPCR reactions for 50 cycles. In the present example of eDNA assessment of field-derived samples, continued evaluation of any samples identified as non-assayable by ePlant5 were allowed to highlight the potential for inclusion of false negative observations in an eDNA field survey.

Establishment of a Tripartite eDNA Assay for Field Surveys

With the different TaqMan-based primer sets validated for selectivity and sensitivity, a tripartite eDNA assay design was established that allowed for more accurate data interpretation (FIG. 7). Following collection of field samples, environmental water is precleared of gross particulate matter and total DNA captured on a 0.45 um nitrocellulose filter. This DNA material is subsequently extracted and each sample assayed for positive detection in a qPCR using the ePlant5 primer set. If the sample returns a positive score, then separate qPCR amplification reactions involving the animal group and species-specific primer sets can be performed. A negative score for ePlant5 indicates that the DNA sample is not suitable for further qPCR-based analysis. The eDNA assay, therefore, results in five possible outcomes for a given sample dependent on sample quality and primer set efficacy with respect to the particular fauna present at the sampling site (FIG. 7).

Figure 8:
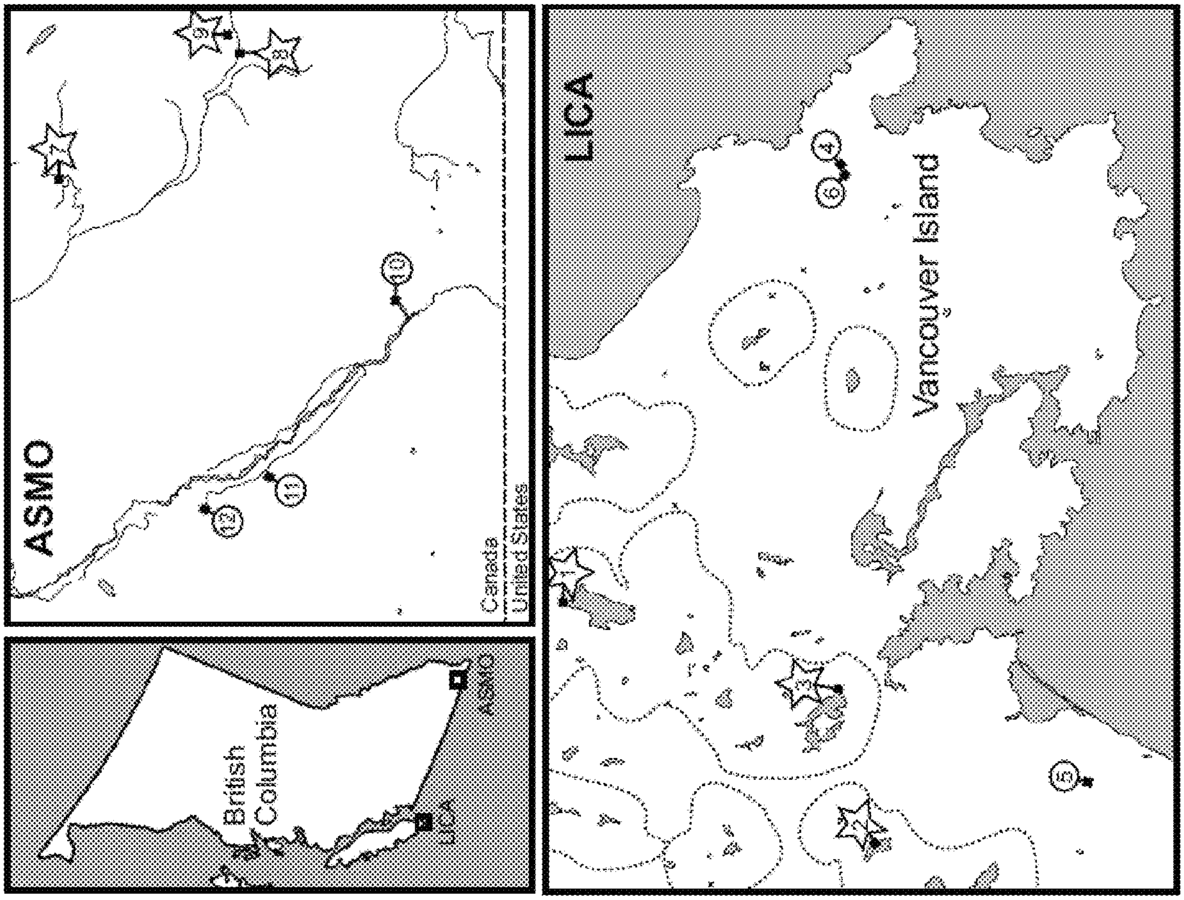
FIG. 8. Field validation of eDNA qPCR assays directed towards bullfrog and tailed frog. Sampling sites were chosen in southern British Columbia (BC), Canada, which included known locations of habitation (star) as well as regions where the target species is absent (circle). Sites selected for validation of the tailed frog eDNA assay were located in the east Kootenay region of southeastern BC. Geographic areas across south Vancouver Island outlined by a dashed line represent locales with historical populations of bullfrog (British Columbia Ministry of Environment, BC Frogwatch Atlas (maps.gov.bc.ca/ess/sv/bcfa/) and BullfrogControl.com Inc (bullfrogcontrol.com/index.html).

A field validation of the primer sets was performed. With the tripartite eDNA assay assembled, bullfrog- and tailed frog-associated regional surveys were performed within south Vancouver Island and southeastern British Columbia, respectively (Table 5; FIG. 8). Potential confounding variables may exist within the local environment under investigation that impinges upon DNA template performance and is not necessarily replicated by laboratory-isolated total DNA. This final field validation is used to establish a functional scoring schema that mitigates against miscalls; the yes/no (Y/N) decision boundary for a given primer set must be determined with field samples from locations of known extant habitation (to assess false negative score rates) as well as sites where absence of the target species is confirmed (to assess false positive score rates). Six sites on Vancouver Island were visited with two 250 mL water samples collected at each locale to test for bullfrogs (Table 5; FIG. 8). For tailed frog field evaluation, six sites in Southeastern British Columbia were visited with two 1000 mL water samples collected at each locale (Table 5; FIG. 8).

TABLE 5

Field validation of species-specific eDNA assays directed towards bullfrog and tailed frog.

| | | | | eDNA Assay[c] (Amplification Frequency, Score) | | | Binomial Error | | |
|---|---|---|---|---|---|---|---|---|---|
| | | | UTM Coordinates | | | | | | |
| | Site | | (Zone, Easting, | PCR | | | | | |
| Species | Characteristics[a] | Site Name | Northing) | Control | Group | Species | PCR | Group | Species |
| LICA | +, 1, 1 | Prospect Lake[b] | 10, 467468, 5374224 | 8/8, Y | 8/8, Y | 8/8, Y | 0.000 | 0.000 | 0.000 |
| | +, 1, 2 | Prospect Lake[b] | 10, 467530, 5374284 | 8/8, Y | 8/8, Y | 8/8, Y | 0.000 | 0.000 | 0.000 |
| | +, 2, 1 | Florence Lake | 10, 462438, 5367400 | 8/8, Y | 3/8, Y | 3/8, Y | 0.000 | 0.171 | 0.171 |
| | +, 2, 2 | Florence Lake | 10, 462111, 5367587 | 8/8, Y | 3/8, Y | 4/8, Y | 0.000 | 0.171 | 0.177 |
| | +, 3, 1 | Thetis upper pond[b] | 10, 465667, 5368089 | 8/8, Y | 8/8, Y | 8/8, Y | 0.000 | 0.000 | 0.000 |
| | +, 3, 2 | Thetis upper pond[b] | 10, 465668, 5368120 | 8/8, Y | 8/8, Y | 8/8, Y | 0.000 | 0.000 | 0.000 |
| | −, 4, 1 | Finnerty Gardens | 10, 476507, 5367602 | 8/8, Y | 2/8, N | 0/8, N | 0.000 | 0.153 | 0.000 |
| | −, 4, 2 | Finnerty Gardens | 10, 476507, 5367602 | 8/8, Y | 1/8, N | 1/8, N | 0.000 | 0.117 | 0.117 |
| | −, 5, 1 | Murrays Pond | 10, 463432, 5362205 | 0/8, N | 0/8, N | 0/8, N | 0.000 | 0.000 | 0.000 |
| | −, 5, 2 | Murrays Pond | 10, 463473, 5362236 | 8/8, Y | 2/8, N | 1/8, N | 0.000 | 0.153 | 0.117 |
| | −, 6, 1 | Mystic Vale | 10, 477246, 5367413 | 8/8, Y | 1/8, N | 2/8, N | 0.000 | 0.117 | 0.153 |
| | −, 6, 2 | Mystic Vale | 10, 477266, 5367383 | 8/8, Y | 1/8, N | 0/8, N | 0.000 | 0.117 | 0.000 |
| ASMO | +, 7, 1 | Upper Bighorn Trib 4[b] | 11, 665595, 5448057 | 8/8, Y | NA, NA | 8/8, Y | 0.000 | NA | 0.000 |
| | +, 7, 2 | Upper Bighorn Trib 4[b] | 11, 665595, 5448057 | 8/8, Y | NA, NA | 7/8, Y | 0.000 | NA | 0.117 |
| | +, 8, 1 | Cabin Trib 1[b] | 11, 671189, 5440590 | 8/8, Y | NA, NA | 5/8, Y | 0.000 | NA | 0.171 |
| | +, 8, 2 | Cabin Trib 1[b] | 11, 671189, 5440590 | 8/8, Y | NA, NA | 8/8, Y | 0.000 | NA | 0.000 |
| | +, 9, 1 | Storm 1 | 11, 672736, 5441352 | 8/8, Y | NA, NA | 8/8, Y | 0.000 | NA | 0.000 |
| | +, 9, 2 | Storm 1 | 11, 672736, 5441352 | 8/8, Y | NA, NA | 8/8, Y | 0.000 | NA | 0.000 |
| | −, 10, 1 | Desolation 1 | 11, 661140, 5434077 | 8/8, Y | NA, NA | 0/8, N | 0.000 | NA | 0.000 |
| | −, 10, 2 | Desolation 1 | 11, 661140, 5434077 | 8/8, Y | NA, NA | 0/8, N | 0.000 | NA | 0.000 |
| | −, 11, 1 | Wigwam West Trib 1 | 11, 654157, 5439325 | 8/8, Y | NA, NA | 0/8, N | 0.000 | NA | 0.000 |
| | −, 11, 2 | Wigwam West Trib 1 | 11, 654157, 5439325 | 8/8, Y | NA, NA | 0/8, N | 0.000 | NA | 0.000 |
| | −, 12, 1 | Wigwam West Trib 2 | 11, 652487, 5441825 | 8/8, Y | NA, NA | 0/8, N | 0.000 | NA | 0.000 |
| | −, 12, 2 | Wigwam West Trib 2 | 11, 652487, 5441825 | 8/8, Y | NA, NA | 0/8, N | 0.000 | NA | 0.000 |

[a]Sample characteristics include location type, which denotes a site of known presence (+) or absence (−) of the target species, site number, and water sample replicate.
[b]Visual and/or auditory confirmation of the presence of adult frogs or larval tadpoles was established at this sampling site.
[c]Primer sets associated with the PCR control and animal group were ePlant5 and eFrog3, respectively. Detection of bullfrog and tailed frog species used eLICA1 and eASMO9 primer sets, respectively. Positive detection (Y) is represented by a qPCR amplification frequency greater than 2/8 while ≤2/8 was scored as species absent (N) from the site.
NA; not applicable.
UTM, Universal Transverse Mercator.

In order to establish confidence in a positive detection, the minimum number of positive technical qPCR replicates required to support the observation can be determined. The extreme demands upon qPCR with low concentrations of DNA template and high thermocycle number (50 cycles for the frog primer sets; see Example 2) in the eDNA assay renders an increased likelihood for the occasional spurious amplification and/or non-targeted release of fluor signal, even under PCR-clean conditions. To investigate potential noise in the assay, the results from field sites where the target species were highly unlikely to be present was evaluated. Filters through which only distilled water was filtered were also examined. Based upon such replicate qPCR data for both bullfrog and tailed frog, it was determined that a negative detection (N) is established when signal is detected from ≤2 out of 8 qPCR replicates (Table 5). Therefore, a positive species detection score (Y) would be assigned if the signal-detected qPCR replicates were greater than 2 out of 8 for a given environmental sample.

The average recovery of total DNA from a half filter following the filtration and DNA isolation procedures was 12.5 ng/μL (range 8-17 ng/μL; n=12). The exogenous positive control present in all eDNA assay runs confirmed successful assembly and execution of the qPCR. Sites 1, 2, and 3 were independently observed to have bullfrogs present through visual and auditory observation during collections, whereas sites 4, 5, and 6 were locales where there are no known detections of bullfrog (FIG. 8 and Table 5). The DNA PCR amplification control (ePlant5-based test) was positive for all samples with one exception (Table 5). Of these, sites 1-3 tested positive for the presence of frogs (group) and bullfrogs (species) (FIG. 8 and Table 5) and sites 4, 5, and 6 were negative for frogs and bullfrogs (FIG. 8 and Table 5). Although the total DNA amount obtained from both replicates of site 5 were comparable (11 and 12 ng/μL), replicate 1 failed the test for the presence of qPCR amplifiable material (ePlant5 negative) and was consequently found negative for detection of animal group or bullfrog (Table 5). Although, in this instance, an appropriate lack of detection at site 5 was borne out from the replicate water sample, it is clear that without the ePlant5 evaluation, naïve incorporation of a false negative at sites 1-3 could lead to increased difficulty in scoring for the group- and species-specific evaluations. The three locations which demonstrated positive scores in the bullfrog eDNA assay are situated in regions of known extant bullfrog habitation (FIG. 8).

One interesting outcome of the field validation for bullfrog relates to Florence Lake. This aquatic feature is situated in a regional control corridor established for the prevention of further spread of this introduced invasive species on southern Vancouver Island. An active removal program spanning a five year period (2007-2011) resulted in a reduction of 4,675 adult bullfrog in Florence Lake and 14,000 individuals throughout the region [24]. The analysis in the summer of 2015 indicates that such actions failed to eliminate this species from the lake habitat (see Table 5) which is likely due to incomplete eradication and/or a recolonization of the area.

The average recovery of total DNA from the tailed frog-associated field survey was 7.3 ng/μL (range 2-14 ng/μL; n=12). All samples prepared from sites 7 to 12 tested positive for PCR amplification using the ePlant5 primer set and were advanced for further eDNA analysis (Table 5). The three sites of known habitation for tailed frog (confirmed visually during sampling; sites 7, 8, and 9) tested positive for the presence of the species but were negative for the frog group (Table 4, FIG. 8). Sites 10 through 12, demonstrating absence of tailed frog using conventional search methods during and preceding sample collection, tested negative in the eDNA assay using both the general frog primer set (eFrog3) and tailed frog-specific primer set.

While reasonable performance of eFrog3 in detection of tailed frog DNA was observed under laboratory conditions (see FIG. 1A) and in the field survey for detection of the presence of bullfrog, use of this primer set for determining the presence of any frog species at the southern BC field locations demonstrated no detection data. This may be due to insufficient amplification strength by eFrog3 for certain target species when challenged with field-derived eDNA. However, it may also reflect the low likelihood of significant occupation within the southeastern BC test sites examined by other frog species as tailed frog habitat requirements exclude sympatry with other anurans; this is consistent with differences in habitat preferences of tailed frog (lotic) versus of other species (lentic/wetland).

qPCR has the potential to permit quantification of the starting DNA within a sample. However, currently available approaches are not capable of providing a reliable quantitative measure to estimate relative abundance of target taxa at different locales despite the great interest in obtaining such information to derive indices of relative organismal abundance. This is due to potential change in known and unidentified environmental factors along with the unknown influence of several biological variables [11,13]. Environmental factors include consideration of site-specific characteristics that influence degradation of DNA in natural systems including, most notably, temperature and exposure to UV radiation. Other influential environmental variables include differing hydrological conditions between sites.

Biological variables that may impact an eDNA assay-derived determination of species abundance at survey sites include unknown distances to target taxa (i.e., point sources of eDNA), indefinite abundance of target and confounding non target taxa at a given site, and unknown emission rates (i.e., species exude DNA at different rates into the environment and, even for a given species, DNA can be released at dissimilar rates during different lifecycle phases). Moreover, a qPCR-associated estimation of animal numbers is typically derived following comparison to a standard curve generated from a known quantity of purified total DNA. However, such an estimate depends upon the amount of mitochondrial sequence disseminated into the local environment at each location under investigation. The abundance of mitochondria differs between tissue types leading to potential complexity with respect to the original source of signal (mitochondrial DNA deposition rates) between sites. For example, an anadromous salmon survey that compares sites where species-specific eDNA dissemination derives primarily from skin versus a spawning region, where dissemination could be increased from muscle tissue breakdown (during semelparity) could not necessarily be compared with the assumption that signal differences are associated solely with differing animal numbers at the two sites. The same reasoning holds true for evaluation of differing lentic sites inhabited by a given anuran species where one location contains significant egg masses compared to the other. Thus, the quantitative aspect of qPCR in some examples is not exploited in the disclosed eDNA assay. The disclosed eDNA methods increase species specificity.

In summary, the disclosed eDNA assay includes steps that help characterize the nature of the test sample and allow for increased accuracy in data interpretation with minimal false assumptions playing a significant role. The work flow for the disclosed tripartite eDNA assay is depicted in FIG. 7 with informed assay outcomes, and a summary of the design, validation, and execution of a qPCR-based eDNA assessment is provided in Table 6. The current methods provide enhanced quality and performance of qPCR-based eDNA assays thereby allowing greater context and interpretive power in their use under varied field survey conditions.

TABLE 6

Stepwise approach in the design, validation, and execution of qPCR-based eDNA assessment.

| Development Phase | Step | Considerations and reporting |
|---|---|---|
| In silico | 1 | Available information on mitochondrial gene sequences for the target species and related potential confounder species (including *Homo sapiens*) are obtained and DNA alignments performed. |
| | 2 | Primers are designed for three eDNA assay components: (1) confirmation of the presence of assayable eDNA and subsequent detection of (2) the animal group and (3) the individual species of interest. Primer design considerations include using a 3-step thermocycle program with selection of a stringent annealing temperature for evaluation of primer sets compatible with TaqMan-based detection of DNA amplification. Sequence positions of variation between species are exploited or avoided depending upon the desired features for each assay component. Species used in design are reported. |
| In vitro | 3 | Each amplification primer pair is initially evaluated using species-matched purified total DNA for production of the target DNA amplicon with a reasonable level of reduced background (spurious) amplification under the extended PCR cycles required for eDNA assessment. |
| | 4 | TaqMan hydrolysis probes are subsequently evaluated for contribution to enhanced signal quality and reduced noise in a qPCR with species-matched purified total DNA. |
| | 5 | Amplification specificity is confirmed towards total DNA from the target species and against comparable related species and *Homo sapiens*. The correct identities of the DNA amplicon products from all TaqMan-based qPCR reactions are confirmed by direct sequencing or restriction endonuclease mapping. |
| | 6 | Amplification sensitivity for each primer set is evaluated with a dilution series of purified total DNA from the target species. |
| In situ | 7 | A tripartite eDNA assay is assembled as per the requirements of the field-based survey. This includes a no template negative control and a positive interrun control consisting of either appropriate purified amplicon template or total cDNA. |
| | 8 | Functional validation of the eDNA assay is carried out with environmental water samples collected from known positive and negative field locations for every study. |

Example 4

Chloroplast DNA as a Positive Control

A DNA source that is ubiquitous in all samples analyzed can act as an endogenous verifier that the isolated DNA from an environmental sample was capable of supporting qPCR amplification and detection. For freshwater samples, paramecium is commonly found in ponds, lakes, and streams. However, it was observed that primer sets and probes specific for four paramecium mitochondrial genes, cytochrome oxidase I, 5S rRNA, cytochrome B, and NADH dehydrogenase subunit 1 provided unsatisfactory results.

Primer sets and probes specific for chloroplast DNA found in plants and algae were developed, and were found to provide successful positive controls for freshwater samples (see Tables 3 and 6).

Example 5

Additional Exemplary Primers and Probes

Table 7 and FIGS. 9-20 show additional primer/probe set designs that can be used in the disclosed assays. They have been designed to exclude human as a confounder. These include primer/probe sets for detecting the amphibian (FIG. 9) or mammal animal group (FIG. 10) and frog, toad, and shrew species: *Anaxyrus* (*Bufo*)*boreas* (Western toad; ANBO; FIG. 11), *Ascaphus montanus* (Rocky Mountain tailed frog; ASMO; FIG. 12), *Ascaphus truei* (Pacific (Coastal) tailed frog; ASTR; FIG. 13), *Lithobates* (*Rana*) *catesbeiana* (North American bullfrog; LICA; FIG. 14), *Lithobates pipiens* (Northern leopard frog; LIPI; FIG. 15), *Rana aurora* (Northern red-legged frog; RAAU; FIG. 16), *Rana cascadae* (Cascades frog; RACA; FIG. 17), *Rana luteiventris* (Columbia spotted frog; RALU; FIG. 18), *Rana pretiosa* (Oregon spotted frog; RAPR; FIG. 19), or *Sorex bendirii* (Pacific water shrew; SOBE; FIG. 20).

The above (FIGS. 9-20) and additional primer/probe sets are shown in Table 7 including Pan amphibian, Pan fish, Pan Fungus and the specific amphibian and fish species: *Lithobates sylvaticus* (Wood frog; LISY), *Cottus cognatus* (Slimy sculpin; COCO), *Prosopium cylindraceum* (Round whitefish; PRCY), *Salvelinus malma* (Dolly Varden, SAMA), *Thymallus arcticus* (Arctic grayling; THAR), *Oncorhynchus tschawytscha* (Chinook salmon; ONTS), *Oncorhynchus kisutch* (Coho salmon, ONKI), or *Dicamptodon tenebrosus* (Giant Pacific salamander, DITE).

TABLE 7

Characteristics of PCR primers for use in eDNA assays. These primer sets do not amplify human DNA.

| Species | Common Name | Species Code | Gene | Primer Set | Primer Name | Primer Sequence (SEQ ID NO:) | Amp-licon size |
|---|---|---|---|---|---|---|---|
| Mammals except human | Mammals except human | Mammal | MT-RNR1 | eMammal1 | 160051 | AAAGGACTTGGCGGTRCTTT (25) | 433 |
| | | | | | 160052 | CCAAGCACACTTTCCAGTATG (26) | |
| | | | | | 160120 Probe | ATGAAGYACGCACACACCGCCCG (27) | |
| *Anaxyrus* (*Bufo*) *boreas* | Western toad | ANBO | MT-CYB | eANBO4 | 160017 | TATACTATGGCTCATACCTC (28) | 219 |
| | | | | | 160018 | GGTTGCGTTATCTACCGAG (29) | |
| | | | | | 160039 Probe | TTAGTTATAGCCACAGCGTTTGTGGG (30) | |
| *Ascaphus truei* | Pacific (coastal) tailed frog | ASTR | MT-CYB | eASTR4 | 160006 | GAACATTGGCATTATCCTACTT (31) | 202 |
| | | | | | 160007 | AGGCGAAAAATCGTGTTAAC (32) | |
| | | | | | 160106 Probe | CGCTTTTGTAGGGTATGTGTTACCG (33) | |
| *Lithobates pipiens* | Northern leopard frog | LIPI | MT-RNR1 | eLIPI1 | 160109 | AGCTTACCATGTGAACGTCTT (34) | 163 |
| | | | | | 160110 | TACTACTAAATCCACCTTCGCT (35) | |
| | | | | | 160118 Probe | CAATTGGCTACAATTTCTAATATAGAACAA (36) | |
| *Rana aurora* | Northern red-legged frog | RAAU | MT-RNR2 | eRAAU1 | 160021 | TGAAGAAGCGGGAATCAAA (37) | 104 |
| | | | | | 160022 | GCATACAGATTTCTTGTGTGTG (38) | |
| | | | | | 160040 Probe | TAAACTCATCATACACCTCTGTGCTC (39) | |
| *Rana cascadae* | Cascades frog | RACA | MT-CYB | eRACA2 | 160030 | CCTAATTGCCCAAATCGCT (40) | 304 |
| | | | | | 160031 | CTCAAAATGACATCTGGCCC (41) | |
| | | | | | 160099 Probe | TGGCTGGCTCCTTCGTAATTTACATG (42) | |
| *Rana luteiventris* | Columbia spotted frog | RALU | MT-NDI | eRALU2 | 160047 | TTCCTCTACCAATCCCCTAT (43) | 203 |
| | | | | | 160048 | CCAGGAAAACAGTGCATAAG (44) | |
| | | | | | 160095 Probe | CAGCCTAACCGTTTACACAATTTTGGG (45) | |
| *Rana pretiosa* | Oregon spotted frog | RAPR | MT-CYB | eRAPR2 | 160085 | GTAACCTCCATGCTAACGGT (46) | 134 |
| | | | | | 160086 | CTATCACTAGGAATAGGAGGATC (47) | |
| | | | | | 160096 Probe | TTTCCACATCGGCCGAGGCCTC (48) | |
| *Sorex bendirii* | Pacific water shrew | SOBE | MT-CYB | eSOBE4 | 160100 | AAACATGAAACATCGGAGTAC (49) | 234 |
| | | | | | 160101 | ATAATGAAAGGTAGGATAAAA (50) | |
| | | | | | 160108 Probe | CGCAACAGTAATTACAAACCTACTATCA (51) | |
| Amphibia | Pan amphibian | xAmphibian | MT-RNR2 | eFROG8 | 160036 | GARGGYTATACTGTCTCC (52) | 299 |
| | | | | | 160035 | ATCCCYAGGGTAACTTGG (53) | |
| | | | | | 160044 Probe | ATAAGACGAGAAGACCCYATGGAGCT (54) | |
| Fish | Pan fish | Fish | MT-RNR1 | eFish1 | 160083 | CACCTAGAGGAGCCTGTTCTA (55) | 152 |
| | | | | | 160084 | CTACACCTCGACCTGACGTT (56) | |
| | | | | | Fish1 Probe | TATATACCRCCGTCGTCAGCTTACCC (57) | |
| Fungi | Pan Fungus | Fungi | MT-CYB | eFungi1 | eFungi1up | AGTACCTGAATGATATTTATTACC (58) | 244 |
| | | | | | eFungi1dn | TTCTATAAATGGACTTTCAACG (59) | |
| | | | | | eFungi1 Probe | CTAGAGGTTTACAATTCAGACCTTTAAG (60) | |
| | | | | eFungi2 | eFungi2up | CTAATGCTGTAGGTTACTATGG (61) | 526 |
| | | | | | eFungi2dn | CCACTAACTAACTCAGATTCAG (62) | |
| | | | | | eFungi2 Probe | CTTTCTTAGGGTCATTAAGGAGTAC (63) | |
| *Lithobates* (*Rana*) *sylvaticus* | Wood frog | LISY | MT-CYB | eLISY1 | LISY1up | TCTATCGCACACATCTGTCGA (64) | 289 |
| | | | | | LISY1dn | ACTAGGTCGGAGCCAATATAG (65) | |
| | | | | | Probe | TTACTACGGCTCTTATCTTTATAAAG (66) | |
| *Cottus cognatus* | Slimy Sculpin | COCO | MT-RNR1 | eCOCO1 | 160071 | TAAAGCCAAACATCTTCAAGA (67) | 167 |
| | | | | | 160072 | GCGGATAGTGGGTGTGTAGTA (68) | |
| | | | | | COCO1 Probe | TCGCTTTATCTGATCTGAATCCACGAA (69) | |
| | | | MT-CYB | eCOCO2 | 160073 | CCTCGGTCTTTGCTTAATTAT (70) | 280 |
| | | | | | 160074 | CTACGAAAGCGGTTATTATTAC (71) | |
| | | | | | COCO2 Probe | ATCAGTTGGTCATATTTGCCGAGATG (72) | |
| | | | MT-CYB | eCOCO3 | 160075 | CAGTTCCTTACATTGGCAA (73) | 255 |
| | | | | | 160076 | ATTAAGAGCGCTGCAAAG (74) | |
| | | | | | COCO3 Probe | CCTTGGTTTAAACTCAGATGCAGACAA (75) | |

TABLE 7-continued

Characteristics of PCR primers for use in eDNA assays. These primer sets do not amplify human DNA.

| Species | Common Name | Species Code | Gene | Primer Set | Primer Name | Primer Sequence (SEQ ID NO:) | Amplicon size |
|---|---|---|---|---|---|---|---|
| *Prosopium cylindraceum* | Round Whitefish | PRCY | MT-RNR2 | ePRCY1 | 160077 | AAGAAAAGCCTGCACAAATAT (76) | 552 |
| | | | | | 160078 | GTCCGTTGATCGGCATTT (77) | |
| | | | | | PRCY1 Probe | CTAACAAGTAAAAACGCAGTGACCCCT (78) | |
| | | | MT-CYB | ePRCY2 | 160079 | CTCAAATCCTTACAGGGTTG (79) | 328 |
| | | | | | 160080 | CGCGGAGAGTAGATTTGTAATA (80) | |
| | | | | | PRCY2 Probe | TCGGGACGTAAGCTACGGCTGAC (81) | |
| | | | MT-ND1 | ePRCY3 | 160081 | GCCCATCGCAGATGGTA (82) | 322 |
| | | | | | 160082 | TAATTACGCTAAGTAAAATAAGC (83) | |
| | | | | | PRCY3 Probe | CGTGCTTGCACTCTCCAGCCTAGC (84) | |
| *Salvelinus malma* | Dolly Varden | SAMA | MT-RNR2 | eSAMA1 | 160089 | GGGCTTAGCTGTCTCCTCTC (85) | 157 |
| | | | | | 160090 | CTAGGGGTCACTGCGTTTC (86) | |
| | | | | | eSAMA1 Probe | TACATAAGACGAGAAGACCCTATGGAGCT (87) | |
| | | | MT-CYB | eSAMA2 | 160091 | TTACATACATATCGCCCGG (88) | 365 |
| | | | | | 160092 | TCGGCGTCGGAGTTAATA (89) | |
| | | | | | eSAMA2 Probe | CTTCGTTATTGCAGCCGCCACAGT (90) | |
| | | | MT-ND1 | eSAMA3 | 160093 | CCAAACCTTCAACGTAGCT (91) | 159 |
| | | | | | 160094 | GTATTCTACGTTGAATCCTGAA (92) | |
| | | | | | eSAMA3 Probe | CTTGGCCGAAACAAACCGTGC (93) | |
| *Thymallus arcticus* | Arctic Grayling | THAR | MT-RNR1 | eTHAR1 | 160055 | GAGAGGCCCAAGTTGATAGT (94) | 402 |
| | | | | | 160056 | ACCCATTTTGCTTACTATATGA (95) | |
| | | | | | eTHAR1 Probe | CCCCTGAACCCACGACAGCTATG (96) | |
| | | | MT-RNR2 | eTHAR2 | 160057 | CCCACACAGGAGTGCAAG (97) | 367 |
| | | | | | 160058 | TGCGTTTTTACTTGGTAGGA (98) | |
| | | | | | eTHAR2 Probe | ATATAAGAGGTCCCGCCTGCCCTGT (99) | |
| | | | MT-ND1 | eTHAR3 | 160059 | ATCTCCTACGAGGTTAGTTTG (100) | 392 |
| | | | | | 160060 | AAATACTACGGATAGTAGAGCC (101) | |
| | | | | | eTHAR3 Probe | TGAACTAGTCTCCGGATTCAATGTAGAA (102) | |
| *Oncorhynchus tschawytscha* | Chinook Salmon | ONTS | MT-RNR1 | eONTS1 | 160063 | ACCTAGAGGAGCCTGTTCTAT (103) | 209 |
| | | | | | 160064 | GCGTGGTTCGTAGTACTCTAG (104) | |
| | | | | | eONTS1 Probe | TCCATAGTAAGCAAAATGGACAAAACCC (105) | |
| | | | MT-RNR2 | eONTS2 | 160065 | CGACCGAAAAGGAGACAAA (106) | 342 |
| | | | | | 160066 | CCTCAAGGTCCTAAGAAAGCT (107) | |
| | | | | | eONTS2 Probe | ATTTTAAGCCTAGAAAAGCAGAGATTAAA (108) | |
| | | | MT-CYB | eONTS3 | 160067 | CGAGGACTTTATTATGGCTCT (109) | 386 |
| | | | | | 160068 | ATCTTTGTATGAGAAGTAGGGA (110) | |
| | | | | | eONTS3 Probe | CTGAGGCGGGTTCTCTGTTGACAAC (111) | |
| *Oncorhynchus kisutch* | Coho Salmon | ONKI | MT-RNR1 | eONKI1 | eONKI1up | ATAATAACTGCCTTTGTGGGA (112) | 367 |
| | | | | | eONKI1dn | GCAAAAAGAGCTAAGGATGTC (113) | |
| | | | | | eONKI1 Probe | TACTCTAACACGATTTTTCGCCTTTCAC (114) | |
| | | | MT-RNR1 | eONKI2 | eONKI2up | CTTGTCCTTATGGTTGTACCA (115) | 203 |
| | | | | | eONKI2dn | TGAAAGAACTAGGAAGATGGC (116) | |
| | | | | | eONKI2 Probe | TTAACCTGAATCGGGGGCATGCC (117) | |
| | | | MT-ND1 | eONKI3 | eONKI3up | CACATCCCCGCTTTACCA (118) | 208 |
| | | | | | eONKI3dn | GGAGGGAGGCCTGCTAGG (119) | |
| | | | | | eONKI3 Probe | ATCACCCTGGCCCTTGTACTGTGG (120) | |
| | | | MT-ND1 | eONKI4 | eONKI4up | CCCTTTTGACCTCACAGAG (121) | 196 |
| | | | | | eONKI4dn | GGTTCAGGGCAGTTAGTTCT (122) | |
| | | | | | eONKI4 Probe | TGCCCTCTTTTTCCTAGCCGAGTACG (123) | |
| *Dicamptodon tenebrosus* | Giant Pacific Salamander | DITE | MT-CYB | eDITE1 | eDITE1up | AGGCGCAACAGTTATCACG (124) | 211 |
| | | | | | eDITE1dn | AATGCCATGTTGGGTTATTAGA (125) | |
| | | | | | eDITE1 Probe | ATTGCCCTTAGTATTATTCATCTTTT (126) | |
| | | | | eDITE2 | eDITE2up | CATTATACTGCTGATACTAT (127) | 216 |
| | | | | | eDITE2dn | CTATCATTAATAGTAATAAGATC (128) | |
| | | | | | eDITE2 Probe | TATCTACTATGGGTCATATTTATATAA (129) | |

REFERENCES

1. Somerville et al. (1989) Simple, rapid method for direct isolation of nucleic acids from aquatic environments. Appl Environ Microbiol 55: 548-554.
2. Rees et al. (2014) The detection of aquatic animal species using environmental DNA—a review of eDNA as a survey tool in ecology. J Appl Ecol 51: 1450-1459.
3. Thomsen et al. (2012) Monitoring endangered freshwater biodiversity using environmental DNA. Mol Ecol 21: 2565-2573.
4. Pilliod et al. (2014) Factors influencing detection of eDNA from a stream-dwelling amphibian. Mol Ecol Resour 14: 109-116.
5. Turner et al. (2015) Fish environmental DNA is more concentrated in aquatic sediments than surface water. Biol Conserv 183: 93-102.

6. Goldberg et al. (2015) Moving environmental DNA methods from concept to practice for monitoring aquatic macroorganisms. Biol Conserv 183: 1-3.
7. Baird D J, Hajibabaei M (2012) Biomonitoring 2.0: a new paradigm in ecosystem assessment made possible by next-generation DNA sequencing. Mol Ecol 21: 2039-2044.
8. Takahara T, Minamoto T, Doi H (2013) Using environmental DNA to estimate the distribution of an invasive fish species in ponds. PLoS One 8: e56584.
9. Thomsen P F, Willerslev E (2015) Environmental DNA—An emerging tool in conservation for monitoring past and present biodiversity. Biol Conserv 183: 4-18.
10. Peterson et al. (2013) Investigating the dispersal routes used by an invasive amphibian, *Lithobates catesbeianus*, in human-dominated landscapes. Biol Invasions 15: 2179-2191.
11. Herder et al. (2014) Environmental DNA—a review of the possible applications for the detection of (invasive) species. Nijmegen: Netherlands Food and Consumer Product Safety Authority. 111 pp.
12. Goldberg et al. (2016) Critical considerations for the application of environmental DNA methods to detect aquatic species. Meth Ecol Evol., 7:1299-307 DOI: 10.1111/2041-210X.12595.
13. Strickler et al. (2015) Quantifying effects of UV-B, temperature, and pH on eDNA degradation in aquatic microcosms. Biol Conserv 183: 85-92.
14. Pilliod et al. (2013) Estimating occupancy and abundance of stream amphibians using environmental DNA from filtered water samples. Can J Fish Aquat Sci 70: 1123-1130.
15. Berthelot et al. (2014) The rainbow trout genome provides novel insights into evolution after whole-genome duplication in vertebrates. Nat Commun 5: 3657.
16. Iulia et al. (2013) The evidence of contaminant bacterial DNA in several commercial Taq polymerases. Rom Biotechnol Lett 18: 8007-8012.
17. Mühl et al. (2010) Activity and DNA contamination of commercial polymerase chain reaction reagents for the universal 16S rDNA real-time polymerase chain reaction detection of bacterial pathogens in blood. Diagn Microbiol Infect Dis 66: 41-49.
18. Naccache et al. (2013) The perils of pathogen discovery: origin of a novel parvovirus-like hybrid genome traced to nucleic acid extraction spin columns. J Virol 87: 11966-11977.
19. Champlot et al. (2010) An efficient multistrategy DNA decontamination procedure of PCR reagents for hypersensitive PCR applications. PLoS One 5: e13042.
20. Wilcox et al. (2013) Robust detection of rare species using environmental DNA: the importance of primer specificity. PLoS One 8: e59520.
21. Goldberg et al. (2011) Molecular detection of vertebrates in stream water: a demonstration using Rocky Mountain tailed frogs and Idaho giant salamanders. PLoS One 6: e22746.
22. Ficetola et al. (2008) Species detection using environmental DNA from water samples. Biol Lett 4: 423-425.
23. Carim et al. (2016) An environmental DNA assay for detecting Arctic grayling in the upper Missouri River basin, North America. Conservation Genet Resour: 1-3.
24. Orchard S (2012) Update on bullfrog control program in the western communities control corridor. Victoria: Capitol Regional District. 16 pp.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A method for analyzing environmental DNA (eDNA) from an environmental water sample, comprising:
   (i) filtering or isolating nucleic acid molecules from the environmental water sample, thereby obtaining an eDNA sample,
   (ii) contacting the eDNA in the eDNA sample with a forward and reverse positive control primer set specific for endogenous algae chloroplast DNA or both plant chloroplast and algae chloroplast DNA, wherein the positive control primer set comprises a forward primer consisting of SEQ ID NO: 1 (TCTAGGGATAACAGGCTGAT), and a reverse primer consisting of SEQ ID NO: 2 (TGAACCCAGCTCACGTAC); amplifying the eDNA, thereby generating amplicons; identifying the presence or absence of endogenous chloroplast DNA; and
   (iii) if endogenous chloroplast DNA is identified as present in step (ii), subsequently contacting the eDNA in the eDNA sample with a forward and reverse primer set specific for an animal group DNA and/or an animal species DNA;
   amplifying the eDNA, thereby generating amplicons; and
   identifying the presence or absence of animal group DNA and/or animal species DNA; or
   (iv) if endogenous chloroplast DNA is identified as absent in step (ii), subsequently cleaning-up the eDNA sample with a PCR inhibitor removal column, thereby producing a cleaned-up eDNA sample and subsequently analyzing the cleaned-up eDNA sample by repeating step (ii) and step (iii).

2. The method of claim 1, wherein the environmental water sample is a fresh water sample or salt water sample.

3. The method of claim 1, further comprising identifying a false negative due to low sample quality if endogenous chloroplast DNA is identified as absent in the cleaned-up eDNA sample.

4. The method of claim 1, wherein the amplifying comprises using quantitative real-time PCR (qPCR).

5. The method of claim 1, further comprising contacting the eDNA sample or the amplicons with:
   a labeled nucleic acid probe specific for algae chloroplast DNA or both plant chloroplast and algae chloroplast DNA; and
   a labeled nucleic acid probe specific for the animal group DNA and/or a labeled nucleic acid probe specific for the animal species DNA.

6. The method of claim 1, wherein the inhibitor removal column comprises a size-exclusion column.

7. The method of claim 1, wherein the forward and reverse primer set specific for an animal group DNA and/or an animal species DNA is specific for an animal group DNA and is specific for a plurality of mammals, amphibians, fish, or invertebrates.

8. The method of claim 7, wherein the forward and reverse primer set specific for an animal group DNA and/or an animal species DNA is specific for an animal group DNA and
   the forward primer specific for animal group DNA comprises the nucleic acid sequence of SEQ ID NO: 4 (AGGYGGATTTAGYAGTAAAAAG) and the reverse primer specific for animal group DNA comprises the nucleic acid sequence of SEQ ID NO: 5 (TAYACTTACCATGTTACGACTT);
   the forward primer specific for animal group DNA comprises the nucleic acid sequence of SEQ ID NO: 7 (GGAAAGRTGAAATAGAAATGAAA) and the reverse primer specific for animal group DNA comprises the nucleic acid sequence of SEQ ID NO: 8 (GTAGCTCRCTTAGTTTCGGG);
   the forward primer specific for animal group DNA comprises the nucleic acid sequence of SEQ ID NO: 10 (AGTTACCCTRGGGATAACAG) and the reverse primer specific for animal group DNA comprises the nucleic acid sequence of SEQ ID NO: 11 (AACAAACGAACCWTTAGTAGC);

the forward primer specific for animal group DNA comprises the nucleic acid sequence of SEQ ID NO: 25 (AAAGGACTTGGCGGTRCTTT) and the reverse primer specific for animal group DNA comprises the nucleic acid sequence of SEQ ID NO: 26 (CCAAGCACACTTTCCAGTATG);

the forward primer specific for animal group DNA comprises the nucleic acid sequence of SEQ ID NO: 52 and the reverse primer specific for animal group DNA comprises the nucleic acid sequence of SEQ ID NO: 53; and/or the forward primer specific for animal group DNA comprises the nucleic acid sequence of SEQ ID NO: 55 and the reverse primer specific for animal group DNA comprises the nucleic acid sequence of SEQ ID NO: 56.

9. The method of claim 5, wherein the labeled nucleic acid probe specific for the animal group DNA and/or a labeled nucleic acid probe specific for the animal species DNA is specific for animal group DNA and comprises the nucleic acid sequence of SEQ ID NO: 6 (ACACACCGCCCGTCACCCTC), the nucleic acid sequence of SEQ ID NO: 9 (TCGTACCTTTTGCATCATGGT), the nucleic acid sequence of SEQ ID NO: 12 (TTTACGACCTCGATGTTGGATCAG), the nucleic acid sequence of SEQ ID NO: 27 (ATGAAGYACGCACACACCGCCCG), the nucleic acid sequence of SEQ ID NO: 54, and/or the nucleic acid sequence of SEQ ID NO: 57.

10. The method of claim 1, wherein the forward and reverse primer set specific for an animal group DNA and/or an animal species DNA is specific for the animal species DNA and is specific for one or up to two or up to three or up to four species of mammal, amphibian, fish, or invertebrate.

11. The method of claim 10, wherein the forward and reverse primer set specific for the animal species DNA is specific for: *Anaxyrus* (*Bufo*) *boreas* (Western toad), *Ascaphus montanus* (Rocky Mountain tailed frog), *Ascaphus truei* (Pacific (Coastal) tailed frog), *Lithobates* (*Rana*) *catesbeiana* (North American bullfrog), *Lithobates pipiens* (Northern leopard frog), *Rana aurora* (Northern red-legged frog), *Rana cascadae* (Cascades frog), *Rana luteiventris* (Columbia spotted frog), *Rana pretiosa* (Oregon spotted frog), *Sorex bendirii* (Pacific water shrew), *Lithobates* (*Rana*) *sylvaticus* (Wood frog), *Cottus cognatus* (Slimy Sculpin), *Prosopium cylindraceum* (Round Whitefish), *Salvelinus malma* (Dolly Varden), *Thymallus arcticus* (Arctic Grayling), *Oncorhynchus tschawytscha* (Chinook Salmon), *Oncorhynchus kisutch* (Coho Salmon), or *Dicamptodon tenebrosus* (Giant Pacific Salamander).

12. The method of claim 11, wherein the forward and reverse primer set specific for the animal species DNA is specific for *Lithobates* (*Rana*) *catesbeiana* and the forward primer specific for animal species DNA comprises the nucleic acid sequence of SEQ ID NO: 13 (TTTTCACTTCATCCTCCCGTTT) and the reverse primer specific for animal species DNA comprises the nucleic acid sequence of SEQ ID NO: 14 (GGGTTGGATGAGCCAGTTTG); or the forward primer specific for animal species DNA comprises the nucleic acid sequence of SEQ ID NO: 16 (GAGAACGCCCTTTAAATCTT) and the reverse primer specific for animal species DNA comprises the nucleic acid sequence of SEQ ID NO: 17 (GTCAAGCTGACGCTCATACG);

and the method optionally uses a probe specific for animal species DNA, wherein the probe comprises the nucleic acid sequence of SEQ ID NO: 15 (TTATCGCAGCAGCAAGTATGA) or the nucleic acid sequence of SEQ ID NO: 18 (ACAAACCCTCCGCCCACAAC).

13. The method of claim 1, wherein the positive control primer set further comprises at least one of:

(a) a forward primer comprising the nucleic acid sequence of SEQ ID NO: 130 (CACATTCACCGTGCTATGCA), and a reverse primer comprising the nucleic acid sequence of SEQ ID NO: 131 (GGCATGTGCCATACGTGAAT);

(b) a forward primer comprising the nucleic acid sequence of SEQ ID NO: 132 (GATGACGTCAAGTCAGCATG), and a reverse primer comprising the nucleic acid sequence of SEQ ID NO: 133 (CTACCTTGTTACGACTTCAC);

(c) a forward primer comprising the nucleic acid sequence of SEQ ID NO: 134 (TTGCGTCTGATTAGCTAGTT), and a reverse primer comprising the nucleic acid sequence of SEQ ID NO: 135 (GAGTTAGCCGATGCTTATTC); or (d) a forward primer comprising the nucleic acid sequence of SEQ ID NO: 136 (CCGTAACTTCGGGAGAAG), and a reverse primer comprising the nucleic acid sequence of SEQ ID NO: 137 (GCACTGGGCAGGCGTCAG).

14. The method of claim 11, wherein the forward and reverse primer set specific for the animal species DNA is specific for *Anaxyrus* (*Bufo*) *boreas* and the forward primer specific for animal species DNA comprises the nucleic acid sequence of SEQ ID NO: 28 (TATACTATGGCTCATACCTC) and the reverse primer specific for animal species DNA comprises the nucleic acid sequence of SEQ ID NO: 29 (GGTTGCGTTATCTACCGAG);

and the method optionally uses a probe specific for animal species DNA, wherein the probe comprises the nucleic acid sequence of SEQ ID NO: 30 (TTAGTTATAGCCACAGCGTTTGTGGG).

15. The method of claim 11, wherein the forward and reverse primer set specific for the animal species DNA is specific for (a) *Ascaphus truei*, and the forward primer specific for animal species DNA comprises the nucleic acid sequence of SEQ ID NO: 31 (GAACATTGGCATTATCCTACTT) and the reverse primer specific for animal species DNA comprises the nucleic acid sequence of SEQ ID NO: 32 (AGGCGAAAAATCGTGTTAAC), and the method optionally uses a probe specific for animal species DNA, wherein the probe comprises the nucleic acid sequence of SEQ ID NO: 33 (CGCTTTTGTAGGGTATGTGTTACCG);

(b) *Lithobates pipiens*, and the forward primer specific for animal species DNA comprises the nucleic acid sequence of SEQ ID NO: 34 (AGCTTACCATGTGAACGTCTT) and the reverse primer specific for animal species DNA comprises the nucleic acid sequence of SEQ ID NO: 35 (TACTACTAAATCCACCTTCGCT), and the method optionally uses a probe specific for animal species DNA, wherein the probe comprises the nucleic acid sequence of SEQ ID

NO: 36 (CAATTGGCTACAATTTCTAATATAGA-ACAA);

(c) *Rana aurora* and the forward primer specific for animal species DNA comprises the nucleic acid sequence of SEQ ID NO: 37 (TGAAGAAGCGG-GAATCAAA) and the reverse primer specific for animal species DNA comprises the nucleic acid sequence of SEQ ID NO: 38 (GCATACAGAT-TTCTTGTGTGTG), and the method optionally uses a probe specific for animal species DNA, wherein the probe comprises the nucleic acid sequence of SEQ ID NO: 39 (TAAACTCATCATACACCTCTGTGCTC);

(d) *Rana cascadae* and the forward primer specific for animal species DNA comprises the nucleic acid sequence of SEQ ID NO: 40 (CCTAATTGCC-CAAATCGCT) and the reverse primer specific for animal species DNA comprises the nucleic acid sequence of SEQ ID NO: 41 (CTCAAAATGA-CATCTGGCCC), and the the method optionally uses a probe specific for animal species DNA, wherein the probe comprises the nucleic acid sequence of SEQ ID NO: 42 (TGGCTGGCTCCTTCGTAATTTACATG);

(e) *Rana luteiventris* and the forward primer specific for animal species DNA comprises the nucleic acid sequence of SEQ ID NO: 43 (TTCCTCTAC-CAATCCCCTAT) and the reverse primer specific for animal species DNA comprises the nucleic acid sequence of SEQ ID NO: 44 (CCAGGAAAACAGTG-CATAAG), and the method optionally uses a probe specific for animal species DNA, wherein the probe comprises the nucleic acid sequence of SEQ ID NO: 45 (CAGCCTAACCGTTTACACAATTTTGGG);

(f) *Rana pretiosa* and the forward primer specific for animal species DNA comprises the nucleic acid sequence of SEQ ID NO: 46 (GTAACCTC-CATGCTAACGGT) and the reverse primer specific for animal species DNA comprises the nucleic acid sequence of SEQ ID NO: 47 (CTATCACTAG-GAATAGGAGGATC), and the method optionally uses a probe specific for animal species DNA, wherein the probe comprises the nucleic acid sequence of SEQ ID NO: 48 (TTTCCACATCGGCCGAGGCCTC);

(g) *Sorex bendirii* and the forward primer specific for animal species DNA comprises the nucleic acid sequence of SEQ ID NO: 49 (AAACATGAAA-CATCGGAGTAC) and the reverse primer specific for animal species DNA comprises the nucleic acid sequence of SEQ ID NO: 50 (ATAATGAAAGGTAG-GATAAAA), and the method optionally uses a probe specific for animal species DNA, wherein the probe comprises the nucleic acid sequence of SEQ ID NO: 51 (CGCAACAGTAATTACAAACCTACTATCA);

(h) *Lithobates* (*Rana*) *sylvaticus* and the forward primer specific for animal species DNA comprises the nucleic acid sequence of SEQ ID NO: 64 and the reverse primer specific for animal species DNA comprises the nucleic acid sequence of SEQ ID NO: 65, and the method optionally uses a probe specific for animal species DNA, wherein the probe comprises the nucleic acid sequence of SEQ ID NO: 66;

(i) *Cottus cognatus* and the forward primer specific for animal species DNA comprises the nucleic acid sequence of SEQ ID NO: 67, 70 or 73, and the reverse primer specific for animal species DNA comprises the nucleic acid sequence of SEQ ID NO: 68, 71, or 74, and the method optionally uses a probe specific for animal species DNA, wherein the probe comprises the nucleic acid sequence of SEQ ID NO: 69, 72 or 75;

(j) *Prosopium cylindraceum* and the forward primer specific for animal species DNA comprises the nucleic acid sequence of SEQ ID NO: 76, 79 or 82, and the reverse primer specific for animal species DNA comprises the nucleic acid sequence of SEQ ID NO: 77, 80, or 83, and the method optionally uses a probe specific for animal species DNA, wherein the probe comprises the nucleic acid sequence of SEQ ID NO: 78, 81 or 84;

(k) *Salvelinus malma* and the forward primer specific for animal species DNA comprises the nucleic acid sequence of SEQ ID NO: 85, 88 or 91, and the reverse primer specific for animal species DNA comprises the nucleic acid sequence of SEQ ID NO: 86, 89, or 92, and the method optionally uses a probe specific for animal species DNA, wherein the probe comprises the nucleic acid sequence of SEQ ID NO: 87, 90 or 93;

(l) *Thymallus arcticus* and the forward primer specific for animal species DNA comprises the nucleic acid sequence of SEQ ID NO: 94, 97 or 100, and the reverse primer specific for animal species DNA comprises the nucleic acid sequence of SEQ ID NO: 95, 98, or 101, and the method optionally uses a probe specific for animal species DNA, wherein the probe comprises the nucleic acid sequence of SEQ ID NO: 96, 99 or 102;

(m) *Oncorhynchus tschawytscha* and the forward primer specific for animal species DNA comprises the nucleic acid sequence of SEQ ID NO: 103, 106 or 109, and the reverse primer specific for animal species DNA comprises the nucleic acid sequence of SEQ ID NO: 104, 107, or 110, and the method optionally uses a probe specific for animal species DNA, wherein the probe comprises the nucleic acid sequence of SEQ ID NO: 105, 108, or 111;

(n) *Oncorhynchus kisutch* and the forward primer specific for animal species DNA comprises the nucleic acid sequence of SEQ ID NO: 112, 115, 118 or 121, and the reverse primer specific for animal species DNA comprises the nucleic acid sequence of SEQ ID NO: 113, 116, 119 or 122, and the method optionally uses a probe specific for animal species DNA, wherein the probe comprises the nucleic acid sequence of SEQ ID NO: 114, 117, 120, or 123; and/or (o) *Dicamptodon tenebrosus* and the forward primer specific for animal species DNA comprises the nucleic acid sequence of SEQ ID NO: 124 or 127, and the reverse primer specific for animal species DNA comprises the nucleic acid sequence of SEQ ID NO: 125 or 128, and the method optionally uses a probe specific for animal species DNA, wherein the probe comprises the nucleic acid sequence of SEQ ID NO: 126 or 129.

16. The method of claim 1, further comprising contacting the eDNA sample or the amplicons with a labeled nucleic acid probe comprising SEQ ID NO: 3 (TTTGGCACCTC-GATGTCGG).

17. The method of claim 4, further comprising contacting the eDNA sample or the amplicons with a labeled nucleic acid probe comprising SEQ ID NO: 3 (TTTGGCACCTC-GATGTCGG).

* * * * *

SEQUENCE LISTING

```
<160> NUMBER OF SEQ ID NOS: 137

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 1

tctagggata acaggctgat                                              20


<210> SEQ ID NO 2
<211> LENGTH: 18
<212> TYPE: DNA
<213> ORGANISM: Artificial Sequence
<220> FEATURE:
<223> OTHER INFORMATION: Synthetic Oligo

<400> SEQUENCE: 2

tgaacccagc tcacgtac                                                18


<210> SEQ ID NO 3
<211> LENGTH: 19
<212> TYPE: DNA
<213> ORGANISM: Artificial Sequence
<220> FEATURE:
```

-continued

<223> OTHER INFORMATION: Synthetic Oligo

<400> SEQUENCE: 3
tttggcacct cgatgtcgg 19

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 4
aggyggattt agyagtaaaa ag 22

<210> SEQ ID NO 5
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 5
tayacttacc atgttacgac tt 22

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 6
acacaccgcc cgtcaccctc 20

<210> SEQ ID NO 7
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 7
ggaaagrtga aatagaaatg aaa 23

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 8
gtagctcrct tagtttcggg 20

<210> SEQ ID NO 9
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 9
tcgtaccttt tgcatcatgg t 21

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 10
agttaccctr gggataacag 20

<210> SEQ ID NO 11
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 11
aacaaacgaa ccwttagtag c 21

<210> SEQ ID NO 12
<211> LENGTH: 24
<212> TYPE: DNA
<213> ORGANISM: Artificial Sequence
<220> FEATURE:
<223> OTHER INFORMATION: Synthetic Oligo

<400> SEQUENCE: 12
tttacgacct cgatgttgga tcag 24

<210> SEQ ID NO 13
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 13
ttttcacttc atcctcccgt tt 22

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 14
gggttggatg agccagtttg 20

<210> SEQ ID NO 15
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 15
ttatcgcagc agcaagtatg a 21

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligo -continued

<400> SEQUENCE: 16
gagaacgccc tttaaatctt 20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 17
gtcaagctga cgctcatacg 20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 18
acaaaccctc cgcccacaac 20

<210> SEQ ID NO 19
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 19
acgtcaacta tggctggcta atc 23

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 20
gtcctcggcc aatgtgaaga 20

<210> SEQ ID NO 21
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 21
catgcaaatg gagcatcatt c 21

<210> SEQ ID NO 22
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 22
actttattac ggctcttact tg 22

<210> SEQ ID NO 23
<211> LENGTH: 21

-continued

<212> TYPE: DNA
<213> ORGANISM: Artificial Sequence
<220> FEATURE:
<223> OTHER INFORMATION: Synthetic Oligo

<400> SEQUENCE: 23
gtacgtttcc gatgtaaggg a 21

<210> SEQ ID NO 24
<211> LENGTH: 27
<212> TYPE: DNA
<213> ORGANISM: Artificial Sequence
<220> FEATURE:
<223> OTHER INFORMATION: Synthetic Oligo

<400> SEQUENCE: 24
atacgtatta ccatgaggac aaatatc 27

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 25
aaaggacttg gcggtrcttt 20

<210> SEQ ID NO 26
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 26
ccaagcacac tttccagtat g 21

<210> SEQ ID NO 27
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 27
atgaagyacg cacacaccgc ccg 23

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 28
tatactatgg ctcatacctc 20

<210> SEQ ID NO 29
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 29

```
ggttgcgtta tctaccgag                                               19


<210> SEQ ID NO 30
<211> LENGTH: 26
<212> TYPE: DNA
<213> ORGANISM: Artificial Sequence
<220> FEATURE:
<223> OTHER INFORMATION: Synthetic Oligo

<400> SEQUENCE: 30

ttagttatag ccacagcgtt tgtggg                                      26


<210> SEQ ID NO 31
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 31

gaacattggc attatcctac tt                                          22


<210> SEQ ID NO 32
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 32

aggcgaaaaa tcgtgttaac                                             20


<210> SEQ ID NO 33
<211> LENGTH: 25
<212> TYPE: DNA
<213> ORGANISM: Artificial Sequence
<220> FEATURE:
<223> OTHER INFORMATION: Synthetic Oligo

<400> SEQUENCE: 33

cgcttttgta gggtatgtgt taccg                                       25


<210> SEQ ID NO 34
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 34

agcttaccat gtgaacgtct t                                           21


<210> SEQ ID NO 35
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 35

tactactaaa tccaccttcg ct                                          22


<210> SEQ ID NO 36
<211> LENGTH: 30
<212> TYPE: DNA
<213> ORGANISM: Artificial Sequence
```

-continued

<220> FEATURE:
<223> OTHER INFORMATION: Synthetic Oligo

<400> SEQUENCE: 36
caattggcta caatttctaa tatagaacaa 30

<210> SEQ ID NO 37
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 37
tgaagaagcg ggaatcaaa 19

<210> SEQ ID NO 38
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 38
gcatacagat ttcttgtgtg tg 22

<210> SEQ ID NO 39
<211> LENGTH: 26
<212> TYPE: DNA
<213> ORGANISM: Artificial Sequence
<220> FEATURE:
<223> OTHER INFORMATION: Synthetic Oligo

<400> SEQUENCE: 39
taaactcatc atacacctct gtgctc 26

<210> SEQ ID NO 40
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 40
cctaattgcc caaatcgct 19

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 41
ctcaaaatga catctggccc 20

<210> SEQ ID NO 42
<211> LENGTH: 26
<212> TYPE: DNA
<213> ORGANISM: Artificial Sequence
<220> FEATURE:
<223> OTHER INFORMATION: Synthetic Oligo

<400> SEQUENCE: 42
tggctggctc cttcgtaatt tacatg 26

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 43
ttcctctacc aatcccctat 20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 44
ccaggaaaac agtgcataag 20

<210> SEQ ID NO 45
<211> LENGTH: 27
<212> TYPE: DNA
<213> ORGANISM: Artificial Sequence
<220> FEATURE:
<223> OTHER INFORMATION: Synthetic Oligo

<400> SEQUENCE: 45
cagcctaacc gtttacacaa ttttggg 27

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 46
gtaacctcca tgctaacggt 20

<210> SEQ ID NO 47
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 47
ctatcactag gaataggagg atc 23

<210> SEQ ID NO 48
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 48
tttccacatc ggccgaggcc tc 22

<210> SEQ ID NO 49
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 49
aaacatgaaa catcggagta c 21

<210> SEQ ID NO 50
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 50
ataatgaaag gtaggataaa a 21

<210> SEQ ID NO 51
<211> LENGTH: 28
<212> TYPE: DNA
<213> ORGANISM: Artificial Sequence
<220> FEATURE:
<223> OTHER INFORMATION: Synthetic Oligo

<400> SEQUENCE: 51
cgcaacagta attacaaacc tactatca 28

<210> SEQ ID NO 52
<211> LENGTH: 18
<212> TYPE: DNA
<213> ORGANISM: Artificial Sequence
<220> FEATURE:
<223> OTHER INFORMATION: Synthetic Oligo

<400> SEQUENCE: 52
garggytata ctgtctcc 18

<210> SEQ ID NO 53
<211> LENGTH: 18
<212> TYPE: DNA
<213> ORGANISM: Artificial Sequence
<220> FEATURE:
<223> OTHER INFORMATION: Synthetic Oligo

<400> SEQUENCE: 53
atcccyaggg taacttgg 18

<210> SEQ ID NO 54
<211> LENGTH: 26
<212> TYPE: DNA
<213> ORGANISM: Artificial Sequence
<220> FEATURE:
<223> OTHER INFORMATION: Synthetic Oligo

<400> SEQUENCE: 54
ataagacgag aagacccyat ggagct 26

<210> SEQ ID NO 55
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 55
cacctagagg agcctgttct a 21

<210> SEQ ID NO 56

<211> LENGTH: 20
<212> TYPE: DNA
<213> ORGANISM: Artificial Sequence
<220> FEATURE:
<223> OTHER INFORMATION: Synthetic Oligo

<400> SEQUENCE: 56
ctacacctcg acctgacgtt 20

<210> SEQ ID NO 57
<211> LENGTH: 26
<212> TYPE: DNA
<213> ORGANISM: Artificial Sequence
<220> FEATURE:
<223> OTHER INFORMATION: Synthetic Oligo

<400> SEQUENCE: 57
tatataccrc cgtcgtcagc ttaccc 26

<210> SEQ ID NO 58
<211> LENGTH: 24
<212> TYPE: DNA
<213> ORGANISM: Artificial Sequence
<220> FEATURE:
<223> OTHER INFORMATION: Synthetic Oligo

<400> SEQUENCE: 58
agtacctgaa tgatatttat tacc 24

<210> SEQ ID NO 59
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 59
ttctataaat ggactttcaa cg 22

<210> SEQ ID NO 60
<211> LENGTH: 28
<212> TYPE: DNA
<213> ORGANISM: Artificial Sequence
<220> FEATURE:
<223> OTHER INFORMATION: Synthetic Oligo

<400> SEQUENCE: 60
ctagaggttt acaattcaga cctttaag 28

<210> SEQ ID NO 61
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 61
ctaatgctgt aggttactat gg 22

<210> SEQ ID NO 62
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 62
ccactaacta actcagattc ag 22

<210> SEQ ID NO 63
<211> LENGTH: 25
<212> TYPE: DNA
<213> ORGANISM: Artificial Sequence
<220> FEATURE:
<223> OTHER INFORMATION: Synthetic Oligo

<400> SEQUENCE: 63
ctttcttagg gtcattaagg agtac 25

<210> SEQ ID NO 64
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 64
tctatcgcac acatctgtcg a 21

<210> SEQ ID NO 65
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 65
actaggtcgg agccaatata g 21

<210> SEQ ID NO 66
<211> LENGTH: 26
<212> TYPE: DNA
<213> ORGANISM: Artificial Sequence
<220> FEATURE:
<223> OTHER INFORMATION: Synthetic Oligo

<400> SEQUENCE: 66
ttactacggc tcttatcttt ataaag 26

<210> SEQ ID NO 67
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 67
taaagccaaa catcttcaag a 21

<210> SEQ ID NO 68
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 68
gcggatagtg ggtgtgtagt a 21

<210> SEQ ID NO 69
<211> LENGTH: 27
<212> TYPE: DNA

<213> ORGANISM: Artificial Sequence
<220> FEATURE:
<223> OTHER INFORMATION: Synthetic Oligo

<400> SEQUENCE: 69
tcgctttatc tgatctgaat ccacgaa 27

<210> SEQ ID NO 70
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 70
cctcggtctt tgcttaatta t 21

<210> SEQ ID NO 71
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 71
ctacgaaagc ggttattatt ac 22

<210> SEQ ID NO 72
<211> LENGTH: 26
<212> TYPE: DNA
<213> ORGANISM: Artificial Sequence
<220> FEATURE:
<223> OTHER INFORMATION: Synthetic Oligo

<400> SEQUENCE: 72
atcagttggt catatttgcc gagatg 26

<210> SEQ ID NO 73
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 73
cagttcctta cattggcaa 19

<210> SEQ ID NO 74
<211> LENGTH: 18
<212> TYPE: DNA
<213> ORGANISM: Artificial Sequence
<220> FEATURE:
<223> OTHER INFORMATION: Synthetic Oligo

<400> SEQUENCE: 74
attaagagcg ctgcaaag 18

<210> SEQ ID NO 75
<211> LENGTH: 27
<212> TYPE: DNA
<213> ORGANISM: Artificial Sequence
<220> FEATURE:
<223> OTHER INFORMATION: Synthetic Oligo

<400> SEQUENCE: 75
ccttggttta aactcagatg cagacaa 27

<210> SEQ ID NO 76
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 76
aagaaaagcc tgcacaaata t 21

<210> SEQ ID NO 77
<211> LENGTH: 18
<212> TYPE: DNA
<213> ORGANISM: Artificial Sequence
<220> FEATURE:
<223> OTHER INFORMATION: Synthetic Oligo

<400> SEQUENCE: 77
gtccgttgat cggcattt 18

<210> SEQ ID NO 78
<211> LENGTH: 27
<212> TYPE: DNA
<213> ORGANISM: Artificial Sequence
<220> FEATURE:
<223> OTHER INFORMATION: Synthetic Oligo

<400> SEQUENCE: 78
ctaacaagta aaaacgcagt gacccct 27

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 79
ctcaaatcct tacagggttg 20

<210> SEQ ID NO 80
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 80
cgcggagagt agatttgtaa ta 22

<210> SEQ ID NO 81
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 81
tcgggacgta agctacggct gac 23

<210> SEQ ID NO 82
<211> LENGTH: 17
<212> TYPE: DNA
<213> ORGANISM: Artificial Sequence
<220> FEATURE:

-continued

<223> OTHER INFORMATION: Synthetic Oligo

<400> SEQUENCE: 82
gcccatcgca gatggta 17

<210> SEQ ID NO 83
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 83
taattacgct aagtaaaata agc 23

<210> SEQ ID NO 84
<211> LENGTH: 24
<212> TYPE: DNA
<213> ORGANISM: Artificial Sequence
<220> FEATURE:
<223> OTHER INFORMATION: Synthetic Oligo

<400> SEQUENCE: 84
cgtgcttgca ctctccagcc tagc 24

<210> SEQ ID NO 85
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 85
gggcttagct gtctcctctc 20

<210> SEQ ID NO 86
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 86
ctaggggtca ctgcgtttc 19

<210> SEQ ID NO 87
<211> LENGTH: 29
<212> TYPE: DNA
<213> ORGANISM: Artificial Sequence
<220> FEATURE:
<223> OTHER INFORMATION: Synthetic Oligo

<400> SEQUENCE: 87
tacataagac gagaagaccc tatggagct 29

<210> SEQ ID NO 88
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 88
ttacatacat atcgcccgg 19

<210> SEQ ID NO 89
<211> LENGTH: 18
<212> TYPE: DNA
<213> ORGANISM: Artificial Sequence
<220> FEATURE:
<223> OTHER INFORMATION: Synthetic Oligo

<400> SEQUENCE: 89
tcggcgtcgg agttaata 18

<210> SEQ ID NO 90
<211> LENGTH: 24
<212> TYPE: DNA
<213> ORGANISM: Artificial Sequence
<220> FEATURE:
<223> OTHER INFORMATION: Synthetic Oligo

<400> SEQUENCE: 90
cttcgttatt gcagccgcca cagt 24

<210> SEQ ID NO 91
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 91
ccaaaccttc aacgtagct 19

<210> SEQ ID NO 92
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 92
gtattctacg ttgaatcctg aa 22

<210> SEQ ID NO 93
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 93
cttggccgaa acaaaccgtg c 21

<210> SEQ ID NO 94
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 94
gagaggccca agttgatagt 20

<210> SEQ ID NO 95
<211> LENGTH: 22
<212> TYPE: DNA
<213> ORGANISM: Artificial Sequence
<220> FEATURE:
<223> OTHER INFORMATION: Synthetic Oligo -continued

<400> SEQUENCE: 95
acccattttg cttactatat ga 22

<210> SEQ ID NO 96
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 96
cccctgaacc cacgacagct atg 23

<210> SEQ ID NO 97
<211> LENGTH: 18
<212> TYPE: DNA
<213> ORGANISM: Artificial Sequence
<220> FEATURE:
<223> OTHER INFORMATION: Synthetic Oligo

<400> SEQUENCE: 97
cccacacagg agtgcaag 18

<210> SEQ ID NO 98
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 98
tgcgttttta cttggtagga 20

<210> SEQ ID NO 99
<211> LENGTH: 25
<212> TYPE: DNA
<213> ORGANISM: Artificial Sequence
<220> FEATURE:
<223> OTHER INFORMATION: Synthetic Oligo

<400> SEQUENCE: 99
atataagagg tcccgcctgc cctgt 25

<210> SEQ ID NO 100
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 100
atctcctacg aggttagttt g 21

<210> SEQ ID NO 101
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 101
aaatactacg gatagtagag cc 22

<210> SEQ ID NO 102
<211> LENGTH: 28

<212> TYPE: DNA
<213> ORGANISM: Artificial Sequence
<220> FEATURE:
<223> OTHER INFORMATION: Synthetic Oligo

<400> SEQUENCE: 102
tgaactagtc tccggattca atgtagaa 28

<210> SEQ ID NO 103
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 103
acctagagga gcctgttcta t 21

<210> SEQ ID NO 104
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 104
gcgtggttcg tagtactcta g 21

<210> SEQ ID NO 105
<211> LENGTH: 28
<212> TYPE: DNA
<213> ORGANISM: Artificial Sequence
<220> FEATURE:
<223> OTHER INFORMATION: Synthetic Oligo

<400> SEQUENCE: 105
tccatagtaa gcaaaatgga caaaaccc 28

<210> SEQ ID NO 106
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 106
cgaccgaaaa ggagacaaa 19

<210> SEQ ID NO 107
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 107
cctcaaggtc ctaagaaagc t 21

<210> SEQ ID NO 108
<211> LENGTH: 29
<212> TYPE: DNA
<213> ORGANISM: Artificial Sequence
<220> FEATURE:
<223> OTHER INFORMATION: Synthetic Oligo

<400> SEQUENCE: 108
attttaagcc tagaaaagca gagattaaa 29

<210> SEQ ID NO 109
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 109
cgaggacttt attatggctc t 21

<210> SEQ ID NO 110
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 110
atctttgtat gagaagtagg ga 22

<210> SEQ ID NO 111
<211> LENGTH: 25
<212> TYPE: DNA
<213> ORGANISM: Artificial Sequence
<220> FEATURE:
<223> OTHER INFORMATION: Synthetic Oligo

<400> SEQUENCE: 111
ctgaggcggg ttctctgttg acaac 25

<210> SEQ ID NO 112
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 112
ataataactg cctttgtggg a 21

<210> SEQ ID NO 113
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 113
gcaaaaagag ctaaggatgt c 21

<210> SEQ ID NO 114
<211> LENGTH: 28
<212> TYPE: DNA
<213> ORGANISM: Artificial Sequence
<220> FEATURE:
<223> OTHER INFORMATION: Synthetic Oligo

<400> SEQUENCE: 114
tactctaaca cgatttttcg cctttcac 28

<210> SEQ ID NO 115
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 115
cttgtcctta tggttgtacc a 21

<210> SEQ ID NO 116
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 116
tgaaagaact aggaagatgg c 21

<210> SEQ ID NO 117
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 117
ttaacctgaa tcgggggcat gcc 23

<210> SEQ ID NO 118
<211> LENGTH: 18
<212> TYPE: DNA
<213> ORGANISM: Artificial Sequence
<220> FEATURE:
<223> OTHER INFORMATION: Synthetic Oligo

<400> SEQUENCE: 118
cacatccccg ctttacca 18

<210> SEQ ID NO 119
<211> LENGTH: 18
<212> TYPE: DNA
<213> ORGANISM: Artificial Sequence
<220> FEATURE:
<223> OTHER INFORMATION: Synthetic Oligo

<400> SEQUENCE: 119
ggagggaggc ctgctagg 18

<210> SEQ ID NO 120
<211> LENGTH: 24
<212> TYPE: DNA
<213> ORGANISM: Artificial Sequence
<220> FEATURE:
<223> OTHER INFORMATION: Synthetic Oligo

<400> SEQUENCE: 120
atcaccctgg cccttgtact gtgg 24

<210> SEQ ID NO 121
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 121
cccttttgac ctcacagag 19

-continued

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 122
ggttcagggc agttagttct 20

<210> SEQ ID NO 123
<211> LENGTH: 26
<212> TYPE: DNA
<213> ORGANISM: Artificial Sequence
<220> FEATURE:
<223> OTHER INFORMATION: Synthetic Oligo

<400> SEQUENCE: 123
tgccctcttt ttcctagccg agtacg 26

<210> SEQ ID NO 124
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 124
aggcgcaaca gttatcacg 19

<210> SEQ ID NO 125
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 125
aatgccatgt tgggttatta ga 22

<210> SEQ ID NO 126
<211> LENGTH: 26
<212> TYPE: DNA
<213> ORGANISM: Artificial Sequence
<220> FEATURE:
<223> OTHER INFORMATION: Synthetic Oligo

<400> SEQUENCE: 126
attgccctta gtattattca tctttt 26

<210> SEQ ID NO 127
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 127
cattatactg ctgatactat 20

<210> SEQ ID NO 128
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 128
ctatcattaa tagtaataag atc 23

<210> SEQ ID NO 129
<211> LENGTH: 27
<212> TYPE: DNA
<213> ORGANISM: Artificial Sequence
<220> FEATURE:
<223> OTHER INFORMATION: Synthetic Oligo

<400> SEQUENCE: 129
tatctactat gggtcatatt tatataa 27

<210> SEQ ID NO 130
<211> LENGTH: 20
<212> TYPE: DNA
<213> ORGANISM: Artificial Sequence
<220> FEATURE:
<223> OTHER INFORMATION: Example primer sequence

<400> SEQUENCE: 130
cacattcacc gtgctatgca 20

<210> SEQ ID NO 131
<211> LENGTH: 20
<212> TYPE: DNA
<213> ORGANISM: Artificial Sequence
<220> FEATURE:
<223> OTHER INFORMATION: Example primer sequence

<400> SEQUENCE: 131
ggcatgtgcc atacgtgaat 20

<210> SEQ ID NO 132
<211> LENGTH: 20
<212> TYPE: DNA
<213> ORGANISM: Artificial Sequence
<220> FEATURE:
<223> OTHER INFORMATION: Example primer sequence

<400> SEQUENCE: 132
gatgacgtca agtcagcatg 20

<210> SEQ ID NO 133
<211> LENGTH: 20
<212> TYPE: DNA
<213> ORGANISM: Artificial Sequence
<220> FEATURE:
<223> OTHER INFORMATION: Example primer sequence

<400> SEQUENCE: 133
ctaccttgtt acgacttcac 20

<210> SEQ ID NO 134
<211> LENGTH: 20
<212> TYPE: DNA
<213> ORGANISM: Artificial Sequence
<220> FEATURE:
<223> OTHER INFORMATION: Example primer sequence

<400> SEQUENCE: 134
ttgcgtctga ttagctagtt 20

<210> SEQ ID NO 135

```
<211> LENGTH: 20
<212> TYPE: DNA
<213> ORGANISM: Artificial Sequence
<220> FEATURE:
<223> OTHER INFORMATION: Example primer sequence

<400> SEQUENCE: 135

gagttagccg atgcttattc                                               20

<210> SEQ ID NO 136
<211> LENGTH: 18
<212> TYPE: DNA
<213> ORGANISM: Artificial Sequence
<220> FEATURE:
<223> OTHER INFORMATION: Example primer sequence

<400> SEQUENCE: 136

ccgtaacttc gggagaag                                                 18

<210> SEQ ID NO 137
<211> LENGTH: 18
<212> TYPE: DNA
<213> ORGANISM: Artificial Sequence
<220> FEATURE:
<223> OTHER INFORMATION: Example primer sequence

<400> SEQUENCE: 137

gcactgggca ggcgtcag                                                 18
```